US009907240B2

(12) United States Patent
Millenaar et al.

(10) Patent No.: US 9,907,240 B2
(45) Date of Patent: Mar. 6, 2018

(54) TOMATO PLANTS EXHIBITING TOLERANCE TO CONTINUOUS LIGHT

(75) Inventors: Franciscus Frank Millenaar, Varik (NL); Petrus Marinus Johannes Abraham van Poppel, Wageningen (NL)

(73) Assignee: Monsanto Invest B.V., Bergschenhoek (NL)

( * ) Notice: Subject to any disclaimer, the term of this patent is extended or adjusted under 35 U.S.C. 154(b) by 735 days.

(21) Appl. No.: 13/393,862

(22) PCT Filed: Sep. 6, 2010

(86) PCT No.: PCT/NL2010/050562
§ 371 (c)(1),
(2), (4) Date: May 1, 2012

(87) PCT Pub. No.: WO2011/028121
PCT Pub. Date: Mar. 10, 2011

(65) Prior Publication Data
US 2012/0255049 A1 Oct. 4, 2012

(30) Foreign Application Priority Data
Sep. 4, 2009 (EP) .................................... 09169555

(51) Int. Cl.
| | |
|---|---|
| *A01H 5/00* | (2006.01) |
| *C12N 15/82* | (2006.01) |
| *C12Q 1/02* | (2006.01) |
| *C12N 5/04* | (2006.01) |
| *A01H 1/04* | (2006.01) |

(52) U.S. Cl.
CPC ................ *A01H 1/04* (2013.01); *A01H 5/00* (2013.01)

(58) Field of Classification Search
None
See application file for complete search history.

(56) References Cited

FOREIGN PATENT DOCUMENTS

WO 2003/066866 A2 8/2003

OTHER PUBLICATIONS

Daskaloff and Ognjanova, 1965, Zeitschrift fur Pflanzenzüchtung 54: 169-181.*
Nuez et al., 1986, Z. Pflanzenzuchtg. 96: 200-206.*
Mueller et al., 2009, Plant Genome 2: 78-92.*
Withrow and Withrow, 1949, Plant Physiology 24: 657-663.*
Demers and Gosselin, 2002, Acta Horticulturae 580, ISHS 2002: 83-88.*
Bhatia et al., 2004, Plant Cell, Tissue and Organ Culture 78: 1-21.*
SGN-U269118, Solanum Genomics Network, pp. 1-7.*
Reinhold and Lankow, 1957, Der Deutsche Gartenbau 4: 35-36.*
CAFFARRI (Caffarri et al., 2005, Proteomics 5: 758-768.*
Damkjaer et al., 2009, The Plant Cell 21: 3245-3256.*
International Search Report for corresponding PCT/NL2010/050562, dated Dec. 16, 2010.
International Preliminary Report for corresponding PCT/NL2010/050562, dated Mar. 6, 2012.
Daskaloff, et al., "Das Verhalten von Lycopersicon esculentum Mill., L. racemigerum Lange und L. hirsutum Humb. et Bonpl. gegenuber Dauerbelichtung," Zeitschrift Fuer Pflanzenzuechtung, vol. 54, No. 2, Jan. 1, 1965.
Mueller, et al., "A Snapshot of the Emerging Tomato Genome Sequence," Plant Genome, Mar. 2009, vol. 2, No. 1, 78-92.
Nuez, et al., "Genetics of the Parthenocarpy for Tomato Varieties Sub-Arctic Plenty, 75/59 and Severianin," Z. Pflanzenzuchtg., 96, 200-206 (1986).
Ohyama, et al., "Potential Use of a 24-Hour Photoperiod (Continuous Light) with Alternating Air Temperature for Production of Tomato Plug Transplants in a Closed System," HortScience, 40(2), 374-377, 2005.
Tanksley, et al., "High Density Molecular Linkage Maps of the Tomato and Potato Genomes," Genetics Society of America, 132: 1141-1160, Dec. 1992.
Lanckow, "Die Leuchtentechnik bei der Zusatzbelichtung im Treibgemusebau," *Agrartechnik* A 3162, Heft 11:508-511, 1958.
Velez-Ramirez et al., "A single locus confers tolerance to continuous light and allows substantial yield increase in tomato," *Nature Communications* 5:4549, 2014.
Velez-Ramirez et al., "Plants under continuous light," *Trends in Plant Science* 16:310-318, 2011.
Warrington et al., "An Evaluation of Plant Growth and Development under Various Daily Quantum Integrals," *J. Amer. Soc. Hort. Sci.* 116(3):544-551, 1991.
Kearsey, "The principles of QTL analysis (a minimal mathematics approach)," *Journal of Experimental Botany*, 49(327):1619-1623, 1998.
Botstein et al., "Construction of a genetic map in man using restriction fragment length polymorphisms," *American Journal of Human Genetics* 32:314-331, 1980.

* cited by examiner

*Primary Examiner* — Amjad Abraham
*Assistant Examiner* — Bratislav Stankovic
(74) *Attorney, Agent, or Firm* — Dentons US LLP

(57) ABSTRACT

The present invention relates to a method of selecting a tomato plant comprising exposing a tomato plant and determining whether said plant exhibits tolerance to exposure to continuous light, wherein said tolerance is indicated by decreased level of chlorosis upon said exposure, and further determining whether said plant exhibits a significant increase in yield when exposed to continuous light. The invention further relates to a method for increasing the yield of a tomato plant line, said method comprising selecting a tomato plant by the method of the invention; crossing the thus selected plant with a plant of a said tomato plant line to produce offspring plants; optionally backcrossing or selfing said offspring plant to produce further offspring plants, and selecting from said offspring plants a plant having tolerance to continuous light and having increased yield as compared to said plant of the original tomato plant line.

9 Claims, 14 Drawing Sheets

Figure 11

MARKER 1:
GATGAGATTGTTACATGATTTTGTGCAGATCTAGCACAAGCCTTAGCCAAATTAAAGGAG[T/G]CCTCTCCATATT
CGGTCCCTCTGGTCATTTTCGGTCACATGCACAAACAGCTTGCTTCTG

MARKER 2:
TTTTCATTTTGCGTTTTCTGCAGGAGAGTTCAAATTGAACATCGAGTGCAACCATGCCAC[T/G]TTGGCTGGTCAC
AGGTTTGTGTGTTTTCAGTGCAAATTAACTATGTCCGTCTTTTGCACC

MARKER 3:
GTCATTACTATGTCCACAGATGCCACAGATCTAGATCA[A/T]CCGTTACTATAGCCACAGATGCCACAGATCTAGA
TCATATTATCCTTCTTGCATTTTGTG

MARKER 4:
TAGATTGCGTCTCCTGCGCTCCGTACTGGCTTTACTTCGTGAATGGGCACTTTCTGTCTT[T/C]GCACAGGGAATG
CCTACAAGTCTTACTGGAGCCTCTCTCATTCTTGCTGGAACTTTATCA

MARKER 5:
TTATGACTTAGCCAACGGGAAAACATTTAAANTGGATGTTTTTGTATATTTACCTCCAAT[A/T]AAACCCTAAATG
AATTTCATGACTAATAAATGGTTCAAANCAATGATATTTTCATCTTTA

MARKER 6:
TGTTATACCGTGATTTATANCAAATGATTGGACAATAAGGCCTTTCACCATTCTTGCTCT[T/C]GATGTCAGTGTC
ACTGAAAGTAACAGTAGTTGGAGTACCCATAATATTTGATCGGATGGA

MARKER 7:
AGGTCCTCATTGTCTGTGTTGCTCCGCCCTGCAATTGTCCTAAATTTAACTGAACTAATG[T/C]ATGGGGAAAAAT
GAAATGGGGATTCGTTTGTGCAGGGAGGATTTGAATCTGGTGCAGTGG

MARKER 8:
TATTTTAGCAGCTATAATGGTGGATACAATTGGTCGAAAATTCAGTGTGGCACTTATGTG[T/C]GGTTTAAGCTTC
CTGTTCCTTTTACCGCTTCTTGCACCTCAACTCCCTGCTTTNACTACT

MARKER 9:
AAAGGTCAGGCTATTGTTTCTTTTTTGTAGTTTGTAGTAGCACAATTAGGAACCAAATGC[A/G]TTGTGCTACAGT
AGTCTTAGTACAAGCTGGTGCAAATATACCTGCTACCGTTATGGTCCC

Figure 11 Continued

MARKER 10:
CGAGATGAAGAGAACCGGTGTGGCTCCTAATGTTGTCACTTATAATACGCTGATAAACGC[A/G]TATAGTCAGGTT
GGTAATTCTGAAATGGGAAGTAGGCTTTTCGAGGAGATGGCAAACAAT

MARKER 11:
TTNGAGAATCTTCCTTCTCCAGATACTCCTGCAGTATATGTGTCCAACCATCAGAGCTTT[T/C]TGGACATATATA
CATTACTTACTCTTGGGAGAAACTTCAAGTTCATC

MARKER 12:
TTTCAAGAACCTTAGTGATGTTAGCCCTATTAATACCTTGGCTGGAGGNAACTTATACTC[T/G]TTGAACTTCACC
GATGACTCTGGGACCGTTCATCTTAACTCAGGATGGTCTAGGACTAAA

MARKER 13:
GGCTGGCTTCGCCAGCCATGACGGAGTTGGAAATGGTAGTCATGGACTGGCTTGCTAATA[T/C]GTTGAAATTACC
AAAAACTTTCATGTTTTCTGGCACGGGTGGTGGTGTACTACAAAGTAC

MARKER 14:
ACTTGTGTTTAAATTGCAGATGTCATCAGATGGACCAACCCACAATGAGTTTGATTTTGA[A/G]TTTTTAGGCAAT
ACAACTGGTGAACCATATACAGTACAAACAAATGTGTATGTCAATGGT

MARKER 15:
TCAACTAAAGAAAGAACTGCAACTGAACTCCCTTCAAACTGACACGATTAAATGCCTGCT[A/T]AANAAAGTTCAC
AAAGACGAAACAGGTATAAAATGTTTTGTTATGTGAGAATTCCTATAC

MARKER 16:
CAGCATGGGAAGGACTAGAATGTGTCTGACATGTCCTTCAAGGTATTTTTTCAGTTGTTC[A/T]TTGCAGGTTTTA
TTACTGTACAGAGCATGATGATACATAATTAGAAGATTGGTTNTATCT

MARKER 17:
ATTCATAGCGTAATCTGTTAATCCGTATGCCCATCAATGTTGTTTGTAGTTCAGGATGTT[T/C]GGATGGATACTC
ACAGTCTTTGGCCTATTTGNTATTATTGTACTTGGAAGCTTGTTTATA

MARKER 18:
AGAACTATTGAAGAAATCAGTACATCTCCACATCCCTTTTTTGAAGAAAAAAAATACACC[T/G]AACAGTTTAAAA
ATGAAAATGGAAGGCATGGAGGAATTCCTAGCTAAAATCTTTAGTTAT

MARKER 19:

Figure 11 Continued

TTTGTCGTTTGATACTTGTATGCAATCAGCTTCAGTAGCCAGCTTCGTATATCTTTCAGA[A/T]GAAAAANATCCT
GATTTGTTACATAGTATTTCGGTATGCACTTGTGACTGATCAGTTTAC

MARKER 20:
TGTCCTNTGATTTCTATCTCCCTGNTTTGTGTAATAAAGAAGTTTGTGTATTTGGCAGAT[T/C]GAGGCAGTAGTG
ACTAAGGCTGAGCTCAAGTATCTTGCTTTCTTGTGCAAGTCTGAGGTT

MARKER 21:
GAAGCTGAAGAAGATTGGCTTTGCATGCTAAGGAAGAGTTTCTGATTATTACCAGGTACA[A/G]CAACTTCTTTCT
TCATGAGTTTCCTCTTGCGTAAAGATACAGAAATTGGAATATTGTCAT

MARKER 22:
GGAAAGCCTACTGTTGTGGAATTCTATGCCGATTGGTGTGAAGTTTGTCGAGAATTAGCT[T/C]CAGATGTCTATA
AAGTTGAACAGCAGTACAAGTAAATCTCTTTTTTGTTATTGACTCCTG

MARKER 23:
TATTACTGGTTANTCGCCATCTATTTGGTTTCAAATGCTTGGCTGCTTAGTTATTACTAA[T/C]TTTTGGTTTTGA
TTACACATAGTGGACTAACTCCTACATGAAGATGAATAGAACAGTTAT

MARKER 24:
GTTGGNTAAAAAAGGCATCCTNTTTTGCCTCCGTTTAGTATCTAAATCTGGAATCATTAT[A/T]ATATCAATTCTA
AAGTTGAGAATTTTATGTTTTGGACTTCTCAAGAAAATATTGATTTTA

MARKER 25:
ATCAAGGGTTTATAACAATAAAAAGGTAATCATCAGAAAATGATGTATAGTTGGAAAAAA[A/G]AACCTTCCAAGA
TGGTGAATCAAAAGCATAAAAAATAGCTTCCTTGAATTCGTCTTTGTA

MARKER 26:
GAATTGGCTTTATGTATTTGGAATCCTTGTATTTACTGTATTTTTCTTTT[T/G]CTCCAATGCAGGGGTCCTAGAT
GG

MARKER 27:
CACTCCCAAGTCTTCCATCACTCCCCCTCTT[C/A]GTAGCTCCAAATCCTCGACTCCCCATAATAACAGCACTAAG
CCCTAACCTC

MARKER 28:
ACTGGAAGATTTCTCGCATGTCAATCTAAGTATGC[G/C]GAACCTTCTGAAGCATTCAATGATATTCTTATAAGAA
ATACCAA[G/A]AGTTTGGATATTCTCTATAGCAAGAATCACACTGAGGT

Figure 12

| | | | CLT Locus | | | | Phenotype of CLT |
|---|---|---|---|---|---|---|---|
| 7-14 | 7-16 | 7-17 | | 7-20 | 7-21 | 7-25 | |
| | | | | LA2133-42-1 | | | tolerant |
| LA2133-42-2 | | | | | | | segregating |
| | | | | LA2133-43-1 | | | segregating |
| LA2133-42-3 | | | | | | | segregating |
| LA2133-43-3 | | | | | | | susceptible |
| LA2133-42-4 | | | | | | | tolerant |

```
                              SEQUENCE LISTING

<160> NUMBER OF SEQ ID NOS: 59

<210> SEQ ID NO 1
<211> LENGTH: 121
<212> TYPE: DNA
<213> ORGANISM: Solanum neorickii

<400> SEQUENCE: 1
gatgagattg ttacatgatt ttgtgcagat ctagcacaag ccttagccaa attaaaggag      60
kcctctccat attcggtccc tctggtcatt ttcggtcaca tgcacaaaca gcttgcttct     120
g                                                                    121

<210> SEQ ID NO 2
<211> LENGTH: 121
<212> TYPE: DNA
<213> ORGANISM: Solanum pennellii

<400> SEQUENCE: 2
ttttcatttt gcgttttctg caggagagtt caaattgaac atcgagtgca accatgccac      60
kttggctggt cacaggtttg tgtgttttca gtgcaaatta actatgtccg tcttttgcac     120
c                                                                    121
```

<210> SEQ ID NO 3
<211> LENGTH: 99
<212> TYPE: DNA
<213> ORGANISM: Solanum neorickii

<400> SEQUENCE: 3
gtcattacta tgtccacaga tgccacagat ctagatcawc cgttactata gccacagatg    60
ccacagatct agatcatatt atccttcttg cattttgtg                            99

<210> SEQ ID NO 4
<211> LENGTH: 121
<212> TYPE: DNA
<213> ORGANISM: Solanum neorickii

<400> SEQUENCE: 4
tagattgcgt ctcctgcgct ccgtactggc tttacttcgt gaatgggcac tttctgtctt    60
ygcacaggga atgggtacaa gtgttactgg agcctctctg attcttggtg aactttatc   120 a                                                                   121

<210> SEQ ID NO 5
<211> LENGTH: 121
<212> TYPE: DNA
<213> ORGANISM: Solanum neorickii
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (101)..(101)
<223> OTHER INFORMATION: n is a, c, g, or t

<400> SEQUENCE: 5
ttatgactta gccaacggga aaacatttaa antggatgtt tttgtatatt tacctccaat    60
waaaccctaa atgaatttca tgactaataa atggttcaaa ncaatgatat tttcatcttt   120
a                                                                   121

<210> SEQ ID NO 6
<211> LENGTH: 121
<212> TYPE: DNA
<213> ORGANISM: Solanum neorickii
<220> FEATURE:
<221> NAME/KEY: misc_feature
<222> LOCATION: (20)..(20)
<223> OTHER INFORMATION: n is a, c, g, or t

<400> SEQUENCE: 6
tgttataccg tgatttatan caaatgattg gacaataagg cctttcacca ttcttgctct    60
ygatgtcagt gtcactgaaa gtaacagtag ttggagtacc cataatattt gatcggatgg   120
a                                                                   121

<210> SEQ ID NO 7
<211> LENGTH: 121
<212> TYPE: DNA
<213> ORGANISM: Solanum neorickii

<400> SEQUENCE: 7
aggtcctcat tgtctgtgtt gctccgccct gcaattgtcc taaatttaac tgaactaatg    60
yatggggaaa aatgaaatgg ggattcgttt gtgcagggag gatttgaatc tggtgcagtg   120

```
                                                        -continued g                                                             121

<210> SEQ ID NO 8
<211> LENGTH: 121
<212> TYPE: DNA
<213> ORGANISM: Solanum neorickii
<220> FEATURE:
<221> NAME/KEY: misc_feature
<222> LOCATION: (115)..(115)
<223> OTHER INFORMATION: n is a, c, g, or t

<400> SEQUENCE: 8
tattttagca gctataatgg tggatacaat tggtcgaaaa ttcagtgtgg cacttatgtg    60
yggtttaagc ttcctgttcc ttttaccgct tcttgcacct caactccctg ctttnactac   120
t                                                             121

<210> SEQ ID NO 9
<211> LENGTH: 121
<212> TYPE: DNA
<213> ORGANISM: Solanum pennellii

<400> SEQUENCE: 9
aaaggtcagg ctattgtttc tttttttgtag tttgtagtag cacaattagg aaccaaatgc   60
rttgtgctac agtagtctta gtacaagctg gtgcaaatat acctgctacc gttatggtcc   120
c                                                             121

<210> SEQ ID NO 10
<211> LENGTH: 121
<212> TYPE: DNA
<213> ORGANISM: Solanum neorickii

<400> SEQUENCE: 10
cgagatgaag agaaccggtg tggctcctaa tgttgtcact tataatacgc tgataaacgc    60
rtatagtcag gttggtaatt ctgaaatggg aagtaggctt ttcgaggaga tggcaaacaa   120
t                                                             121

<210> SEQ ID NO 11
<211> LENGTH: 108
<212> TYPE: DNA
<213> ORGANISM: Solanum neorickii
<220> FEATURE:
<221> NAME/KEY: misc_feature
<222> LOCATION: (3)..(3)
<223> OTHER INFORMATION: n is a, c, g, or t

<400> SEQUENCE: 11
ttngagaatc ttccttctcc agatactcct gcagtatatg tgtccaacca tcagagcttt    60
ytggacatat atacattact tactcttggg agaaacttca agttcatc               108

<210> SEQ ID NO 12
<211> LENGTH: 121
<212> TYPE: DNA
<213> ORGANISM: Solanum neorickii
<220> FEATURE:
<221> NAME/KEY: misc_feature
<222> LOCATION: (49)..(49)
<223> OTHER INFORMATION: n is a, c, g, or t

<400> SEQUENCE: 12
tttcaagaac cttagtgatg ttagccctat taataccttg gctggaggna acttatactc    60
kttgaacttc accgatgact ctgggaccgt tcatcttaac tcaggatggt ctaggactaa   120
``` a                                                                        121

<210> SEQ ID NO 13
<211> LENGTH: 121
<212> TYPE: DNA
<213> ORGANISM: Solanum neorickii

<400> SEQUENCE: 13
ggctggcttc gccagccatg acggagttgg aaatggtagt catggactgg cttgctaata      60
ygttgaaatt accaaaaact ttcatgtttt ctggcacggg tggtggtgta ctacaaagta     120
c                                                                        121

<210> SEQ ID NO 14
<211> LENGTH: 121
<212> TYPE: DNA
<213> ORGANISM: Solanum neorickii

<400> SEQUENCE: 14
acttgtgttt aaattgcaga tgtcatcaga tggaccaacc cacaatgagt ttgattttga      60 rttttaggc aatacaactg gtgaaccata tacagtacaa acaaatgtgt atgtcaatgg      120
t                                                                        121

<210> SEQ ID NO 15
<211> LENGTH: 121
<212> TYPE: DNA
<213> ORGANISM: Solanum neorickii
<220> FEATURE:
<221> NAME/KEY: misc_feature
<222> LOCATION: (64)..(64)
<223> OTHER INFORMATION: n is a, c, g, or t

<400> SEQUENCE: 15
tcaactaaag aaagaactgc aactgaactc ccttcaaact gacacgatta aatgcctgct      60
waanaaagtt cacaaagacg aaacaggtat aaaatgtttt gttatgtgag aattcctata     120
c                                                                        121

<210> SEQ ID NO 16
<211> LENGTH: 121
<212> TYPE: DNA
<213> ORGANISM: Solanum neorickii
<220> FEATURE:
<221> NAME/KEY: misc_feature
<222> LOCATION: (116)..(116)
<223> OTHER INFORMATION: n is a, c, g, or t

<400> SEQUENCE: 16
cagcatggga aggactagaa tgtgtctgac atgtccttca aggtattttt tcagttgttc      60
wttgcaggtt ttattactgt acagagcatg atgatacata attagaagat tggttntatc     120
t                                                                        121

<210> SEQ ID NO 17
<211> LENGTH: 121
<212> TYPE: DNA
<213> ORGANISM: Solanum neorickii
<220> FEATURE:
<221> NAME/KEY: misc_feature
<222> LOCATION: (93)..(93)
<223> OTHER INFORMATION: n is a, c, g, or t

<400> SEQUENCE: 17

```
attcatagcg taatctgtta atccgtatgc ccatcaatgt tgtttgtagt tcaggatgtt    60
yggatggata ctcacagtct ttggcctatt tgntattatt gtacttggaa gcttgtttat  120
a                                                                  121

<210> SEQ ID NO 18
<211> LENGTH: 121
<212> TYPE: DNA
<213> ORGANISM: Solanum neorickii

<400> SEQUENCE: 18
agaactattg aagaaatcag tacatctcca catcccttttt ttgaagaaaa aaaatacacc   60
kaacagttta aaaatgaaaa tggaaggcat ggaggaattc ctagctaaaa tctttagtta  120
t                                                                  121

<210> SEQ ID NO 19
<211> LENGTH: 121
<212> TYPE: DNA
<213> ORGANISM: Solanum pennellii
<220> FEATURE:
<221> NAME/KEY: misc_feature
<222> LOCATION: (68)..(68)
<223> OTHER INFORMATION: n is a, c, g, or t

<400> SEQUENCE: 19
tttgtcgttt gatacttgta tgcaatcagc ttcagtagcc agcttcgtat atctttcaga   60
wgaaaaanat cctgatttgt tacatagtat ttcggtatgc acttgtgact gatcagttta  120
c                                                                  121

<210> SEQ ID NO 20
<211> LENGTH: 121
<212> TYPE: DNA
<213> ORGANISM: Solanum neorickii
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 20
tgtcctntga tttctatctc cctgnttttgt gtaataaaga agtttgtgta tttggcagat   60 yaggcagta gtgactaagg ctgagctcaa gtatcttgct ttcttgtgca agtctgaggt   120
t                                                                  121

<210> SEQ ID NO 21
<211> LENGTH: 121
<212> TYPE: DNA
<213> ORGANISM: Solanum neorickii

<400> SEQUENCE: 21
gaagctgaag aagattggct ttgcatgcta aggaagagtt tctgattatt accaggtaca   60
rcaacttctt tcttcatgag tttcctcttg cgtaaagata cagaaattgg aatattgtca  120
t                                                                  121

<210> SEQ ID NO 22
<211> LENGTH: 121
<212> TYPE: DNA
<213> ORGANISM: Solanum neorickii
```

```
<400> SEQUENCE: 22
ggaaagccta ctgttgtgga attctatgcc gattggtgtg aagtttgtcg agaattagct    60
ycagatgtct ataaagttga acagcagtac aagtaaatct cttttttgtt attgactcct   120
g                                                                   121

<210> SEQ ID NO 23
<211> LENGTH: 121
<212> TYPE: DNA
<213> ORGANISM: Solanum neorickii
<220> FEATURE:
<221> NAME/KEY: misc_feature
<222> LOCATION: (13)..(13)
<223> OTHER INFORMATION: n is a, c, g, or t

<400> SEQUENCE: 23
tattactggt tantcgccat ctatttggtt tcaaatgctt ggctgcttag ttattactaa    60
yttttggttt tgattacaca tagtggacta actcctacat gaagatgaat agaacagtta   120
t                                                                   121

<210> SEQ ID NO 24
<211> LENGTH: 121
<212> TYPE: DNA
<213> ORGANISM: Solanum pennillii
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 24
gttggntaaa aaaggcatcc tnttttgcct ccgtttagta tctaaatctg gaatcattat    60
watatcaatt ctaaagttga gaattttatg ttttggactt ctcaagaaaa tattgatttt   120
a                                                                   121

<210> SEQ ID NO 25
<211> LENGTH: 121
<212> TYPE: DNA
<213> ORGANISM: Solanum neorickii

<400> SEQUENCE: 25
atcaagggtt tataacaata aaaggtaat catcagaaaa tgatgtatag ttggaaaaaa     60
raaccttcca agatggtgaa tcaaaagcat aaaaaatagc ttccttgaat tcgtctttgt   120
a                                                                   121

<210> SEQ ID NO 26
<211> LENGTH: 75
<212> TYPE: DNA
<213> ORGANISM: Solanum neorickii

<400> SEQUENCE: 26
gaattggctt tatgtatttg gaatccttgt atttactgta ttttctttt kctccaatgc    60 aggggtccta gatgg                                                    75

<210> SEQ ID NO 27
<211> LENGTH: 83
<212> TYPE: DNA
```

<213> ORGANISM: Solanum neorickii

<400> SEQUENCE: 27
cactcccaag tcttccatca ctcccctct tmgtagctcc aaatcctcga ctccccataa     60
taacagcact aagccctaac ctc                                           83

<210> SEQ ID NO 28
<211> LENGTH: 119
<212> TYPE: DNA
<213> ORGANISM: Solanum neorickii

<400> SEQUENCE: 28
actggaagat ttctcgcatg tcaatctaag tatgcsgaac cttctgaagc attcaatgat     60
attcttataa gaaataccaa ragtttggat attctctata gcaagaatca cactgaggt    119

<210> SEQ ID NO 29
<211> LENGTH: 30
<212> TYPE: DNA
<213> ORGANISM: artificial
<220> FEATURE:
<223> OTHER INFORMATION: PCR primer

<400> SEQUENCE: 29
gaattggctt tatgtatttg gaatccttgt                                     30

<210> SEQ ID NO 30
<211> LENGTH: 20
<212> TYPE: DNA
<213> ORGANISM: artificial
<220> FEATURE:
<223> OTHER INFORMATION: PCR primer

<400> SEQUENCE: 30
cccatctagg acccctgcat                                                20

<210> SEQ ID NO 31
<211> LENGTH: 25
<212> TYPE: DNA
<213> ORGANISM: Solanum lycopersicum

<400> SEQUENCE: 31
tttactgtat ttttcttttt ctcca                                          25

<210> SEQ ID NO 32
<211> LENGTH: 25
<212> TYPE: DNA
<213> ORGANISM: Solanum neorickii

<400> SEQUENCE: 32
tttactgtat ttttcttttg ctcca                                          25

<210> SEQ ID NO 33
<211> LENGTH: 572
<212> TYPE: DNA
<213> ORGANISM: Solanum lycopersicum

<400> SEQUENCE: 33
tgcatgcttt ctcagtggag gctaccaagg cagagtcttg ggacgacgaa gttgatcatc     60
tgaaattcta ttataatgga aaagagttag gcttaccaga aggatatcca tccatatggg    120
aatcttctga aagcggcatc aaggtagaaa gaactgcaaa caagaacggt gctttttatca   180 cactaccaga agtagcagaa atttcagtaa atgtagtacc tattaccaag gaagatgaca    240

```
ggatccacaa ctatcagtta ccttctgatg actgcttcgc tcacctggac gtgcagttca    300
gattctatgg cctctcaacg aaggttgaag gcgttcttgg ccggacgtac cagccagact    360
tcaaaaatcc agcaaaacca ggtgttgcag tgcctgtagt gggaggtgaa aagatgtaca    420
gaacttcaac cctttgtct tccaaatgta actcctgtat cttctctcca gctggagttt     480
ctgaagaatc agaccccta gtcatggatt atgggacttt agattgtact ggaggatcaa     540
gcggtggcca cggaataatt tgcagaaaat ga                                  572
```

<210> SEQ ID NO 34
<211> LENGTH: 2433
<212> TYPE: DNA
<213> ORGANISM: Solanum lycopersicum

<400> SEQUENCE: 34

```
atggaaatcc caaattcagg gggttcagtc tcaaggagac ctgtgagaag gaggttcgct     60
tctaggaatt atgatgagac tgtgatggat aaaatcatag atgagcagtt gggtagtccg    120
gtggggaaga agattagaac gaagaaagat ttggagaaag aaactgaaaa agaggccttg    180
attgctcttt ctttgggctt cccaattgat gaccttcttg aagaagaaaa aaaggctgga    240
gttgtaagtg aattggatgg gaaagagcaa aacgattaca tcgttgtgag aaatcatatt    300
ctcgcaaaat ggagggagaa tgtgcatatt tggctgaaca aggaaggat aagggaaatt    360 ataagtgtcg agtatgaaca tttggtagcc atagcatatg attttctttt aagtaacggg    420
tatataaatt tcggggtttc atcatcattt gaatctaatc ttcctgagga acctagagaa    480
gggtctgtaa ttatcattgg tgctggactc gctggtttgg ctgcagcaag gcaactgatg    540
gcttttggat ttaaggtaac tgtccttgaa ggtaggaacc gacctggagg gagagtttat    600
tctgagaaaa tgggatggaa gggaaagttt gctgctgtgg atcttggtgg cagcgttata    660
actggtatcc atgcgaatcc tttgggagtt ttggctagac aactttccat tccgcttcac    720
agtgttagag ataagtgtcc tttatacaag cctgatggtg ctcctgttga ttcagtagtt    780
gattccacag ttgaactcat tttcaataag ctactagaca aagttgctga actacgaaaa    840
atcgtaagtg gattggctac tgatgtctcg ttaggctccg ttttggagac acttagacga    900
ttatattgtg tggctaaaac taaagaggag aagcaacttc tgcattggca ttttgcaaac    960
ttggaatatg caaatgctgg atgcctctcg gaactctctg ctgcctactg ggatcaggac   1020
gatccttatg aaatggatgg tgatcattgt tttcttgttg gtggaaatcg agctatgatc   1080
agggcattgt gtaaaggagt tcctatattc tatggaaaga ctgttcagac aattaagtat   1140
ggaaatgaag gagttgaggt cattgctggg gaccaacttt ttcaggcaga catggtccta   1200
tgtactgttc ctcttggggt actaaaaaga agatcaatta gatttgaacc agagttacct   1260
gagaagaagc ttgaagctat tgataggcta ggatttgggt tgctgaataa agttgccatg   1320
gtatttcctc atattttttg gggcgaagac ttggatacct tcggttgcct caaccatcat   1380
agccacagac gaggagagta cttcttattt tacagttacc atactgtttc tgggggtcca   1440
gtacttattg cacttgttgc tggtgacgct gctcaacttt tcgaaagcac agatccgtcc   1500
actttaatta atcgagtgat taacattctc aaaggcattt atgagcaaaa gggaataagc   1560
gtgcctgatc ctatacaatc catatgcaca aaatggggaa gtgatcccct ttcgtttggc   1620
tcatattcac atgttcgtgt tcagtcatct ggcagtgatt atgacatact tgcagaaaat   1680
ctcggaggtc ggttgttttt tgctggagag gctacgattc gacaacatcc agccaccatg   1740
```

| | |
|---|---|
| catggagcct atttgagtgg cttaagagaa gcttctcaca tttcccaatc catgaaagcg | 1800 |
| aggcaaaaca atccaaggag aactgtatca aagaatgttc gaccaagcaa tgatacattg | 1860 |
| gaagagttgt ttgaaaagcc agatctagca ttcgggaagt tgttatttgt atttgatccc | 1920 |
| ctcacttgtg attctaattc tttaggactg atgagagtta cttttggaaa atccaacgac | 1980 |
| gagcttaatt cagaagaggt agacaatatg cctcaacatt tattaaatcc atcactgcag | 2040 |
| ctttatacag ttgtgtctcg tgagcaagca catgagctgc agttggtgaa ggagggaaac | 2100 |
| aattgcaaat tgttagattt gcttgaaggt cttgggttaa gttagtgggg agcgaatgga | 2160 |
| ctaggagttc aaggccatac tttggctgct aaaattgtta aaggtagaag gagtcgaagc | 2220 |
| tatactgcca agcagaaggc aggcgaaagt agcagtcagt atatattgtg catctggcag | 2280 |
| cagagtgtga aaaaggatc gatgaacgcg cgttttgcat ctggtttggg agtttcaagc | 2340 |
| cttcctactc tgtgctgttg tttatgttgt ggatatttt ctatatgctt gtgctttgta | 2400 |
| ctcctagata gtgcaaactt tcttgtaggc taa | 2433 |

<210> SEQ ID NO 35
<211> LENGTH: 1461
<212> TYPE: DNA
<213> ORGANISM: Solanum lycopersicum

<400> SEQUENCE: 35

| | |
|---|---|
| atggcggtct tatgctgcgc cacctctgct tatcctacgc atactctgag agtaacttct | 60 |
| gctaaagctg cagtgcgttc gagctctcga gtttcagttc ctcagctgca tcattccgat | 120 |
| tccccgtttg ttcccgaggt taataaggct gttgattctt tgtcaaaaga gttcagagaa | 180 |
| gttgacaatt tagtggcacg caatactgcg cgagttttga gagcttttcca aagggtcaag | 240 |
| gttgggtctc atcactttgg tggtagcact ggctatggtc atgaagaagc tggtgggcgt | 300 |
| gaagccttgg accaggcttt tgcagaaatt gttggtgcgg agtctgcaat tgttcgatca | 360 |
| cagttcttct caggtactca tgcaatcact tgtgccttat tcgctttctt aaggccaggg | 420 |
| gatgagttgt tagcgatagc tggtgcacct tatgatactc tggaggaagt aattggaaaa | 480 |
| agggactctg tgggattcgg ttccttgaaa gattttggag tagaataccg ggaagtccca | 540 |
| cttgcagagg atggcgggct tgattgggat gcacttaaaa cctctataag acctcacact | 600 |
| aagtgtgcac tcatacagag atcatgtggt tattcttggc gtcgcagttt gagtgtcact | 660 |
| gagataggtc gagcaattga tataatcaag atgcagaacc caggctgcat ggtcatggta | 720 |
| gataactgct atggtgaatt tgttgacgac atcgaacctc ctatggtggg tgctgaccta | 780 |
| attgccggaa gtttgattaa aaatccgggt ggaacgattg caccatgtgg tggatatgtt | 840 |
| gcggaagga aaaaatgggt agaagcagca gctgcccgtc tctcggcccc aggacttgga | 900 |
| gttgattgcg gttctacccc tggtgatata atgagaactt tatttcaggg tttattcctc | 960 |
| tcacctcaaa tggttggtga agcaataaag ggaagcttcc tgatagctga agtcatggcg | 1020 |
| gctaaaggtt ataaagtgca gccactttgc cggatcaagc gtcatgacac agtgcaggct | 1080 |
| gtacaacttg gaaatcgtga gaatctactt tcctttttgcg aggctgttca gagaagttct | 1140 |
| cctgtcagct cttttatcag gcctgttgca ggtgcaactg ctggctatgc atctgaggta | 1200 |
| attttgctg atggaacctt cattgatgga agtactagcg agctctcatg tgatggacca | 1260 |
| ctaagagagc ctttctctgt tttctgtcag ggtggcactc attggacgca gtggggacta | 1320 |
| gttctggggg agaaactggg gccggcaact gtgggccctc cgagtaagtc ggatcggcac | 1380 |
| gtgcatgagc atgtggttcg gtgccacgtg ttaaatgttc ttctagatat tgggcccact | 1440 | atctccaggc tcagccaata g                                            1461

<210> SEQ ID NO 36
<211> LENGTH: 900
<212> TYPE: DNA
<213> ORGANISM: Solanum lycopersicum

<400> SEQUENCE: 36

| | |
|---|---|
| atggaattgg atctggatcg tgggcaagtc acactgatag catccagtat atgtcttatg | 60 |
| ctgactttac atttcagcat acagctagtg acagaacatt ttacgtcatg gaagaagcct | 120 |
| aaagagcaaa aggccataat tattatcgtc ctcatggcac ctttgtatgc tattgtctcc | 180 |
| ttcattgggt tggtcgattt catgggaagc aaacccttt tcactttctt ggaatctgtc | 240 |
| aaagaatgtt atgaagcaat tgtgatggct aagttcctgg ggttgatgta cacttacttg | 300 |
| aatatatcca taagcaaaaa catagtccct gatgaaatta agggaagaca gattcaccac | 360 |
| tcattcccaa tgacactctt ccagcctcac actgctcatt tgaaccatca tacattgaag | 420 |
| cttctcaaga actggacatg gcagtttgtt gtgattcgcc ctgtatgctc tattttaatg | 480 |
| attgttttac aaatgtttgg agtgtaccct agttgggtta gctggacctt taccatcatt | 540 |
| ttaaacatat ccgtttcact ggcattgtac tctcttgtgg ttttctacca cgtgtttgcg | 600 |
| aaggagttgg cgcctcacaa gccactagcc aagttcctgt gtgtcaaagg aattgtcttt | 660 |
| ttcgtcttct ggcagggcat tctgcttagt gttctggtat cactaggcat aataaaatct | 720 |
| cactatttct ggcttgaggt ggagcgcctt caggaaggta tgcagaatga actagtgatc | 780 |
| ctggagatgg ttttcttcgc tatccttatg cgtcatgcat acagtgcagc gccatatcgc | 840 |
| gcagaagctg ttacaactac ttcagaagat gctacttctg gagataaaaa gaatgagtga | 900 |

<210> SEQ ID NO 37
<211> LENGTH: 762
<212> TYPE: DNA
<213> ORGANISM: Solanum lycopersicum

<400> SEQUENCE: 37

| | |
|---|---|
| atgacagcac tcgctcaaat tctcattaat ttatcaccct taaaaacacc acatgatgct | 60 |
| ttgtatagaa aaccgaactt tcttgggctg aaattacagc gacccagttg ttgtttcact | 120 |
| aatttaaggg caagaaaagt gtcaatttgt agtagttggt ataaattagg tgcttttaag | 180 |
| gagaaaaact caatcttgac agataaaaat gggattttta tgaaggagga gagatggggt | 240 |
| tgtgagaaaa gaatggtttt tgtgaaattt aaacaaggtt ttggattgga tgggattggt | 300 |
| gatggtgggg gtggtgggag ggataatagt gagactgtga gagtgttgag taatcttgtt | 360 |
| ttagcaattg gcttactta tcttactatg actggtcagc taggttggat cttggatgct | 420 |
| attgtttctg tttggctcct tgcagttcta cttccaattt taggtttggg agcttttatt | 480 |
| tggtgggctg gacgagatat tgttcaaagc gcttgcccaa actgcgggaa tgaatttcaa | 540 |
| attttcaagt ctactttaaa tgatgaggtt cagctttgcc ctttctgtac tcagccattc | 600 |
| tcagttgttg gcaataagtt cgtgagagac ccagtaacgt tctccaacca gtcaactaca | 660 |
| tttggtcaag catttggtga tttcagtact cgttctaaga aagtaagaa ttcctctgtc | 720 |
| ggaattgttg atatagaagc agaagttaag gacgcggact ag | 762 |

<210> SEQ ID NO 38
<211> LENGTH: 312
<212> TYPE: DNA

<213> ORGANISM: Solanum lycopersicum

<400> SEQUENCE: 38

```
atggcggcgt ggacggcggc ggcgaggcaa gcagcgaacc tatatcgatt ctcagcttct      60
aaatcagtta gctcaacgaa gcaaggcgct ttacttatcc agcggcgcgg ccttgccggc     120
ggtggtgatc atcatggacc tccaaaggtg aattttttggc aggatccgat gagtccgtct    180
aaatggaaag aagagcattt tgtgatcgtc tctcttactg gttgggggtt ggccttctat     240
ggaggttata agctcttcac aaagggaaag aagaggaga aggaagagaa agttggtgaa      300
ggatcccact aa                                                         312
```

<210> SEQ ID NO 39
<211> LENGTH: 1428
<212> TYPE: DNA
<213> ORGANISM: Solanum lycopersicum

<400> SEQUENCE: 39

```
atgaatgaga aggctaatgt tactaaagag cttaatgcga agcatagaaa gatactagaa      60
ggacttctta agttgcccga gaacagggaa tgtgcagatt gcaaagccaa gggtcctaga    120
tgggcaagcg tgaacctggg aatatttata tgcatgcaat gctctgggat ccacagaagc    180
ctggggggtgc acatatcaaa ggtcagatca gctacactag acacatggct tcctgaacaa    240
gttgcattta tccattcaat gggaaatgag aggtcaaata gttttgggga agcagagctg    300
cctccaaatt atgatagagt tggtattgag aatttcatcc gagcaaaata tgaagagaag    360
aggtgggtcc ctaaggatgg gattcaaaaa tcaccttcca gggttcaaga agagagggct    420
tcggtgcaat ggcaacaaaa caatgataga agtgggcgta tacatgcagc tagctcagga    480
tgtgcatctg acgagaggaa aaatattcaa gcctcgaaag tgaagcaaga tgtacctgct    540
gctagagtca gtataccagt gcctcctaga ggaccagagc atgtaacttc aggtcaggtt    600
gctaaccaga caagtcagaa agcagagcca gttgcagtca ctgaaccagc taagcaggtt    660
ccggaagctg ccagtcctcc taaagttgat tatgctactg atctatttga catgctttct    720
atggattgtc caactgacaa tggctcagaa gcagcttcta ccgatgataa ctcctgggca    780
ggcttccagt ctgctcaaga agcaacaaaa gcagaaaata ctggggttac aaaactccgtt  840
gatcagaaga agtctcaatc tgctgctgct tctggaattg aagatttatt caaggattta    900
ccatcaattg tgccttctgc ctcatcgcag aagccacaga aagatgctaa aaacgatata    960
atgagccttt tcgacaagtc caatattgtg tcaccttttg ctatgcatca acaacaactt   1020
gctatgctgg cgcaacaaca gtctttactg atggctgcgg ctgctgcagg tggtgctgta   1080
agacttcctg taaatgcaca acaaagcact aatggcacca atatggtaaa tcagaactgg   1140
ccaaatttag gctatcagtt ccctggagtg ataatgccag cagctggtaa gactgagctg   1200
gagaaatata tgcaggtagg caatatggga ccagcacatg tagttggaaa ctctgtgcca   1260
attccagcat ccagcttcta ctcaatggga cagaacactt ccagcaacgg tattgtgccg   1320
ccaggaccaa gcaagcaagc agctaccccg atatcatcaa gctccacaca gtcaacaaaa   1380
gaattcgact tttcatccctt gacacagggt atgttcacaa aacgctga               1428
```

<210> SEQ ID NO 40
<211> LENGTH: 1092
<212> TYPE: DNA
<213> ORGANISM: Solanum lycopersicum

<400> SEQUENCE: 40

```
atggcgattt tgtttcaaag ttcaagtagc tccatgttat ctatcaaagt ttttctgatt      60
tcgactactg tttttatctgc tgctattatg ttaaaggtgt ctgctcctgt tgttactgaa     120
ttcgcggtca gtgaagttcc gtcgatctgg aacggtgtcg tttcgtggct taaacctccg     180
tatctatacc ttgttatcaa ctgcattatc attacgattg tagcctcttc taagttgcag     240
aacaagcttg atgagaactc atctccggtg ccggcggttg tttcgccgga gaactcgtcc     300
cagtttcacc cgattaagga tgtaaggccg gttacagact attatacacc ggtccttcat     360
gacttaaacg gctccgtgct gaagaatcaa gcagtggagg cggaggctag accgatagtt     420
tacgagtatc ctactgctgg tgtttatgat gcaaaggtcg agaaacttcc agtagttaat     480
ccgtacatat cggagaaagg tacatcgttc aacacctatc cggagcctaa cgatgttgtt     540
gctgaaaagg atgatttcgt aatctcgaaa tcttcttggg cgccggtgat gagacaggac     600
tctattgatt attccatttc aggcaactcg gctgagaaac ctcctgcttc tgccagattc     660
gctcaccgga gaaatgtcaa atccactcct gaaggtggaa agggagcatt gagagtatca     720
aaacctaaac ggcaagacac gctggagagt acatggaaga cgataacgga gggccgtgca     780
atgccactaa cgaggcacct gaggaaatcg gacacgtggg agacatacgg tggtcggaac     840
ccggttacac caccaccgca gaagatgaag aaatctgaga cgttcaatga cagaactacc     900
cctgactcct cgccattgct gactccgtcc ccgggtggtt cagggaaact taagaaagag     960
ccatcgctaa gtcaagacga gctgaacagg cgagttgaag cgtttattaa gaagtttaat    1020
gaagatatga ggttgcagag gcagcagtcg atgcaacagt acactcagat gatcaatcga    1080
ggctcacatt ag                                                         1092
```

<210> SEQ ID NO 41
<211> LENGTH: 1149
<212> TYPE: DNA
<213> ORGANISM: Solanum lycopersicum

<400> SEQUENCE: 41

```
atggcgctcc agcactcgcc tattggcaca attacttctt cagctcaaat gaagctggct      60
gttagcagtt tgaggtgcta cgagcacctt cgtcctatca ctatctcaag cttcaagcgt     120
tttccacgaa gaattcaggg tgcgcatagt agtgtggagc aaaggaagtt gcttagcaga     180
ggtatttcga caagcaaaga aaatcgaag gatctccatg aagatgtttt ttctttgcca     240
atggcttgca ctagtgcccc aattagattc acaatgctct caactgctgt catagccaca     300
aatttggttg caacacatac cgcaaatgct ttgactatgg ataacatgat ggatttctct     360
agcgctgtct atacattagc tgatggaagc attggagatc ttttggtgg ccttctgtat     420
tctgctggtc aacaagctaa tgaagctgtt cagggccagt tgactgctct tagtttact     480
agtttggcca ctattttggg tgccgggctt gtaactagtc tgtcgccttg tacactcagc     540
gtactgcctc tgacccttgg ttatattggg cttttggtt ctgggaaaag ccgagtagcg     600
gttgttggag attcaattgc atttgcactg ggattggcaa ccacactagc attattgggt     660
attgcggctg catttgctgg aaaggcatat ggacaaatag acaaggatt gcccgtggct     720
gcttcctttt tagctattgt tatggggcta aacctgttag aggtaataga gttgcaactt     780
ccctcatttt ttgacaactt tgatcctcgc tcagccgctg ctagcttttcc gtccagtgtt     840
caagcttatt tggccggtct tacatttgca ttagctgcat caccatgcag tacaccagtc     900
ctcgcaacct tgctcggcta tgttgctact tctcgggatc cagttattgg gggcagcttg     960
```

```
ctattgacat acacaactgg ctatgttact cccttacttc ttgctgcttc ttttgctgga    1020
gcattgcaga gtatactttc attccgcaag ttctcagcat ggatcaatcc aatcagtggt    1080
gcgctactac taggaggggg tgtctatacc tttctcgaca agcttttttcc ggtgacgatg    1140 gctatgtag                                                            1149

<210> SEQ ID NO 42
<211> LENGTH: 294
<212> TYPE: DNA
<213> ORGANISM: Solanum lycopersicum

<400> SEQUENCE: 42
atggcgaaga acagaaacaa gaagaaaaac ggcctagctg ccatggatgt ctccactgac      60
cagacggtca tggatgccca agcgatggat acttcagaat cagctgctcc aaaaccacat     120
ataggtggat cacttagaaa gacgaaggga gtacaaatga aaggacgaa gaatgttagg      180 aaaaagaagg ccatggcaaa ggctatttca aaagtgaga aattggagga agaatcact       240 aggagtgaaa gcaagataga gagaactaaa atgccaaac agttatacga atga            294

<210> SEQ ID NO 43
<211> LENGTH: 3048
<212> TYPE: DNA
<213> ORGANISM: Solanum lycopersicum

<400> SEQUENCE: 43
atggattttg atgtccaggg gggaaaaatg tctactatag ttcgtagttc gttagaggaa      60
atgctggatt ctctccggca aagggatgaa atgagaagc caaaagactt gccgccggcg      120
ttgcctgctc ggcctaagct tacatcgagg actaggcctc cttcacagag gcaaccgttg     180
agcaaaaggt taagcaaagg tgatgttgaa ttggagaatg gtaagaagaa ggaggagttg     240
aaagtgttga aaaggaatgt ttttggtgct atgaaggtga aaggaatcga agatagcgaa     300
tcgccatatg caatgccttc agtgaagaaa acagcacag ggagattgcg ggaagtaaat      360
ggtgggaagg ttgagaaatg gcgtagtgaa gctgaatggg atgatcggct ggattatttt     420
gttaagaaga agcttcgcat ctggtgtcgt ctggggaatg gggcatgggt atcaggacat     480
attcaatcaa cttcaggagg gaaagctatg gtgttgctttt ctgacggcag tgttgtgaca    540
gtgcctgtag gagaggtatt accttctaat ccggatgttc ttgagggtgt ggatgatctc    600
atgcagctta gttatttgaa cgagccatct gttcttcaca accttcaaca cagatatgcg    660
cgagatatga tatatagcaa ggcagggcct gtattaatag caatcaatcc gttcaaagat    720
atccaattgt atggaaacga atttgttaca gcttacagac agaagctctt gagtgatcct    780 catgttttact ctattgctga ttctgcctac gatcgaatga tggaagatga gataagtcaa    840
tctattatca taagtgggga aagtggatct gggaagacgg aaacagcaaa atttgcaatg    900
gaatacttgg ctatgcttgg tggaggtagt aatgggatag agaaggaggt tttgcaaaca    960
agctacatat tggaggcctt tgggaatgcc aaaacttcca ggaacaataa ctccagtcga   1020
tttggaaagt tggttgaaat tcattttagt ccagcaggaa gaatatgtgg tgctaaaata   1080
caaacctgta gtgtaattg tcctttgtcg agagtggttc agctgcttga tggagagagg   1140
tcctatcata tttttttacca actatgtgcc ggggctccac ctactttgag agataaactt   1200
aagttaaaag gtgcatcaga atacaaatat ctcaaccaga gtggctgctt ggtgatccat   1260
gatgttgatg atgctgagga atttgtaag cttatggaag ccttaaatac tgttaggatt   1320
tctgaaaggg atcaagagca tgcttttcag atgattgctt cagttctatg gctgggaaac   1380
```
ataacattcc aagtaattga cgatgaaagt cgtgctgaag ttgtgcaaag tgaagctgtt    1440
acaaatgctg ctagcttgat tggctgtact gtaaatgacc tcatactagc tttgtcaaca    1500
tgccaaatac gagctggcaa ggataagatc gccaagagtt aactgtaga gcaggcaact     1560 gatagaagag atgcattggc aaagttcatt tatgcaaact tgtttgactg atagtagat     1620 caaatgaaca gaaaccttgc aatggacaaa gaacagatgg gtagatccat aaatattcta    1680
gacatttacg gttttgaatc atttcaggga aactcatttg aacaatttct gataaactat    1740
gcaaatgaga ggctccagca gcatgccaac agacatctat tgaagctcga gcaagaggaa   1800
tatgaattgg atggaattga ttggtcaaaa gtagatttcg aagacaacca agagtgcctg    1860 aaccttttg aaaaggtatt cttccttttg gttcttttc ctatttatat ggcgttagga      1920
gcttatataa gccgacaact ttcttctgcc ccggatagca tgtttacatt caagccaatt    1980
ggccttatat ctttgttgaa tgaagaatca aattcccta cagccacaga tttgacctt      2040 gtatgtaaac ttaagcagca catcaaatct agcccttgct ttaaaagtga agagaagaa     2100 ttttgtatcc gtcattatgc tggagaggtc agtttctctt ataaatgcat ccttctagt    2160 tctgtgcaat ttctacggat attattagta ttttcactat tttggttaag agacttgata    2220
gctttcacat ccccatggtc agacttacgc tcaattgttg ggagagtttt tctttcttat    2280
catggtttta ttacagtaac ttatgatgca actggcttct tagcaaagaa cagagatgtg    2340
ttgcatcctg acattactca gctactctca tcaagtgaca gtcacctgcc tgaagataaa    2400
aaattatcaa ttccatcaac tgatgcagga gtgctagatt ttcagaagca aagtgttgca    2460
actaagttta aggataattt gttcaaattg atgcagcaat tggaaaatac cataccacat    2520
ttcatatgtt gcataaaacc aaataataag cagcttcctg gcatgtctga caaagatctt    2580
gtcatagaac aactcagatg ctgcggtgtt cttgaggtgg ttagaatatc aagatctggc    2640
tatcctacta ggttaacaca tcaagaattc acaagcaggt acggcttcct tctgccaaag    2700
gatagtgcat gccaagatcc tttaagtatg tcagttgcca ttcttcatca atttggtatt    2760
cttccggaac tgtaccaagt tgggtatacc aagttatatt tccgatcagg acagattgct    2820
tcattggagg atgcaaggaa ccaagttctg caaggtactc ttgagttgca gaagtgcttc    2880
cgtggtcatc gtgctcgtcg gcacttccat gaactgaaag gaggagtaat catacttcaa    2940
tcatgtaaag cagatcccttt tgcaactcgt ctcttttctt ccctttttc gttgaatata    3000 atagaagatg atattcatga agattgttgt gtctatcagg ttggatga              3048

<210> SEQ ID NO 44
<211> LENGTH: 843
<212> TYPE: DNA
<213> ORGANISM: Solanum lycopersicum

<400> SEQUENCE: 44
atgtctaaag cgaaggttgc tcgtgaagga agtgatgagc aactggtggc tgtcgtgcag      60
atacaatcag ctattcgtgg ttggttggct agaagggggtc ttcgcaaact gcgaaattca    120
aaaatgttaa atgtagacaa acgaagatca ggcagaaaga cggaggtcaa ggagttgcct    180
cgagaaatcc taccatctgt tgtagaagac ctcgaaagac gggttgcaaa ggccgaggca    240
acaactgaac aaaaggaaaa ggaaaatgct gccctgaagg aacaagtaaa ccaattcgag    300
accagatgct tagaatatga ggtcaagatg aggtcaatgg aggagatgtg gcaaaagcaa    360
atgacatcat tgcaggttag tctagctgca gccaggaaca gtcttaccgc tgctgacact    420

```
actggtcgac ctggaaagct tgaaggttcc ccatctcctc agtattatga ttctgatgat    480
gcaacatcta tggacactcc tgcgggacgc actccagtta gcttttctaa caacagcttg    540
ggtgttgtag ctaatagaga ggttaatggt ggtttatcct taatcagcca ccttgcaatg    600
gaatttgagc aacggaagca aaattttgac aacgaagcca tggcaattgt tcacttgaag    660
ccagggcagt tacagtctac taataatcct gcagatgagt atcgaagact gaaacacagg    720
tttgaggaat ggaaaaaaga gtacaaggtt cggttaaagg agacaaagtc aaaagtacac    780
aagcttgttc attctaaagc agggaagagt cgtagaaaat ggtggggtaa aagagcaaa    840 tga    843
```

<210> SEQ ID NO 45
<211> LENGTH: 789
<212> TYPE: DNA
<213> ORGANISM: Solanum lycopersicum

<400> SEQUENCE: 45

```
atggcagcaa caggtagctc agccacagtt gttagagcaa ctccattttt gggccagacc     60
aaatatgcta accccctaag ggatatagtt cctatgggct ctgccagatt caccatgagt    120
aatgatttgt ggtatggacc tgaccgtgtc aagtacttgg gaccattttc tgctcaaact    180
ccttcatact tgactggaga attccctggt gattacggat gggatactgc tggtttatct    240
gctgatcccg aggcctttgc taagaacaga gctcttgagg ttatccatgg agatggggcc    300
atgcttggag ctttttggttg cattacacca gaagttcttg aaaaatgggt aaaagtggac    360
ttcaaagaac cagtatggtt caaagctgga gcccagatct tcagtgaagg tgggctggac    420
tatttgggca acccaaacct tgtccatgct cagagcattc tagcagtatt gggcttccaa    480
gttgtactaa tgggccttgt agaaggtttc agaattaatg gcttcctgg agttggtgaa    540 ggcaacaatc tctacccagg tggacagtac tttgacccat gggcctagc agatgaccca    600 acaactttcg cggaactcaa ggtcaaggaa atcaagaacg gaagattagc tatgttctcc    660
atgtttggat tcttcgttca agctattgtc accggcaaag gcccacttga aaatctattg    720
gatcaccttg acaaccctgt tgctaacaat gcatgggttt acgcaactaa gtttgttcct    780
ggatcttaa    789
```

<210> SEQ ID NO 46
<211> LENGTH: 342
<212> TYPE: DNA
<213> ORGANISM: Solanum lycopersicum

<400> SEQUENCE: 46

```
atgttggaag ggaaagcagt aattggagat acagatatgt tgggaaccat gcaacaagat     60
gcattagatt tagctgcaaa ggcacttgac ttctttgatg tcactgaggc cactgaaatt    120
gcacgttttc ttaaaaagga atttgataca atgtatggac cagggtggca atgcatagta    180
gggacagatt ttggttcatt tgtaacacat tgttatggtt gtttcatcca tttctacatt    240
ggcagccttg ctattttgct cttcaagggc tctgctgccc tagaggaccc gaaagccgag    300
gccgaagctg accgatttttc cactctgcag gaaatagcat ga    342
```

<210> SEQ ID NO 47
<211> LENGTH: 828
<212> TYPE: DNA
<213> ORGANISM: Solanum lycopersicum

<400> SEQUENCE: 47

```
atggggcgcc gtctcttcac ctgcttcggc aaaggcggtt cttctcattc ttcttcaaaa      60
gatcccggct cgaataacaa ggacagtgcg acggcggatt tgacggcgga ggagcaaaaa     120
cggtgcgggc cggtggtggt ggagttattc tcatcgcaag gctgcgccac ctcacctgaa     180
gcggagctgt tgttttcgag gattgggaga ggcgatttta acctagaaat gccggtgatt     240
ttgttggctt atcatgtgga ttattgggat tatatgggtt ggaaggatcc gtttgggtcg     300
agtttatgga cggttaaaca aaaagcgtat gtggagacct aaatctaga taccatgttt     360
acgcctcaaa ttgtggttca gggaagagct caatgtgttg ggaatgaaca agatgcggtt     420
ttctcttgta tcaaatctgc cccagatttt gctgctcctt ccttccaggc aacattcgag     480
aggccaacac cagagtcatt gcaagtatct ctattaggat ctctaaggag taaggtggac     540
aatgatggtg ccaacgtgat gattgctctg tacgaaggtg gtctggtgac tgatatcgct     600
gcaggagaga acaaggaaa atgcttgcg aatgactatg ttgtcaggag gctggaaaag     660
ctttgctatg taaaggatat tactgcaaag aagacaatct caggaactgt caatttctct     720
ctttgggatg gcttcaatag cagcaaatgt ggcgtagcgc tctttgtgga atctggctct     780
catcaaatat gtggatcaca aactttaaa ttgccagaaa atctctga                  828

<210> SEQ ID NO 48
<211> LENGTH: 786
<212> TYPE: DNA
<213> ORGANISM: Solanum lycopersicum

<400> SEQUENCE: 48
atggcaatcg ccgaccacca caagtcacat aactcagacg aaagctctg gaagctttgt       60
cctctatggc aatcaggaac tacgtcttct tcttcgtcgt ctacacaaaa tcttcactct     120
cagaatcaca gtcaccaaaa cggcgtcgga tctaacagct ctcgtgcttc tacgtctgtt     180
agctccgttg ctagatcact gcttccggct agacgtaggc ttcggctcga tccagctaac     240
agtctctact tcccttatga accgggaaag caggtgaaga gtgctgtaaa gattaagaac     300
actagcaaat cttatgttgc atttaagttt caaacgactg caccaaagag ctgctacatg     360
cgacctcccg gaggcattct cgaacccggt gaaagtgtta ttgccactgt cttcaagttt     420
gtggagcacc ctgagaacaa cgaaaagcct gtggaccaaa agagcaaagt taagttcaag     480
atcataagct tgaaggtgaa agaaggtgta gattacgtac ctgagttgtt tgaagaacaa     540
aaggatcacg tgactattga acgtatccta cgggtggtgt tcttggaccc agaacgacct     600
tctccagtgc tggataaact aaagcgtcag ttggctgaag ctgaggcagc attagaatct     660
cgcaagaaac ctccagttga aactggacct aaagttgtag agaaggtct agtaatagat      720
gaatggaagg aacgaaggga gaagtatctc gctcggcagc aggttgaggc tgttgattca     780
gtgtaa                                                                786

<210> SEQ ID NO 49
<211> LENGTH: 300
<212> TYPE: DNA
<213> ORGANISM: Solanum lycopersicum

<400> SEQUENCE: 49
atgaatgcag cagcagcaaa gggatcggca tggatcgtag cagcaagtat ggagcagta       60
gaagcattaa agatcaagg atttgccaga tggaattacg cttaagatc gattcatcac     120
tatgccaaat ctaattaat tgcttctagt aatacctcgg ctcggagatt ctcgacggct     180
```

```
tcggcgccgg cggcgtcttc tccggcagtc gtctccggtg agaagctgag gaaaacggaa    240
gagacgttga gtaaagttat agatctgaac tgttggggtc caagcactgt cagattttag    300
```

<210> SEQ ID NO 50
<211> LENGTH: 2406
<212> TYPE: DNA
<213> ORGANISM: Solanum lycopersicum

<400> SEQUENCE: 50

```
atggagcttc tccgatcaaa ccttgctcgt gttcggattc cagagccgac tactcgtatc     60
tacaagcacg agtgctgcat ttctttcgat actccgaaat ccgatggcgg gctgtttgtt    120
gatatgagta cttttcttgc atttggaagg gattgtgttg attggaacta tgagaagact    180
gggaacccag tttatttgca tataaagcag acaaagaagg cagatgctga agatagaccg    240
tccaaaaaac ccactctctt ggctataggt ttagacggag ggtttgataa cagtgaaccc    300
cagtacgaag aattctatga aatagttata ttgcctgata atgtcactct tcctttccca    360
tcggtggaat tgcctgagaa ggttagattg gctgttgatg ctattttact agctgaaggt    420
gctgagagga aagagcaact tgcttcctgg actgctgaca agaagcttgt cagtaaatat    480
gctacggatc tgcaacagct tgacaatggt gttgctgttc cacctgtggg ttggaaatgt    540
gcgaaatgtg acaagactga caatctttgg ctgaatctaa ctgatggaac tatcctatgt    600
ggtaggaaaa attgggatgg aactggtggt aatgaccatg cagttaacca ttacaaagaa    660
actggttatc cacttgctgt aaagcttggg accgtaactg ctgatttgga ggggcagat    720 gtttactcct atccagagga tgaaagtgtt gttgacccac ttttagcaga tcatctggca    780
cattttggta ttgacttctc atccttgcaa aagactgaaa tgacgactgc tgagagagaa    840
ctagaccaaa attttaactt tgattggaac cggattcaag agactggtga ggacgttgaa    900 ccacttttg gacctggtta cactggatta gtcaatcttg gtaacagttg ctacttggct    960
gctacaatgc aggttatgtt ctcaacgcgt tcattttgtt caagatacta ctttgatcaa   1020
cgtctgaaag aagcttttac tacggctcct gctgatccga ctgtagacct aacatgcag   1080 ctaacaaagc tggctcatgg tttgcttttct ggtaaatatt cgggtcctgt tctggagaag   1140
gataatactg ctaatgctgt aagctcacag aaacaggagg gtatccgtcc tcgaatgttc   1200
aagtcagtaa tagctgctag tcaccctgaa ttttcaacaa tgagacaaca ggatgcgtta   1260
gagttcttcc tgcattttat tgatcaagtt gaacggataa actctgggac acctaatttt   1320
gatccatcaa ggagcttcaa gtttggtatt gaagaacgcc tccaatgttc ctcgggcaaa   1380
gtcacttaca acagaaggaa tgattatatt ctgtctctta atattccttt ggagagggct   1440
ataaataaaa aagagctagc agaatttcaa aatttgaagg ctgagagagc tgcaggagga   1500
aaagaactgt ctgctgatga aattgttcgc cctagagtat cattgaagga ttgcctagat   1560
tgcttttcag ctcctgagga ggtgcatgat ttctacagca cagctttaac agctaggact   1620
acagcaatca aaactgcagg tttgacttct tttccagatt atctggtttt gcacatgcgg   1680
aaatttgtta tggaggaagg ttgggtgcca agaagctcg atgtctacat agatgtccct   1740
gaaaccattg acataagtag catgcgaagt aatggtattc aaccaggaga agagctgttg   1800
cctgacagtg ctgcagggga tggtgagcag tcaataaagc ttctggctga cgatgatatt   1860
gttgcacaac ttgtttcaat gggatttaat ctacttcatt gtcagaaggc tgctatcaat   1920
acttccaaca gtggagtaga ggcagcaatg gattggttac ttaatcatat gaatgatcca   1980
gatattgatg ctcctatatc agaaaacgtg caaaatcctg atattgatca atctaaagtt   2040
```

```
gatacgctgg tttcatttgg tttcgaagag aaacttgccc ataaggccct gaaggcatcg    2100
ggaggtgatg ttgaaaaagc tactgaatgg atattcagca gccctagtgc cagtactgca    2160
gcagacatgg atgttactac cagtagtgga gctgcagttg ataccttgat gcctgatgga    2220
ggaggaaaat acaggctcct gggattcgtg agccacatag gcacatctac ccactgtggc    2280
cattatgtcg ctcatattaa caaagatggc cggtgggtga ttttcaacga tgaaaaagtt    2340
ggggtctcaa aaaccccccc tatggatatg ggatacctct actttttttga aagacttgag    2400 agttga                                                                 2406
```

<210> SEQ ID NO 51
<211> LENGTH: 807
<212> TYPE: DNA
<213> ORGANISM: Solanum lycopersicum

<400> SEQUENCE: 51

```
atggcaaaat tagcgaaaaa tcgaggaagg aatagatttt ttaatagttg ttataagcct      60
ctacatttca acgatgatat atctaataca aataaacgag gtcatttgta taattcaaca    120
gatatatcta atttgaagag agtaaaatca caagaaaaat tggattcaat gttgggaaaa    180
gatttgacca aaaattttcg accaaatcga aaggagaatg cctttggaag gaattttttct    240 catgcactca aaaatgtgtt ttttgataca tcattgggga agaaaggcca gaggaaagag    300
cataagtatt catttggatc atgtaaaaag ttatcaacaa aatttgagaa atatttcat     360 tctacaaaag aaaaaaagtt ttcttcatca aaggatttac caaaaattac aagtagaatg    420
tccacaagtg caagcatgga tgatttttcc ttattcacta cttctacatc ctctttattt    480
tcttcttctt cttcttctcg ttcgtcttgt tcatcacaga aacgcaatt ttcatctttt     540 cacaggtcaa atcagaaaaa caatatgcaa gtgtatgata acgtaaaaga aaaagatatc    600
gcgctatgtt acaacaagaa cgttgggacg tattctcttt taatttgtct attggttatg    660
gttttttgtg ggaaagtttt tgccatcatt tgcacttcaa catggttcta ttttgctcct    720
cattgtttca aacgtataga ctcggatgag tacaagaaaa atgatggatt gttatattta    780
gtacaagaaa aaaatctaac tttttag                                         807
```

<210> SEQ ID NO 52
<211> LENGTH: 1059
<212> TYPE: DNA
<213> ORGANISM: Solanum lycopersicum

<400> SEQUENCE: 52

```
atggctactt ctcttcagtt ttcttcagat catcacccta ttcctcagga aaatcatcaa      60
acaacgaacc agacctcaac gggaggacgt agaaggtcga gtaaaaatgg acagaagaag    120
aagaagcaac cacaaagagg aatgggagtt gaacaactcg aacgtcttcg agtacaagat    180
cagatgaaaa acagtactat ccatggcgtt catcataatc atcagtacta ctctaataac    240
aatttcccta aattaactcc tgtttcatca tttaccggcg gtggtagtgc tagtgctgat    300
cctggaaatt atagtaattc tattttgaac tcttcaccag tacttcagtt ccccaaattg    360
tgtgcagtga gccctaatga ttttttttatg caacaaaaag ttgtgaatac tgggtttatt    420
ggatctagta gtacaaatca gttgatgatt tcttctcatg atcatcatca gtttcaatct    480
cagatgaatc tctacggatt tgcaacttct aagcccagta ctgagaaatc aaaggagctg    540
tatccaatgc caaatctgtt tagcagcaac aactcttgtt tctccgatcg ctgccgatca    600
```

| | |
|---|---|
| tgcaacaaaa agaaacgcat gatcaatgga gaagaaatta gcgttcatat ggaggacatg | 660 |
| atcagagaaa aggaagattc tggaacaaag cctttgcttc actcatacag tttacctagc | 720 |
| catcaacaaa agggcgtaga gattgtggca atccatagaa agggaagttc atccgcgttg | 780 |
| tcatccgatg aaggagcagt aatgatggag tatgattttt ttccagaaaa aatcagcagc | 840 |
| aaaagcacta atacttacaa agttgtttc gagaatgaag caacgatgat gagtgcttat | 900 |
| aattcaccag aatcttcttc atttgctgct gcagcagcag cagctggaaa tattattaat | 960 |
| ggtgaagctt cttctgttac tacaatatct tgggctgcag atactactac tacttcacct | 1020 |
| accagttcca ttgatctttc actgaagctt tcttgttag | 1059 |

```
<210> SEQ ID NO 53
<211> LENGTH: 288
<212> TYPE: DNA
<213> ORGANISM: Solanum lycopersicum

<400> SEQUENCE: 53
```

| | |
|---|---|
| atgagggaga ggttgtgtct tgaggttgag aggttagggc ttagtgctgt tattatgggg | 60 |
| agtcgaggat ttggagctac gaagaggggg agtgatggaa gacttgggag tgttagtgat | 120 |
| tattgtgtta ggcactgtgt gtgtcctgtt gtggttgtta ggtatcccga tgataaggat | 180 |
| gctggaaatg ctgttgtaga gcccgtggtt tctgttgctt cagctgctga agaagacgag | 240 |
| gaggaagctg agtaccatga tgcttctgag gatcgaaaag attcataa | 288 |

```
<210> SEQ ID NO 54
<211> LENGTH: 342
<212> TYPE: DNA
<213> ORGANISM: Solanum lycopersicum

<400> SEQUENCE: 54
```

| | |
|---|---|
| atggaagatc cttatggatt tgaagatcat ttcccttcaa tgatggagag attaggcgcg | 60 |
| gaaggattca tgagggagct ttgcaatgga ttttgtttac ttatggatgt gagtataggg | 120 |
| ctaataacat atgaaagttt gaagagaaac actatgaatc ttggtttaaa tgatttaaga | 180 |
| gatgatgagt tgatttacat gttggctgaa ggagatttgg atggtgatgg agcacttaat | 240 |
| caaatggaat tttgtattct catgtttaga ttgagtcctg gtttaatgga tggatctaag | 300 |
| caatacatgg atgatgtggg gcttattcat ttccaaccct aa | 342 |

```
<210> SEQ ID NO 55
<211> LENGTH: 2193
<212> TYPE: DNA
<213> ORGANISM: Solanum lycopersicum

<400> SEQUENCE: 55
```

| | |
|---|---|
| atgaaaggcc tattttcttt atgcatttgc taccaatttc tcttcatttt actaacttct | 60 |
| gcagcattag acacaatcac tacagataaa tccattagag atggtgacac aattgtttca | 120 |
| gctggagggg tttatgagct tggatttttc agccctggaa attcgaagaa tcattacgtt | 180 |
| ggcatatggt acaagaaaat atcaaatgga actgttgtct gggttgcaaa cagaagcatt | 240 |
| ccacttaatg acacttcagg agtgttaaca cttaatccca tggaattct tgtacttgtt | 300 |
| gataaatcca atgtctcaat ttggtcatca aactcatcaa gattgttaaa gaatccaaaa | 360 |
| gcacggttac tggattcagg gaaccttgtt gtcagtgatg gaaatgatag aggcctggaa | 420 |
| aataatttcg cgtggcagag ttttgactat ccaggaaata ctttgttacc tggtatgagg | 480 |
| ctaggaaaag atttttgtca cgggaatgaat tggcatttaa cgtcatggaa gagcacagat | 540 |

```
gatcctactc ctggtgatta tgtagatcgt gttgattcac atggatatcc acaattgttt      600
gtgtggaaaa attcatctat agtatttagc tcagggccat ggaatggtat tgcatttagt      660
ggtagtccta ataataaacc aaatacatat tacagtttcg agtttgttat taatcagcag      720
gaaatttact acacatatac aattaagaat gactccatac ccaccagggt ggtgctcaat      780
ccgtctggtg tgctagaaca cctaacatgg atagagcgca gtcagagctg gtttctctac      840
ttgacagcac aatttgataa ttgtgatcgt tttggtttat gtggacctta ttcaagttgc      900
aacatcaata actcccctcc atgtgactgt ttgaaaggtt ttgagcctag gtatcctcaa      960
gattctgcaa cagagtggtc tagtggttgc ataaggagaa cttctttgga ttgtacccat     1020
gatggttttc ttaaattttc aggtatcaaa atgcctgatt ctagaaactc ctggtataat     1080
gacagcatga accttgaaga ttgcgagaaa atgtgcttgg ctgattgcaa ttgtacagcc     1140
tactcagatc ttgatgttag aaatggcgga agtggatgct actatggtt tggtgaactc     1200 atagatatac gcgggttcag ccaaaatgaa caaaacctgt atgtgagagt tgcagcttca     1260
gaattagaca ggaaggggag gagaaagagg gcagccctga ttggcgtcat ttcagcagtg     1320
gtagcaacat ttatcctcag cttttttagct tggttttact tccgaagaag gaaaagaaga     1380
agaggattag aagttgaaaa tgaggacatg gagcttccat tgtttgattt agttactgtt     1440
actactgcta ctgataactt ctcttctgct aatgtgattg gagagggagg ctttggaccg     1500
gtttacaagg gtatcctacc aaatggacaa gatattgcag taaaaagact atcgaagcat     1560
tctggacaag gctttcaaga gttaaaaaat gaaatcgctc tcatttccaa gctgcaacat     1620
agaaaccttg tcaagctatt gggttgctgc cttgaaggag aagaaaggat gctaatctat     1680
gagttcatgc ccaatgctag cttggactat ttcattttg attcaagtag aaaagcatca     1740
cttgcatgga agaaccgttt tgaaattgct atgggaatat ctcgaggtct tctttacctt     1800
caccaggatt caagattacg aattattcac agagatctca agactagcaa catttttatta     1860 gatactgaca tgaatgccaa aatttcggac tttggccttg ccaaaatttt tggtggagat     1920
caagtggaag gaaaaactaa aagagtaata gggacatatg gatatatgtc cccggaatat     1980
gctgttgatg ggaaatattc agtaaaatca gatgtattca gcattggcgt aattattctt     2040
gaaatagtca gtggcagaaa gaacagaaaa tttcgtcatt tggaacatca tcacaatctc     2100
ttgggacatg taagcacaaa acttcattcc ctttattcac tcttagcttc ctattgtgat     2160
tacaactgta tgactgtgtt gttctgtttg taa                                   2193

<210> SEQ ID NO 56
<211> LENGTH: 2337
<212> TYPE: DNA
<213> ORGANISM: Solanum lycopersicum

<400> SEQUENCE: 56
atggtattga ttttgttttt tgtgtcagct atgttgaggc tcttcatttg ctgtcaattt       60
ctcttcatgt tactaacttc tgctgcatta gacacaatca ctacaaataa atctattaga      120
gatggtaata caattgtttc agctggaggg gtttatgagc ttggatttt cagccctgga      180 aattcgaaga atcgttacgt tggcatatgg tacaagaaga tatcacctac aactgttgtc      240
tgggttgcaa acagagacat tccacttaat gacacttcag gagtgttaac acttaatccc      300
aatggaattc ttgtacttgt tgataaatcc aatgtctcaa tttggtcatc aaactcatca      360
agattgttaa agaatccaaa agcaaggctc ctggataccg caaaccttgt tgttagtgac      420
```

```
ggaaatgata gagatcaggg aattaatttc gcgtggcaga gttttgatta tccaggaaat    480
actttattac ctggaatgaa ggtaggaata gatttggtta cggggatgga taggtatgta    540
acgtcgtgga agagcacaga tgatcctact cctggtgatt atgtagatcg tgttgattca    600
catggatacc cgcaattgtt cttgtcgaga aattcatctg tagtgtttag ctcagggcca    660
tggactggtg ctgcattttc tagtagtcct agtaataaac catctttgta ttatacgttc    720
gagtttgtta tcaatcagaa ggaaatttac ttcaaatatg agcttaagag tgactctttg    780
cccaccaggg tggtgctcaa cccggatgga gtgatacaac acctaatatg gattgagcat    840
actcagagct ggtttctcta cttgacagca caacttgata attgtgatcg tttttgcttta    900
tgcggacctt attcaagttg caacatcaat aactcccctc catgtgactg tttgaaaggt    960
tttgagccta ggtatcctca agaatctgca gcagactggt ctagtggttg cgtaaggaga   1020
acttctttaa attgtaccca tgatggtttt cttaaattta cgcgtatcaa gatgcctgat   1080
tctagaaact cctggtataa tgagagaatg aaccttgaag attgcgagaa atgtgtttta   1140
gctgattgca attgtacagc ctactcagat cttgatgtta gaaatggcgg aagtggatgc   1200
ttactatggt ttggagaact catagatata cgagaattca gccaaaatga gcaaaatcta   1260
tatgtgagag tagctgcttc agaattaggc gaatgtatat tgacaggttc aaaagttgaa   1320
aatgaggaca tggagcttcc attgtttgat ttagttactg ttacaagttc cactggaaac   1380
ttctcttctg ctaatgtgat tggggaaggc ggatttggac cggtctacag gggtatccta   1440
ccaagtggac aagagatagc agtaaagagg ctatcgaagt attctggaca aggcattcaa   1500
gagttaaaaa atgaaatcgt tctcatttcc aagctgcaac ataggaacct tgtcaagtta   1560
ttgggttgct gtcttgaagg agaagaacgg atgctaatat atgagttcat gcccaacgct   1620
agcttggact atttcatttt tgatccaagc agaaaagctt cacttggatg gaagaatcgt   1680
tttgaaattg ctatgggaat atctcgtggt cttctttacc ttcaccagga ttcaagattg   1740
agaattattc accgagatct caagaccagc aacattttat tagatactga catgaatgcc   1800
aaaattctg actttggcct tgccaaaatt tttggtggtg accaagagga aggaaaaact   1860
aagagagtaa tagggacata tggatatatg tccccggagt atgctgttga tgggaaatac   1920
tcagtaaaat cagatgtatt cagcatcggt gtaatcattc ttgaaatagt tagtggcaga   1980
aagaacagaa aatttcgtca tttggaacat catcacaatc tcttgggaca tgcatggtta   2040
ctttggattg aaggcaacgc gttggaactg atagacgaat gtatcaaaga atccttttca   2100
gaatctcaag tgctgagatg catccaggtt ggtttgttat gcgtccaaaa actccccgag   2160
gataggccta caatggcatc agtagttttc tggttaggca atgaaggtct ggttcttcct   2220
caaccaaagc aacctggttt tttcatagag aggaattcaa tggaatcaac agaatcatca   2280
actgatgaag tatatgtaag tagcagcgtg tcgataacag ttctagagcc aagatag     2337
```

<210> SEQ ID NO 57
<211> LENGTH: 4722
<212> TYPE: DNA
<213> ORGANISM: Solanum lycopersicum

<400> SEQUENCE: 57

```
atgaaaggga acatttttt attttcttgc tcaattttc ttccagtctt actaatttcc     60
actgcattag acacaatcac aacagagaaa ccaattagag atggtgacac aattatttca    120
gctggagggg ttttgagct tggatttttc agccctggaa attcgaagaa tcgttacgtt    180
ggcatatggt ttaagaagat agcaactaga actgttgtct gggttgccaa cagaaacttc    240
```

```
ccactgaatg acaattcagg agtgttatca ctcaatccca atggaattct tgtacttctt    300
cgtaattcca atgcctcaat ttggtcttca aactcatcaa gattgttgac gaatccaaaa    360
gcatggctcc tggattctgg taaccttgtt gtgactgatg gaaatgatag tgatccagaa    420
gttaatttcg cgtggcagag ttttgattat ccaggagata ctttactacc tgggatgaag    480
cttggacgta atctggtcac gggcatggat tggtacatag agtcatggaa gagcagtgat    540
gatcctgcgc ctggtgaata tatagaacgt cttgattctc atggataccc acaattttc     600
gtgtggcaaa attcatctat agtatatagc acagggccat ggaatggtat cacatttagc    660
agtagtccaa aaaatcaacc agctatatat tatgctttcg agtttgttat taaacagaag    720
gagatttact ttaaatacga gctaaacgag tccctgccca ccagggtagt gatcaatcag    780
gctggaatgg tagaacacct aacatggatt gagcgaaatc agagatggat agtctatgta    840
tcaacacaat ctgataattg tgatcgtttt gctttatgtg gtccttatgc aagttgcaac    900
atcaataact ctcctccatg tgactgcttg caaggtttcg agcctaggta tcctgaacaa    960
tggtatgcag tggactggtc taatggttgt ataaggaaaa cttctttgtc ttgtaaccaa   1020
gatggttttc ttaaatttac gaatatcaag atgccggatt ctagacactc ctggtataat   1080
gtaagcatga atcttgaaga atgcaagaaa atgtgcttgg ctgattgcaa ttgtacagcc   1140
tactcaaatc ttgatataag aaatggcgga agtggatgtt tactatggtt cggtgagctc   1200
attgatatta gagagtacaa caaaaatgag caacgcctgt tgtgagagt tgctgcttca    1260
gaattagatc cagtcaggac ttggagggga agtggccag ctctgattgc ggtcatttca     1320
gcactagcag caacttttat cctcatcttt gtagcttggt ttaccttcca agaaggaac    1380
aaaaaaacag acaaacatac tggaggttca gaagttggaa agaatgacct tgagttgcca   1440
ttgtttgatt tagttactgt tactacttcc actgaaagtt tctcttctgc gaatgtgatt   1500
ggtgagggtg gctttggaca ggtttacaag ggtattctac cagatggaca agagatagca   1560
gtaaagaagc tatcgaagta ttctggacaa ggcgttcaag agttaaaaaa tgaaattgtt   1620
ttcatttcca agctgcaaca tagaaaacctt gtcaagcttt tgggttgctg ccttgaagga   1680
gaagaaaaga tgctaatcta tgagtttatg cccaactcta gcttggactg tttcattttt   1740
gatccaagca gaaaagcttc acttacatgg aagaatcgtt ttgaaattgc tgtgggaata   1800
tctcgaggtc ttctatacct tcatcaggac tcaagattta gaattattca tagagacctc   1860
aagaccagca acattttact agatggcaac atgaatgcca aaattgctga ctttggcctt   1920
gccaaaattt ttggcggaga acaagtggaa ggaaatacta agagagtgat agggacatat   1980
ggatatatgt cacctgagta tgctgttgat gggaaatatt caataaaatc cgatgtattc   2040
agtattggcg tcatcattct agaactagtt agtggcagaa ggaacaggaa atttcgtcat   2100
ttggaacatc atcacaatct tttgggacat gcatggttac tttggactga agacaaagcg   2160
ttggaactga tggacgaatg tttgaaagaa tcatttgcgg aatctcaagt gttgagatgc   2220
atccaggttg gtttgttgtg cgcccaaaaa caccctgagg ataggcctac aatggcatca   2280
gtagttttct ggttgggaaa tgaaggcctg gttcttcctc aaccaaagca gcctggattt   2340
tttatcgaaa ggaattcaat ggaatcaaca gaatcagctc agtttataaa cacgatcaca   2400
acagatagat ccattagaga cggtgacaca attgtttcag ctggtgggat ttatgagctt   2460
ggattttca gttctggaaa tgcgaagaat cgttacgtag gcatatggta caagaagata   2520
tcaactcaaa ctgttgtctg ggtagcaaac agagatattc cacttaatga cacatcagga   2580
```

```
gtgttaatac tcaaacccaa tggaattctt gtacttgttg ataattccaa tacatcaatt    2640
tggtcatcaa actcatcaag accgttaaag gatccaaaag cacggatcct ggattccggg    2700
aaccttgttg tcaatgatgg aaatgaaaga gacctggaaa ttaacttcgc atggcagagt    2760
tttgattatc caggaaatac ttttatacct ggaatgaaac ttggacgtaa tttggtcacg    2820
ggcatggatt ggtatatgtc gtcttggaag agcattgatg atccttctcc tggtgaatat    2880
ataaaccgtc ttgattctca tggatacccg caattgtttg tgtggaaaaa ttcaactata    2940
gtgtctagct cagggatatg gaaaggtaat gcatttactg ttagtgctaa cagtagacca    3000
aatacacatt acacttccga gtttataatt aatcagcagg aaatttacta ccaattcaag    3060
cttaagaacg agtcactgcc cagcaggatg gtgctcaacc cggaagggct gatagaacac    3120
ctaacatgga ttgagagcag tcaaagctgg tttctgtact caacagtaca gtttgatagc    3180
tgtggtcgtt ttgctttatg cggtccttat tcaagttgca acatcaataa ctcccctcca    3240
tgtgactgtt tgcaaggttt caatcctagg gttcctcaac agtctgcagc agattggtct    3300
tctggttgtg ttaggagcac ttctttggat tgtaacaaag acggttttct taaatttaca    3360
ggcatcaaga tgcctgattc tagaaactcc tggtttaata agagcattaa ccttgaagaa    3420
tgtgagaaat tatgcttagc taattgcaac tgtacagcct actcaaatct tgatgtcaga    3480
aatggcggaa gtggatgctt actatggttc ggagatctca ttgatattcg agagttgagc    3540
caaaatgagc aaaacctgtt tgtgagagtt gctgcttcag aaatagacag gaagcaaagg    3600
agaaagatgt cagtcctgat tggtgtcatt tcagcagtgg tagcaacatt tatcctcagc    3660
tttttagctt ggttttactt ccaaagaagg aaaagaagaa taggtccaga agttgaaaat    3720
gaggacatgg agcttccatt gtttgattta gttactgtta ctactgccac tggggacttc    3780
tctgctatga atgtgatcgg gaaggtgga tttggaccgg tttacaaggg tatcctacca    3840
aatggacaag agatagcagt gaagaggtta tcaaagcatt ctggacaagg cttacgagag    3900

ttaaaaaatg aattcgttct catttccaag ctgcaacaca ggaaccttgt caagcttttg    3960
ggttgctgcc ttgaaagaga agaacggatg ctcatctatg agtttatgcc caatgctagc    4020

ttggactatt tcatttttga tccaagcaga aaaacttcac ттттcaтggaa gaaccgctt    4080 gaaattgcta taggaatatc tagaggtctt ctttaccttc accaggactc aagattaaga    4140
attattcaca gagatctcaa gaccagcaac atcttattag atactgacat gaatgccaaa    4200

atttctgact tcggccttgc caagatattt ggtggagatc aagtggaagg agaaactaag    4260
agtatagtag ggacatatgg atatatgtcc ccggagtatg ttgttgatgg gaaatatca    4320 gtaaaatccg atgtattcag cattggtgta attattcttg aaatagttag tggcagaaag    4380
aacaggaatt tcgtcatttt ggaacatcat cacaatctct tgggacatgc atggttactt    4440

tggactgaag gcaacgcgtt ggaattcatg gatgaacgtt tgaaagaatc attttcagaa    4500

tctcaagtgt тgaгaтgcaт ccaggtcggt ttgttatgcg tccagaaact cccagaggac    4560
aggcctataa tggcatcagt ggttttttgg ttgggaaatg aaggtctggt tcttcctcaa    4620
ccaaggcatc caggtttctt cacagagagg aatccaatgg aatctactga tgaagaatgt    4680
ctaagtaaca acgcgacgtt aactgttctt gagccaagat ag                       4722
```

<210> SEQ ID NO 58
<211> LENGTH: 675
<212> TYPE: DNA
<213> ORGANISM: Solanum lycopersicum

<400> SEQUENCE: 58

```
atggcaatgc ttcaatggtt tcctcttctt tgcattttct tcatctcagc ttctgctgct      60
aaagttcaaa ccaaggtaac tgataatcct gctgatgagc tggtatctgc ccttaatagt     120
aacagaactg cgaataaatt atcctcctta tacagtaacc ctggcttggc atgcttggct     180
ctgcaatata taaaagcata cggaggtgat tgtaaagtag ttggagggcc agatggaaag     240
aaacctgctg aatctgaatt cgcccaagaa tttgccccca actgtggtgt gcaggcatca     300
tcgcttgctc aaataactgg aagatttctc gcatgtcaat ctaagtatgc ggaaccttct     360
gaagcattca atgatattct tataagaaat accaagagtt tggatattct ctatagcaag     420
aatcacactg aggttggtgc tgctgtgagt ggctccggtg gtggtggccc ctatttctgg     480
tgtgtactct tcagtaatgg caaaccaaag agtagctttt ccacaggtgg agttgagcct     540
aaggtaagta gacctggatg cttcagtggt tctaatgacc aatgcagtgg tgctaatact     600
ttgtctcaaa ccatatatct ctggacaatc actgtaggag cttccgttgc actgctttat     660
gccttaggag tatga                                                     675

<210> SEQ ID NO 59
<211> LENGTH: 645
<212> TYPE: DNA
<213> ORGANISM: Solanum lycopersicum

<400> SEQUENCE: 59
atgggaatat caagagggat tctttatctt caccaggatt ccagattaag gatcatacat      60
agagatctaa agacgagcaa cattttactg gacagtgaat ggaatcccaa gatttcagac     120
tttggactgg ctaggattat tggctgtgac caaaacgaag caagaacaaa aagagtaata     180
gggacatatg gatatatgtc tccagaatac gcagttgatg ggaaattttc agtgaaatca     240
gatgttttca gtcttggtgt tcttctgcta gaaatagtaa gtggaagaaa gaacagaaca     300
tttcgtcatc cagatcacca ccatagtctt ataggacatg cttggttatt atggaacgaa     360
ggaaaagcct tggaactaat cgatgattgt ttaaaagaat cgtttgtgga atcccaagtg     420
ctaagatgtg ttcatgtggc actgttatgt gttcaacgac taacagatga aagaccaaca     480
atgtcatcag tggtattcat gttaagccat gaagaagtgg cattacctca accaaaggag     540
cctggtttct tcatagagag aagtatagct gaaacagatg attcaaatga gaaaaggtgt     600
atcagtgaca atgttttgac attaacaatt cttcaaccaa gatag                    645
```

TOMATO PLANTS EXHIBITING TOLERANCE TO CONTINUOUS LIGHT

RELATED APPLICATION DATA

This application is a National Stage Application under 35 U.S.C. 371 of PCT application PCT/NL2010/050562 designating the United States and filed Sep. 6, 2010; which claims the benefit of EP patent application number 09169555.1.2 and filed Sep. 4, 2009 each of which are hereby incorporated by reference in their entireties.

FIELD OF THE INVENTION

The present invention relates to plant breeding and molecular biology. More specifically, the present invention relates to a method for detecting a gene associated with tolerance to continuous light in tomato, to a method of producing a continuous light-tolerant tomato plant therewith and to continuous light-tolerant tomato plants thus obtained and parts thereof.

BACKGROUND OF THE INVENTION

Tomato (*Solanum lycopersicum*, formerly known as *Lycopersicon esculentum*) is a plant of the Solanaceae or nightshade family. It is a short-lived perennial plant, grown as an annual plant, and a close relative of the potato. The fruit (i.e. the tomato) is an edible, brightly coloured (usually red, from the pigment lycopene) berry, 1-2 cm diameter in wild plants, commonly much larger in cultivated forms. The plant is now grown worldwide for its edible fruits, which are major fresh market vegetables worldwide.

During the last decades, tomato breeding was mainly focused on yield, disease tolerance, and fruit quality aspects such as uniform ripening and taste. Yield improvements have been achieved due to new production methods, improved pest management and varieties that are better suited for new production methods, but the gains in yield become smaller. New varieties with 5 or 15 fruits more per plant gave a yield increase of 2-4%.

As the world population continues to grow, the demand for fresh vegetables, such as tomatoes, is ever increasing worldwide. Thus, a continuing need exists for means and methods for improving yield of tomatoes.

SUMMARY OF THE INVENTION

The inventors have surprisingly found that the yield of some tomato plants can be increased by the use of longer photoperiods or even continuous photoperiods. This is surprising, because commercially used varieties, when grown in continuous light, show a strong increase in chloroplastic starch, leaf chlorosis, necrosis and consequently very poor biomass production. In effect, continuous light is often lethal for the crop. However, the inventors have found that tomato plants exist which are not only tolerant to continuous light, but in fact display an increase in yield when exposed to continuous light when compared to 16 hours of light.

The present inventors have successfully identified a quantitative trait locus (gene) which is responsible for tolerance to continuous light present in the genome of several wild relatives of tomato, i.e. in *S. neorickii, S. habrochaites, S. pennellii, S. peruvianum, S. chilense* and *S. chemielewskii*, and in *S. lycopersicum*, e.g. var. Sub Arctic Plenty.

The inventors were subsequently able to produce continuous light tolerant tomato plants by crossing these continuous light tolerant wild (donor) tomato lines with non-tolerant recipient tomato plants. These plants thus produced exhibited more tolerance to continuous light than any cultivated tomato plant produced thus far. In addition, several plants also produced more biomass when exposed to continuous light than plants from the original recipient line when exposed to 16 hours of light. Therefore, the present invention enables more efficient culturing and higher yields.

The present invention provides in a first aspect a method of selecting a tomato plant comprising exposing a tomato plant and determining whether said plant exhibits tolerance to continuous light, wherein said tolerance is indicated by decreased level of chlorosis upon said exposure, and further determining whether said plant exhibits a significant increase in yield.

The invention further provides a method for producing a first tomato plant by a method according to the invention, crossing said selected plant with a second tomato plant to produce offspring plants and selecting from said offspring plants a plant having tolerance to continuous light and having increased yield as compared to said second tomato plant.

The invention further provides a method of producing a tomato plant, tolerant to exposure to continuous light, said method comprising steps of:

a) providing a tomato donor plant tolerant to exposure to continuous light, preferably of the species *S. neorickii, S. habrochaites, S. pennellii, S. lycopersicum, S. peruvianum, S. chilense* or *S. chemielewskii;* b) transferring nucleic acid from said donor plant to at least one recipient tomato plant which is not tolerant to exposure to continuous light, wherein said transfer results in the introduction of genomic material from said donor plant in the corresponding region of the genome of said at least one recipient plant;

c) selecting from said at least one recipient plant a plant that comprises within its genome a gene for continuous light tolerance derived from said donor plant, wherein said selection comprises detecting in chromosome 7 of said recipient tomato plant at least one genetic marker linked to said gene for light tolerance.

In preferred embodiments, the location of said gene on chromosome 7 of said plant is indicated by a genomic region comprising the genetic markers "7-20-1", "7-20-2" on chromosome 7 of *S. neorickii*, "7-10", "7-25" on chromosome 7 of *S. neorickii*, "7-17", "7-25" on chromosome 7 of *S. chilense*, "7-19", "7-25" on chromosome 7 of *S. pennellii*.

In another preferred embodiment, said transfer of nucleic acid comprising said gene for tolerance to continuous light, or a light tolerance conferring part thereof, is performed by crossing said donor tomato plant tolerant to exposure to continuous light with a recipient tomato plant which is not tolerant to exposure to continuous light, to produce offspring plants comprising said gene as an introgression, and wherein step c) is performed on at least one offspring plant.

In another preferred embodiment, said step c) is performed by detecting said genetic marker in DNA isolated from said at least one recipient tomato plant.

In another preferred embodiment, said step c) further comprises subjecting said plant to bioassay for measuring the capability of growing in continuous light of said plant.

In another aspect the invention provides a continuous light tolerant tomato plant or a part thereof, obtainable by a method according to the invention.

The invention further provides a gene for continuous light tolerance, wherein said gene is associated with tolerance to continuous light and wherein the location of said gene on chromosome 7 of said plant is indicated by a genomic region comprising the genetic markers "7-20-1", "7-20-2" on chromosome 7 of *S. neorickii*, "7-10", "7-25" on chromosome 7 of *S. neorickii*, "7-17", "7-25" on chromosome 7 of *S. chilense*, "7-19", "7-25" on chromosome 7 of *S. pennellii*. The alleles on the positions of the genome indicated by this gene is an aspect of the present invention.

A gene of the present invention may be in the form of an isolated, preferably double stranded nucleic acid sequence comprising said gene or a tolerance-conferring part thereof. Very suitably, the size of the nucleic acid sequence, which may for instance be isolated from the chromosome of a suitable donor plant, may represent a genetic distance of 1-100 cM, preferably 10-80 cM on said chromosome. Preferably said genetic distance is between 64 and 78 cM on said chromosome, even more preferably between 72 and 75 cM. Said nucleic acid may comprise at least 50, more preferably at least 500, even more preferably at least 1000, still more preferably at least 5000 base pairs. One or more nucleic acid sequences comprising a gene or a tolerance-conferring part thereof according to the invention may in turn be comprised in a nucleic acid construct, said construct may further comprise regions that flank said one or more nucleic acid sequences and which regions are capable of being integrated into a suitable vector for transfer of said one or more nucleic acid sequences into a suitable continuous light intolerant recipient tomato plant. The vector may further comprise suitable promoter regions or other regulatory sequences. Said gene may also be in a form present within the genome of a tomato plant. The gene of the present invention preferably comprises at least one marker, preferably two markers associated with continuous light-tolerance selected from the group consisting of the markers of FIG. 10 linked to said gene.

The invention further provides a method for detecting a gene for tolerance to continuous light, comprising detecting at least one genetic marker linked to a gene for tolerance to continuous light derived on chromosome 7 of a suspected continuous light tolerant tomato plant, wherein the location of said gene on chromosome 7 of said plant is indicated by a genomic region comprising the genetic markers "7-20-1", "7-20-2" on chromosome 7 of *S. neorickii*, "7-10", "7-25" on chromosome 7 of *S. neorickii*, "7-17", "7-25" on chromosome 7 of *S. chilense*, "7-19", "7-25" on chromosome 7 of *S. pennellii*.

In another aspect the invention provides a continuous light-tolerant tomato plant, or a part thereof, comprising within its genome a gene for continuous light tolerance, or a continuous light-tolerance-conferring part thereof, wherein the location of said gene on chromosome 7 of said plant is indicated by a genomic region comprising the genetic markers "7-20-1", "7-20-2" on chromosome 7 of *S. neorickii*, "7-10", "7-25" on chromosome 7 of *S. neorickii*, "7-17", "7-25" on chromosome 7 of *S. chilense*, "7-19", "7-25" on chromosome 7 of *S. pennellii*, wherein said gene or said continuous light-tolerance-conferring part thereof is not in its natural genetic background.

In another aspect the invention provides a method of producing a continuous light-tolerant inbred tomato plant, comprising a) producing a continuous light-tolerant tomato plant according to the invention;

b) crossing said continuous light-tolerant tomato plant with itself or another tomato plant to yield progeny tomato seed;

c) growing said progeny tomato seed of step b) to yield an additional continuous light-tolerant tomato plant;

d) repeating the crossing and growing steps from 0 to 7 times to generate a continuous light-tolerant inbred tomato plant.

Preferably said step c) further comprises the step of identifying plants that exhibit continuous light tolerance and possess commercially desirable characteristics.

In another preferred embodiment said method further comprises the step of selecting homozygote inbred tomato plants, preferably wherein said inbred plants are homozygous for said continuous light allele.

In a further aspect, the invention provides a continuous light-tolerant inbred tomato plant, or parts thereof, obtainable the method according to the invention.

In a further aspect, the invention provides a hybrid tomato plant, or a part thereof, that exhibits tolerance to continuous light, wherein said hybrid tomato plant is obtainable by crossing a continuous light-tolerant inbred tomato plant obtainable by a method according to the invention with an inbred tomato plant that exhibits commercially desirable characteristics. Such characteristics include inter alia a high yield (in excess of 50, 60 kg/m$^2$ of tomatoes and/or resistance to tobacco mosaic virus (TMV), blight and/or *Botrytis*.

In another aspect, the invention further provides the use of a genetic marker selected from the group consisting of the genetic markers of FIG. 10 for the detection of genes for continuous light-tolerance, and/or for the detection of continuous light-tolerant tomato plants.

In another aspect, the invention provides an indeterminate tomato plant, tolerant to exposure to continuous light or a part thereof.

In a further aspect, the invention further provides a tissue culture of regenerable cells of the tomato plants according to the invention, preferably said regenerable cells comprise cells or protoplasts isolated from a tissue selected from the group consisting of leaves, pollen, embryos, roots, root tips, anthers, flowers, fruits, and stems and seeds.

The continuous light-tolerant donor tomato plant used in methods of the present invention is preferably selected from the group consisting of *S. neorickii*, *S. habrochaites*, *S. pennellii*, *S. lycopersicum*, *S. peruvianum*, *S. chemielewskii*, more preferably, a wild tomato accession is used as the donor plant. Highly preferred donor plants are *S. pennellii* LA716, *S. peruvianum* LA1708, *S. habrochaites* LA1777, *S. habrochaites* G1560, *S. habrochaites* Lyc4/78, *S. chilense* LA1959, *S. chmielewskii* LA1840, *S. neorickii* LA2133 and *S. lycopersicum* variety "Sub arctic plenty".

The continuous light-tolerant recipient tomato plant used in methods of the present invention is preferably a plant of the species *Solanum lycopersicum*, more preferably an *S. lycopersicum* cultivar that possess commercially desirable characteristics, or another commercial tomato line.

DESCRIPTION OF THE DRAWINGS

FIG. 11: Sequences of genetic markers. The markers indicate the polymorphic sequences between the tolerant and sensitive genotype. The polymorphic positions as indicated in these sequences are SNPs. An example for use of these SNPs as markers is provided in Example 7 below. The skilled artisan will understand that the markers as indicated in this figure refer specifically to the polymorphic positions in the sequences given. Marker 1: Sequence of the marker "7-1" derived from *S. neorickii* LA2133 located at 0.4 cM of chromosome 7 ([T/G] indicates the polymorphic position) (SEQ ID NO:1). Marker 2: Sequence of the marker "7-2" derived from *S. pennellii* 0716 located at 1.2 cM of chromosome 7 ([T/G] indicates the polymorphic position) (SEQ ID NO:2). Marker 3: Sequence of the marker "7-3" derived from *S. neorickii* LA2133 located at 2.0 cM of chromosome 7 ([A/T] indicates the polymorphic position) (SEQ ID NO:3). Marker 4: Sequence of the marker "7-4" derived from *S. neorickii* LA2133 located at 3.5 cM of chromosome 7 ([T/C] indicates the polymorphic position) (SEQ ID NO:4). Marker 5: Sequence of the marker "7-5" derived from *S. neorickii* LA2133 located at 21.4 cM of chromosome 7 ([A/T] indicates the polymorphic position) (SEQ ID NO:5). Marker 6: Sequence of the marker "7-6" derived from *S. neorickii* LA2133 located at 22.3 cM of chromosome 7 ([T/C] indicates the polymorphic position) (SEQ ID NO:6). Marker 7: Sequence of the marker "7-7" derived from *S. neorickii* LA2133 located at 24.8 cM of chromosome 7 ([T/C] indicates the polymorphic position) (SEQ ID NO:7). Marker 8: Sequence of the marker "7-8" derived from *S. neorickii* LA2133 located at 27.5 cM of chromosome 7 ([T/C] indicates the polymorphic position) (SEQ ID NO:8). Marker 9: Sequence of the marker "7-9" derived from *S. pennellii* 0716 located at 28.1 cM of chromosome 7 ([A/G] indicates the polymorphic position) (SEQ ID NO:9). Marker 10: Sequence of the marker "7-10" derived from *S. neorickii* LA2133 located at 38.0 cM of chromosome 7 ([A/G] indicates the polymorphic position) (SEQ ID NO:10). Marker 11: Sequence of the marker "7-11" derived from *S. neorickii* LA2133 located at 38.8 cM of chromosome 7 ([T/C] indicates the polymorphic position) (SEQ ID NO:11). Marker 12: Sequence of the marker "7-12" derived from *S. pennellii* 0716 located at 40.0 cM of chromosome 7 ([T/G] indicates the polymorphic position) (SEQ ID NO:12). Marker 13: Sequence of the marker "7-13" derived from *S. neorickii* LA2133 located at 43.0 cM of chromosome 7 ([T/C] indicates the polymorphic position) (SEQ ID NO:13). Marker 14: Sequence of the marker "7-14" derived from *S. neorickii* LA2133 located at 45.6 cM of chromosome 7 ([A/G] indicates the polymorphic position) (SEQ ID NO:14). Marker 15: Sequence of the marker "7-15" derived from *S. neorickii* LA2133 located at 48.1 cM of chromosome 7 ([A/T] indicates the polymorphic position) (SEQ ID NO:15). Marker 16: Sequence of the marker "7-16" derived from *S. neorickii* LA2133 located at 49.2 cM of chromosome 7 ([A/T] indicates the polymorphic position) (SEQ ID NO:16). Marker 17: Sequence of the marker "7-17" derived from *S. neorickii* LA2133 located at 54.0 cM of chromosome 7 ([T/C] indicates the polymorphic position) (SEQ ID NO:17). Marker 18: Sequence of the marker "7-18" derived from *S. neorickii* LA2133 located at 61.0 cM of chromosome 7 ([T/G] indicates the polymorphic position) (SEQ ID NO:18). Marker 19: Sequence of the marker "7-19" derived from *S. pennellii* 0716 located at 64.0 cM of chromosome 7 ([A/T] indicates the polymorphic position) (SEQ ID NO:19). Marker 20: Sequence of the marker "7-20" derived from *S. neorickii* LA2133 located at 46.18 cM of chromosome 7 based on mapping in the 2133-42 population and at 73.0 cM based on mapping using the EXPEN 2000 linkage map of chromosome 7 ([T/C] indicates the polymorphic position) (SEQ ID NO:20). Marker 21: Sequence of the marker "7-21" derived from *S. neorickii* LA2133 located 46.74 cM of chromosome 7 based on mapping in the 2133-42 population and at at 78.0 cM based on mapping using the EXPEN 2000 linkage map of chromosome 7 ([A/G] indicates the polymorphic position) (SEQ ID NO:21). Marker 22: Sequence of the marker "7-22" derived from *S. neorickii* LA2133 located at 80.0 cM of chromosome 7 ([T/C] indicates the polymorphic position) (SEQ ID NO:22). Marker 23: Sequence of the marker "7-23" derived from *S. neorickii* LA2133 located at 99.6 cM of chromosome 7 ([T/C] indicates the polymorphic position) (SEQ ID NO:23). Marker 24: Sequence of the marker "7-24" derived from *S. pennellii* 0716 located at 100.4 cM of chromosome 7 ([A/T] indicates the polymorphic position) (SEQ ID NO:24). Marker 25: Sequence of the marker "7-25" derived from *S. neorickii* LA2133 located at 104.0 cM of chromosome 7 ([A/G] indicates the polymorphic position) (SEQ ID NO:25). Marker 26 Sequence of the marker "7-20-1" derived from *S. neorickii* LA2133 located at 43.68 cM of chromosome 7 based on mapping in the LA2133-42 population and at 75 cM based on mapping using the EXPEN 2000 linkage map ([T/G] indicates the polymorphic position) (SEQ ID NO:26). Marker 27 Sequence of the marker "7-20-2" derived from *S. neorickii* LA2133 located at 44.35 cM of chromosome 7 based on mapping in the LA2133-42 population and at 72 cM based on mapping using the EXPEN 2000 linkage map ([C/A] indicates the polymorphic position) (SEQ ID NO:27). Marker 28 Sequence of the marker "7-20-3" derived from *S. neorickii* LA2133 located at 44.46 cM of chromosome 7 based on mapping in the LA2133-42 population and at 73 cM based on mapping using the EXPEN 2000 linkage map ([G/C] indicates the polymorphic position) (SEQ ID NO:28).

FIG. 12: The CLT locus. The CLT locus is positioned between markers 7-17 and 7-20. Presented genotypic data (the genotypes include "homozygous for donor" or "recurrent parent" and "heterozygous") is generated from F2 plants, while phenotypic scoring (the phenotypes include "Tolerant to continuous light", "susceptible for continuous light" and "segregating") is performed on F3 plants. Light grey blocks indicate genomic segments originating from the tolerant parent. Dark grey blocks indicate segments that are originating from the sensitive parent. White blocks indicate heterozygous segments. Markers are ordered according to map LA2133-42.

DETAILED DESCRIPTION OF THE INVENTION

Definitions

Figure 1:
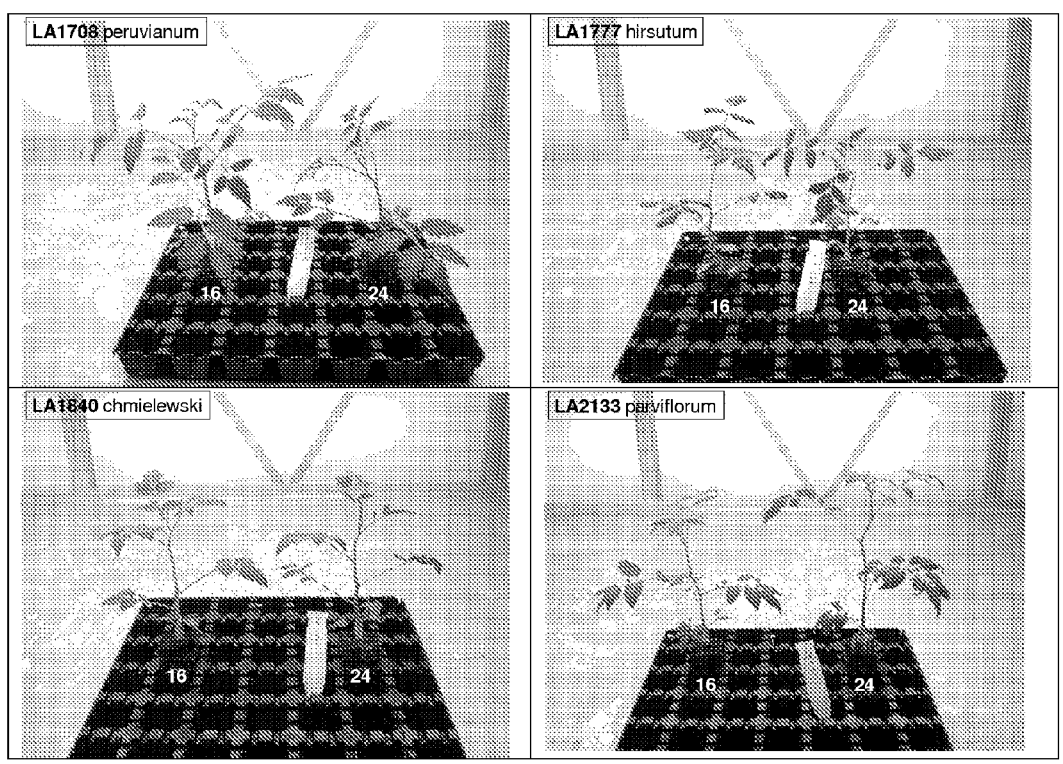
FIG. 1: Species and varieties tolerant to continuous light. Plants shown on the left were exposed to 16 hr and plants on the right are exposed to continuous light. Clearly the typical symptoms of light intolerance (leaf chlorosis, necrosis and poor biomass production) are not expressed in these tolerant lines, while the symptoms are clearly visible in non tolerant lines under the same conditions.
Figure 1:
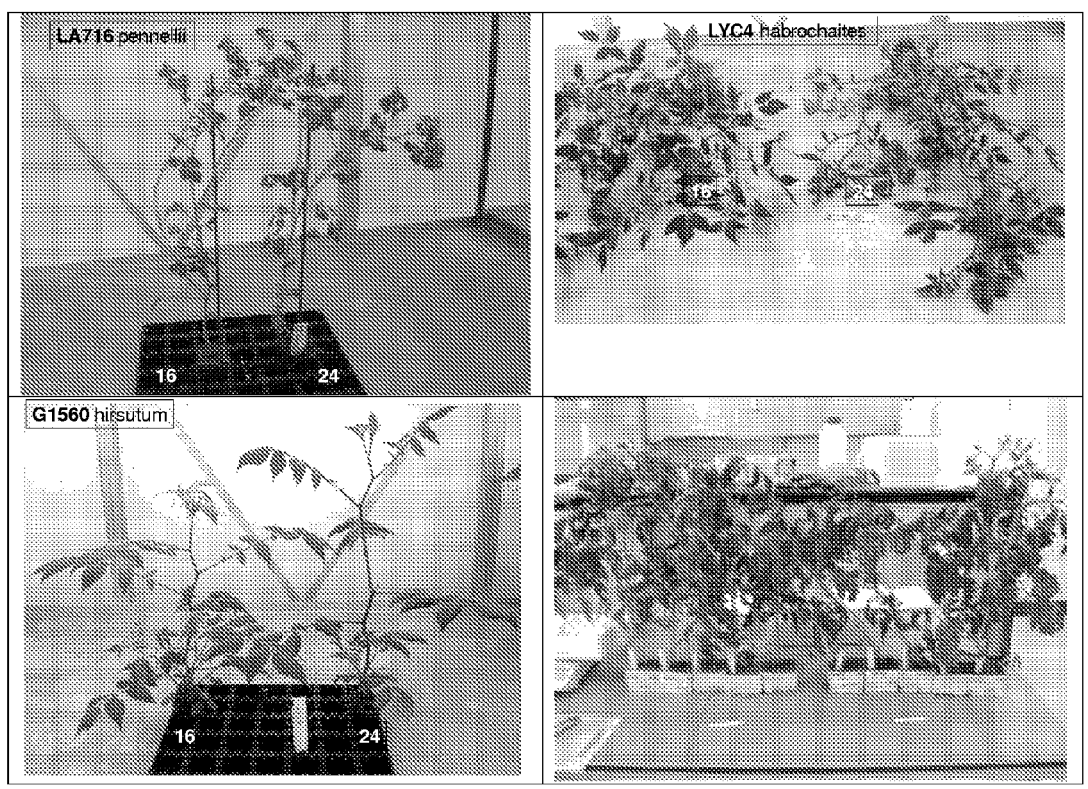

The term "light" as used herein means light of a suitable wavelength for growing plants at an average light intensity which is higher than the light energy known as the "light compensation point". This is the light intensity at which the amount of carbon dioxide released in respiration equals the amount used in photosynthesis, and the amount of oxygen released in photosynthesis equals the amount used in respiration.

The compensation point is the amount of light intensity on the light curve where the rate of photosynthesis exactly matches the rate of respiration. At this point, the uptake of $CO_2$ through photosynthetic pathways is exactly matched to the respiratory release of carbon dioxide, and the uptake of $O_2$ by respiration is exactly matched to the photosynthetic release of oxygen. Methods to establish the light compensation point of a plant are well known in the art. Preferably, said light has a light intensity of at least 20 µmol $m^{-2}$ $s^{-1}$, more preferably at least 100 µmol $m^{-2}$ $s^{-1}$, still more preferably at least 250 µmol $m^{-2}$ $s^{-1}$ PAR (photosynthetic active radiation). Preferably said light has a light intensity of less than 2000 µmol $m^{-2}$ $s^{-1}$, preferably less than 1000 µmol $m^{-2}$ $s^{-1}$.

As used herein, the term "continuous light" means a photoperiod of more than 20 hours light per day, preferably more than 21 hours, preferably more than 22 hours, more preferably more than 23 hours and most preferably 24 hours. Short interruptions of a few minutes of this photoperiod may be comprised in continuous lighting. The total duration of the exposure to said light per day must be more than 20 hours.

As used herein, the term "continuous light tolerance" refers to a plant which, when grown under continuous light, exhibits a reduction in severity of at least one symptom of the complex of symptoms typically associated with continuous light intolerance as observed in normal non tolerant (tomato) plants of for instance the variety Moneyberg within 20 days after the first exposure to continuous light. Preferably, a plant which is tolerant to continuous light does not exhibit said at least one symptom after at least 3 weeks of exposure to continuous light. Even more preferably, said at least 3 weeks is at least four weeks. More preferably, it is at least 35, 42, 63 or 90 days. Preferably, said plant which is tolerant to continuous light has a higher chlorophyll concentration in its chlorophyll containing cells when exposed to continuous light than a non tolerant control plant which is exposed to the same conditions. Preferably, said plant which is tolerant to continuous light has a chlorophyll concentration of at least 35 (relative scale from 0-100, 100 is deep green), more preferably 36, 37, 38, 39, 40, 41, 42, 43, 44, 45, 46, 47, 48, 49, 50, 51, 52, 53, 54, 55, 56, 57, 58, 59, 60 as determined by a SPAD-502® (Konica Minolta) meter, wherein said plant has been exposed for at least, 33, 35, 42, 49, 53, 90 days to continuous light with a light intensity of 130 µmol $m^{-2}$ $s^{-1}$ from fluorescent tubes and grown at a temperature of 21° C. and a relative humidity between 60-80%, preferably 70%. In another preferred embodiment, said plant which is tolerant to continuous light has a chlorophyll concentration which is at least 5%, more preferably 10%, 15%, 20%, 25%, 30%, 35%, 40%, 50% higher than its sensitive parent plant exposed to the same conditions, as determined by using a SPAD-502® (Konica Minolta) meter, wherein said plant has been exposed for at least, 33, 35, 42, 49, 53, 90 days to continuous light with a light intensity of 130 µmol m$^2$ s$^{-1}$ from fluorescent tubes and grown at a temperature of 21° C. and a relative humidity between 60-80%, preferably 70%.

Said complex of symptoms includes but is not limited to leaf chlorosis, necrosis, decreased leaf development, increase in chloroplastic starch, decreased stem development, reduced photosynthesis, degreening and poor biomass production. Preferably all symptoms are absent in a plant tolerant to continuous light.

The term "leaf chlorosis" as used herein refers to a yellowing of leaf tissue due to absence of chlorophyll. The absence of chlorophyll can be visually observed as yellow spots on the leaf tissue.

The term "necrosis" as used herein refers to the premature death of cells and living tissue due to external factors. Necrosis can be visually observed as light to dark brown spots or absence of cells in tissue, preferably leaf tissue.

The term "decreased leaf development" as used herein refers to a decreased total surface area of the combined leaves of a plant which has been exposed to continuous light compared to the total surface area of the combined leaves of a comparable control plant which has not been exposed to continuous light. Total surface area of the combined leaves of a plant can be determined by measuring the total leaf surface area of a plant and/or by weighing the mass of the leaves of a plant.

The term "increase in chloroplastic starch" refers to an increase in the amount of starch in a sample comprising chloroplasts from a plant which has been exposed to continuous light compared to the amount of starch from a comparable sample of a comparable control plant which has not been exposed to continuous light. Alternatively, the increase of chloroplastic starch is determined by comparing the chloroplastic starch content of a plant or part thereof which contains chloroplasts with the chloroplastic starch content of a comparable control plant or chloroplast containing part thereof which has not been exposed to continuous light. The amount of starch of a plant is preferably determined by allowing a sample from said plant or part thereof which contains chloroplasts to gelatinize, incubating said sample with amyloglucosidase and subsequently determining the amount of glucose released. Preferably, said sample comprises isolated chloroplasts from said plant. The chloroplastic starch content is determined by calculating the amount of chloroplastic starch per kg of the plant.

The term "decreased stem development" as used herein refers to a decreased length and/or diameter of a stem of a plant or a part thereof which has been exposed to continuous light compared to the length and/or diameter of a comparable stem of a comparable control plant which has not been exposed to continuous light.

The term "reduced photosynthesis" as used herein refers to a reduced level of activity of photosynthesis in a plant or in a part thereof which has been exposed to continuous light compared to level of activity of photosynthesis in a comparable control plant which has not been exposed to continuous light. The term "photosynthesis" as used herein refers to the process in which the plant converts carbon dioxide into organic compounds using sunlight or artificial light as energy. The level of activity of photosynthesis can be determined by measuring the carbon dioxide uptake or oxygen production. A decrease in the carbon oxide uptake of a plant and/or in the oxygen production in comparison to a control plant indicates a decrease in the activity of photosynthesis.

The term "degreening" as used herein refers to the decrease in the content of chlorophyll in leaf tissue of a plant or in a part thereof which has been exposed to continuous light compared to a comparable control plant which has not been exposed to continuous light. Degreening can be visually observed as light green or whitened leaves. Alternatively, the content of chlorophyll in leaf tissue can be determined by performing a SPAD measurement well known in the art and compare the chlorophyll measurements performed in leaf tissue of said control plant and establish whether the content of chlorophyll is decreased.

The term "poor biomass production" as used herein refers to a lower (e.g. at least 5%, 10%, 15% lower) amount of biomass of a plant which has been exposed to continuous light compared to a comparable control plant which has not been exposed to continuous light. The biomass of a plant can be determined by measuring the fresh and/or dry weight of a plant.

As used herein, the term "allele(s)" means any of one or more alternative forms of a gene, all of which alleles relate to at least one trait or characteristic. In a diploid cell or organism, the two alleles of a given gene occupy corresponding loci on a pair of homologous chromosomes. Since the present invention relates to genes, i.e. genomic regions that may comprise one or more genes, but also regulatory sequences, it is in some instances more accurate to refer to "haplotype" (i.e. an allele of a chromosomal segment) instead of "allele", however, in those instances, the term "allele" should be understood to comprise the term "haplotype".

A "gene" is defined herein as a hereditary unit consisting of a sequence of DNA that occupies a specific location on a chromosome and that contains the genetic instruction for a particular characteristics or trait in an organism.

A "locus" is defined herein as the position that a given gene occupies on a chromosome of a given species.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes.

As used herein, the term "hybrid" means any offspring of a cross between two genetically unlike individuals, including but not limited to the cross between two inbred lines.

As used herein, the term "inbred" means a substantially homozygous individual or line In this application a "recombination event" is understood to mean a meiotic crossing-over.

As used herein, the terms "introgression", "introgressed" and "introgressing" refer to both a natural and artificial process whereby genes of one species, variety or cultivar are moved into the genome of another species, variety or cultivar, by crossing those species, varieties or cultivars. The process may optionally be completed by backcrossing to the recurrent parent.

"Genetic engineering", "transformation" and "genetic modification" are all used herein as synonyms for the transfer of isolated and cloned genes into the DNA, usually the chromosomal DNA or genome, of another organism.

As used herein, the term "plant part" indicates a part of the tomato plant, including single cells and cell tissues such as plant cells that are intact in plants, cell clumps and tissue cultures from which tomato plants can be regenerated.

Examples of plant parts include, but are not limited to, single cells and tissues from pollen, ovules, leaves, embryos, roots, root tips, anthers, flowers, fruits, stems shoots, and seeds; as well as pollen, ovules, leaves, embryos, roots, root tips, anthers, flowers, fruits, stems, shoots, scions, rootstocks, seeds, protoplasts, calli, and the like.

As used herein, the term "population" means a genetically heterogeneous collection of plants sharing a common genetic derivation.

As used herein, the term "tomato" means any plant, line or population formerly known under the genus name of *Lycopersicon*, including but not limited to *Lycopersicon cerasiforme, Lycopersicon cheesmanii, Lycopersicon chilense, Lycopersicon chmielewskii, Lycopersicon esculentum* (now *Solanum lycopersicum*), *Lycopersicon hirsutum, Lycopersicon parviflorum, Lycopersicon pennellii, Lycopersicon peruvianum, Lycopersicon* pimpinellifolium, or *Solanum lycopersicoides*. The newly proposed scientific name for *Lycopersicon esculentum* is *Solanum lycopersicum*. Similarly, the names of the wild species has been altered. *L. pennellii* has become *Solanum pennellii, L. hirsutum* has become *S. habrochaites, L. peruvianum* has be split into S. 'N. peruvianum' and S. 'Callejon de Huayles', *S. peruvianum*, and *S. corneliomuelleri, L. parviflorum* has become *S. neorickii, L. chmielewskii* has become *S. chmielewskii, L. chilense* has become *S. chilense, L. cheesmaniae* has become *S. cheesmaniae* or *S. galapagense*, and *L. pimpinellifolium* has become *S. pimpinellifolium* (Solanacea Genome Network (2005) Spooner and Knapp).

The term "*S. lycopersicum*", as used herein, refers to any variety or cultivar of the garden tomato.

It is especially noted that *S. habrochaites* can be defined as a tomato species that carries hairy fruits, while *S. lycopersicum* is a tomato species carrying hairless fruits.

As used herein, the term "variety" or "cultivar" means a group of similar plants that by structural or genetic features and/or performance can be distinguished from other varieties within the same species.

The term "gene associated with tolerance to continuous light" as well as the shorter term "gene for continuous light tolerance" refer to a region located on a particular chromosome of tomato that is associated with at least one gene that encodes for continuous light-tolerance or at least a regulatory region, i.e. a region of a chromosome that controls the expression of one or more genes involved in tolerance to continuous light. The phenotypic expression of that gene may for instance be observed as a reduced degree of chlorosis or an improved biomass production upon exposure to continuous light. A gene may for instance comprise one or more genes of which the products confer the genetic continuous light tolerance. Alternatively, a gene may for instance comprise regulatory genes or sequences of which the products influence the expression of genes on other loci in the genome of the plant thereby conferring the tolerance to continuous light. The gene of the present invention may be defined by indicating their genetic location in the genome of the respective wild tomato accession using one or more molecular genomic markers. One or more markers, in turn, indicate a specific locus. Distances between loci are usually measured by frequency of crossing-over between loci on the same chromosome. The farther apart two loci are, the more likely that a crossover will occur between them. Conversely, if two loci are close together, a crossover is less likely to occur between them. As a rule, one centimorgan (cM) is equal to 1% recombination between loci (markers). When a gene can be indicated by multiple markers the genetic distance between the end-point markers is indicative of the size of the gene. It is to be understood that the genes identified herein as residing in the CLT locus (see Tables 2 and 3) may be used as markers for the continuous light resistance trait in aspects of this invention. In particular, polymorphisms in these genes between the tolerant and non-tolerant phenotype are envisioned.

The term "natural genetic background" is used herein to indicate the original genetic background of a gene. Such a background may for instance be the genome of a continuous light-tolerance wild accession of tomato. For instance, the gene of the present invention was found at specific locations on chromosomes 7 of *Solanum pennellii* 0716. As an example, the *Solanum pennellii* 0716 represents the natural genetic background of the genes on chromosomes 7 of *Solanum pennellii* 0716. Conversely, a method that involves the transfer of DNA comprising the gene, or a tolerance-conferring part thereof, from chromosome 7 of *Solanum pennellii* 0716 to the same position on chromosome 7 of another tomato species, will result in that gene, or said tolerance-conferring part thereof, not being in its natural genetic background.

The terms "determinate" and "indeterminate" as used herein refers to the type of growth habit of tomato plants, which is commonly classified as determinate or indeterminate. This classification depends preferably on the capacity of the shoot system for continued sympodial growth. The terms are used in their art-recognized meaning.

The term "standard practice conditions", "standard greenhouse conditions" and "standard conditions" refer to the conditions of light, humidity, temperature, etc. where under plants are grown or incubated, for instance for the purpose of phenotypic characterization, as being standard. For greenhouses or climate chambers for instance, this refers to 8-16-h day, 15° C.-25° C. More in general, the terms refer to standard and reference growth conditions with a photoperiod of 8 to 24 h (photosynthetic photon flux (PPF) 25 to 1000 $\mu mol\ m^{-2}\ s^{-1}$), preferably a light regime of 16 hours light and 8 hours dark, an air temperature of about 21° C. during the day and 18° C. at night, a water vapour pressure deficit of about 4.4 g $m^{-3}$ corresponding to a relative humidity (RH) of about 60%-85%, at 400-900 ppm $CO_2$ and atmospheric $O_2$ concentration and at atmospheric air pressure (generally 1008 hPa). Water and nutrients may be given drop wise near the stem, or in the form of spray or mist or by ebb and flow.

With the term "bioassay for measuring the capability of growing in continuous light" as used herein, is meant any bioassay which is suitable for determining differences in said symptoms. Preferably, chlorosis is determined using fluorescence measurements of the chlorophyll concentration using a SPAD® measuring device Marquard and Tipton 1987, HortScience 22: 1327. Standard bioassay experimentation conditions, such as stem diameter and plant height measurements, chlorophyll concentration measurements and assays for determining tolerance to continuous light are further specified in the Examples below.

The term "marker-assisted selection", as used herein, refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

The term "marker", as used herein, refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, cleaved amplified polymorphic sequence (CAPS) markers or isozyme markers or combinations of the markers described herein which defines a specific genetic and chromosomal location.

The term "linked", as used herein, with reference to markers linked to a trait, refers to a marker the presence of which in the genome of the plant coincides with the presence of the trait. Usually the term refers to a genetic marker that falls within the physical boundaries of a genomic region spanned by at least two markers. For RIL (recombinant inbred lines), such markers having established LOD scores above a certain threshold thereby indicating that no or very little recombination between these markers and the trait locus occurs in crosses; as well as any marker in linkage disequilibrium to the trait locus; as well as markers that represent the actual causal mutations within the trait locus. The term "linked" is used in its broadest sense and indicates that the marker and the gene are located within a continuous DNA sequence of several centiMorgan. The term is used herein with reference to the linkage between markers and phenotype and refers to a distance of preferably less than 20 cM, preferably less than 10 cM, still more preferably less than 6, 5, 4, 3, 2, or 1 cM.

The term "gene", as used herein, refers to a hereditary unit consisting of a sequence of DNA that occupies a specific location on a chromosome and that contains the genetic instruction for a particular characteristics or trait in an organism. The term "gene" thus refers to a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (for example, enzymatic activity, ligand binding, signal transduction, etc.) of the polypeptide are retained. The term "gene" encompasses both cDNA and genomic forms of a gene.

The term 'yield' as used herein, refers to the biomass of a tomato plant. Any parameter which is related to the biomass of said plant can be used to determine the yield of a plant. Preferably, said parameter comprises the total leaf area, the shoot dry matter, the shoot fresh mass, the dry mass or the shoot dry mass of said plant.

For optimal growth, fruit vegetables like tomato need 6 hours of darkness per day. This implies that no photosynthesis occurs for 33% per day. If these vegetables could be grown under continuous light, a substantial increase in production would be expected. However, continuous light causes severe problems in these crops: tomato plants, grown in continuous light show a strong increase in chloroplastic starch, leaf chlorosis, necrosis and consequently very poor biomass production; continuous light can even be lethal for the crop.

The present inventors have now discovered tolerant lines in several wild species and in an old cultivar. However, tolerant lines could not be found in any of the modern tomato varieties like Encore, Campari, DRS540, Tourance, Westland, etc.

There are no published reports of tomato varieties exhibiting tolerance to continuous light, save a congress abstract of a miniature tomato cultivar. There is no report on the sensitivity of other tomato species to continuous light, except for the paper of Daskaloff and Ognjanova (Zeitschrift für Pflanzenzuchtung 1965 54: 169-181) where it is claimed that *S. habrochaites, S. peruvianum* and *S. racemigerum* (=*pimpinellifolium*) are tolerant to continuous light. It is remarkable that in this publication the focus is on experiments at low light intensities as it is described that the continuous light symptoms are more profound at these lower light intensities. *S. pimpinellifolium* was found to be tolerant by Daskaloff and Ognjanova. In contrast, the present inventors have now found that it is just the opposite and that the continuous light symptoms are more profound at higher light intensities, and *S. pimpinellifolium* was not found to be tolerant.

In the experiments as conducted natural variation in the continuous light symptoms was sought. Several tomato species are clearly tolerant. The symptoms are quantified by measuring the chlorophyll concentration (using e.g., a SPAD® meter). For some symptomless lines biomass production increased linearly with the increase of available light. Moreover, in addition to a linear increase some lines showed even a further increase in biomass production relative to the light available, i.e. higher than was predicted. The wild tomato donors *pennellii* LA716, *S. peruvianum* LA1708, *S. habrochaites* LA1777, G1560, Lyc4, *S. chmielewskii* LA1840, *S. neorickii* LA2133, *S. chilense* LA1959 are tolerant to continuous light the same is true for an old variety "Sub arctic plenty". Tolerance lines do not show deleterious symptoms.

The IL lines, 4 and 5 *S. pennellii*\*M82, 42 and 43 *S. neorickii* (LA2133), 5 *S. chilense* (LA1959) are tolerant to continuous light.

The chromosomal location of the tolerance is chromosome 7 for the *S. pennellii*, *S. neorickii*, and *S. chilense* source.

Producing Plants with Tolerance to Continuous Light

Plant breeders and in particular seed companies employ elite breeding lines, generally referred to as "elite lines" to provide a constant quality product. The elite lines are the result of many years of inbreeding and combine multiple superior characteristics such as high yield, fruit quality, and resistance to pests, disease, or tolerance to abiotic stress. The average yield of these elite lines is generally much higher than the original wild (landrace) accessions from which many of the modern tomato varieties are descendants. The elite lines can be used directly as crop plant, but are typically used to produce so-called F1 or single-cross hybrids, produced by a cross between two (homozygous or inbred) elite lines. The F1 hybrids thus combine the genetic properties of the two parents into a single plant. An add-on benefit of hybrids is that they express hybrid vigour or heterosis, the poorly understood phenomenon that hybrid plants grow better than either (inbred) parent and show higher yields.

Backcross or pedigree selection is one method by which breeders add desirable agronomic traits to their elite breeding lines. The method involves crossing the breeding line with a line that expresses the desirable trait followed by backcrossing offspring plants expressing the trait to the recurrent parent. As a result, the selection of an individual as a parent in a breeding program is based on the performance of its forebears. Such methods are most effective in breeding for qualitatively-inherited traits, i.e traits which are present or absent.

Recurrent selection is an alternative breeding method for improving breeding lines and involves systematic testing and selection of desirable progeny followed by recombination of the selected individuals to form a new population. Recurrent selection has proven effective for improving quantitative traits in crop plants. Recurrent selection, however, decreases the rate of broadening genetic basis underlying the various traits in a breeding program, and its potential is therefore limited.

The present inventors discovered that the yield of a tomato plant may be increased by introgressing into an elite breeding line the trait of tolerance to continuous light.

A first method would comprise introgressing the trait from a tomato plant exhibiting tolerance to continuous light, such as a plant of the wild tomato species *S. pennellii*, such as *S. pennellii* LA716, or an offspring plant thereof having said tolerance to continuous light, into a plant of a tomato line of interest. This may for instance be achieved by crossing a plant of a recipient breeding line of *S. lycopersicum* capable of producing commercially valuable fruits, with a plant of a donor line of a tomato species, having tolerance to continuous light. This will result in a situation wherein the gene for tolerance to continuous light is in the genetic background of the tomato line of interest. The establishment of the proper introgression in offspring plants may be monitored by using specific markers as defined herein.

Recombination is the exchange of information between two homologous chromosomes during meiosis. In a recombinant plant, DNA that is originally present on a specific location within the chromosome is exchanged for DNA from another plant (i.e. maternal for paternal or vice versa). In order to exchange only the required material, and maintain the valuable original information on the chromosome as much as possible, will usually require two crossover events. The normal way to find such a recombinant is to screen a population of F2-plants. This population must be of sufficient size in order to detect the rare (low frequency) double recombinants. The frequency of recombination can be expressed in a genetic distance. For instance, a single recombinant in a 10 cM area can be found with a frequency of 10% (1 centimorgan is defined as 1% recombinant progeny in a testcross).

The present invention also provides methods of producing the plants of the invention using marker assisted selection (MAS). The invention therefore relates to methods of plant breeding and to methods to select plants, in particular tomato plants, particularly cultivated tomato plants as breeder plants for use in breeding programs or cultivated tomato plants for having desired genotypic or potential phenotypic properties, in particular related to producing quantities of valuable tomato fruits, also referred herein to as agronomically desirable plants. Herein, a cultivated plant is defined as a plant being purposely selected or having been derived from a plant having been purposely selected in agricultural or horticultural practice for having desired genotypic or potential phenotypic properties, in particular a plant obtained by inbreeding.

Since the gene can only be properly identified phenotypically when the plant remains healthy when subjected to continuous light, it is of particular advantage that the establishment of the proper introgression in offspring plants may be monitored by using the gene-specific markers as provided herein, either in cis or in trans coupling as explained below. By using marker assisted selection (MAS) or marker assisted breeding (MAB) methods, the skilled person is therefore provided with methods for selecting plants carrying the desired genotype loci and discarding plants lacking the potential of producing progeny tolerant to continuous light.

The present invention thus also provides methods for selecting a tomato plant exhibiting tolerance to continuous light, comprising detecting in said plant the presence of the gene for tolerance to continuous light as defined herein. In a preferred method of the invention for selecting such a plant the method comprises:

a) providing a sample of genomic DNA from a tomato plant;

b) detecting in said sample of genomic DNA at least one molecular marker linked to the gene for tolerance to continuous light.

The step of providing a sample of genomic DNA from a tomato plant may be performed by standard DNA isolation methods well known in the art.

The step of detecting a molecular marker (step b) may, in a preferred embodiment, comprise the use of CAPS markers, which constitute a set of bi-directional primers in combination with a restriction enzyme. This allows for the detection of specific SNPs linked to the trait. Bi-directional means that the orientation of the primers is such that one functions as the forward and one as the reverse primer in an amplification reaction of nucleic acid.

Alternatively, the step of detecting a molecular marker (step b) may in another preferred embodiment, comprise the use of a nucleic acid probe having a base sequence which is substantially complementary to the nucleic acid sequence defining said molecular marker (e.g. said SNP) and which nucleic acid probe specifically hybridizes under stringent conditions with a nucleic acid sequence defining said molecular marker. A suitable nucleic acid probe may for instance be a single strand oligonucleotide of the amplification product corresponding to the marker.

The step of detecting a molecular marker (step b) may also comprise the performance of a unique nucleic acid amplification reaction on said genomic DNA to detect said gene. This can suitably be done by performing a PCR reaction using a pair of marker-specific primers based on the internal or adjacent (up to 500 kilo base) sequence. In a preferred embodiment, said step b) comprises the use of at least one pair of primers defining a marker for said gene (e.g. being complementary to said marker or hybridizing specifically to said marker or allowing polymerase chain extension to occur when bound to said marker), or a pair of primers which specifically hybridize under stringent conditions with the nucleic acid sequence of a marker for said gene.

The step of detecting an amplified DNA fragment having a certain predicted length or a certain predicted nucleic acid sequence may be performed such that the amplified DNA fragment has a length that corresponds (plus or minus a few bases, e.g. a length of one, two or three bases more or less) to the expected length as based on the nucleotide sequence of the genes and markers identified herein. The skilled person is aware that markers that are absent in plants having the introgression as defined herein (donor plants), while they are present in the plants receiving the introgression (recipient plants) (so-called trans-markers), may also be useful in assays for detecting the introgression among offspring plants, although detecting the presence of a specific introgression is not optimally demonstrated by the absence of a marker.

The step of detecting an amplified DNA fragment having the predicted length or the predicted nucleic acid sequence may be performed by standard gelelectrophoresis techniques, real time PCR, or by using DNA sequencers. The methods need not be described here as they are well known to the skilled person. It should be noted that a marker is usually defined based on its nucleotide sequences in combination with its position relative to other markers on a linkage map.

Molecular Markers and Genes

Molecular markers are used for the visualisation of differences in nucleic acid sequences. This visualisation is possible due to DNA-DNA hybridisation techniques after digestion with a restriction enzyme (RFLP) and/or due to techniques using the polymerase chain reaction (e.g. STS, microsatellites, AFLP). All differences between two parental genotypes will segregate in a mapping population (e.g., $BC_1$, $F_2$) based on the cross of these parental genotypes. The segregation of the different markers may be compared and recombination frequencies can be calculated. The recombination frequencies of molecular markers on different chromosomes is generally 50%. Between molecular markers located on the same chromosome the recombination frequency depends on the distance between the markers. A low recombination frequency corresponds to a short genetic distance between markers on a chromosome. Comparing all recombination frequencies will result in the most logical order of the molecular markers on the chromosomes. This most logical order can be depicted in a linkage map. A group of adjacent or contiguous markers on the linkage map that is associated with tolerance to continuous light, pinpoints the position of a gene associated with tolerance to continuous light.

The markers identified herein may be used in various aspects of the invention as will now be illustrated. Aspects of the invention are not limited to the use of the markers identified herein. It is stressed that the aspects may also make use of markers not explicitly disclosed herein or even yet to be identified.

In the present invention amplified fragment length polymorphism (AFLP) markers, single nucleotide polymorphisms (SNPs), and insertion deletions (INDELs), microsatellite markers, restriction fragment length polymorphism (RFLP) markers, sequence-characterized amplified region (SCAR) markers, cleaved amplified polymorphic sequence (CAPS) markers or isozyme markers or combinations of these markers might be used.

In general, a gene may span a region of several hundreds to thousands of bases. The plants that have the genetic potential for exhibiting a particular phenotypic trait (tolerance to continuous light) may be traced amongst a population of offspring plants through the observed correlation between the presence of a (string of contiguous) genomic marker(s) and the presence of the phenotypic trait. By providing a non-limiting list of markers, the present invention thus provides for the effective utility of the gene in a breeding program.

It is further important to note that the contiguous genomic markers can also be used to indicate the presence of the gene (and thus of the phenotype) in an individual plant, i.e. they can be used in marker assisted selection (MAS) procedures. In principle, the number of potentially useful markers is limited but may be very large, and the skilled person may easily identify additional markers to those mentioned in the present application. Any marker that is linked to the gene, e.g. falling within the physical boundaries of the genomic region spanned by the markers, wherein between said markers and the gene no or very little recombination occurs in crosses; as well as any marker in linkage disequilibrium to the gene; as well as markers that represent the actual causal mutations within the gene, may be used in MAS procedures.

This means that the markers identified herein, are mere examples of markers suitable for use in MAS procedures. Moreover, when the gene, or the specific trait-conferring part thereof, is introgressed into another genetic background (i.e. into the genome of another plant line), then some markers may no longer be found in the offspring although the trait is present therein, indicating that such markers are outside the genomic region that represents the specific trait-conferring part of the gene in the original parent line only and that the new genetic background has a different genomic organisation. Such markers of which the absence indicates the successful introduction of the genetic element in the offspring are called "trans markers" and may be equally suitable in MAS procedures under the present invention.

Upon the identification of the gene, the gene effect (tolerance to continuous light) is confirmed by determining the tolerance to continuous light of progenies respectively recombinant or segregating for the genes under investigation. Preferably, detecting the presence of a gene of the invention is performed with at least one of the markers for a gene as defined herein. The present invention therefore also relates to a method for detecting the presence of a gene for tolerance to continuous light as defined herein in tomato by the use of the said markers.

The nucleotide sequence of the genes of the present invention may be resolved by determining the nucleotide sequence of one or more markers associated with said gene and designing internal primers for said marker sequences that may then be used to further determine the sequence the gene adjacent to said marker sequences. For instance the nucleotide sequence of CAPS markers may be obtained by isolating said markers from the electrophoresis gel used in the determination of the presence of said markers in the genome of a subject plant, and determining the nucleotide sequence of said markers by for instance Sanger or pyro sequencing methods, well known in the art.

In embodiments of methods for detecting the presence of a gene in a tomato plant, the method may also comprise the steps of providing an oligonucleotide or polynucleotide capable of hybridizing under stringent hybridization conditions to a nucleic acid sequence of a marker linked to said gene, contacting said oligonucleotide or polynucleotide with nucleic acid of a tomato plant, and determining the presence of specific hybridization of said oligonucleotide or polynucleotide to said nucleic acid.

Preferably said method is performed on a nucleic acid sample obtained (isolated) from said tomato plant, although in situ hybridization methods may also be employed. Alternatively, and in a more preferred embodiment, the skilled person may, once the nucleotide sequence of the gene has been determined, design specific hybridization probes or oligonucleotides capable of hybridizing under stringent hybridization conditions to the nucleic acid sequence of said gene and may use such hybridization probes in methods for detecting the presence of a gene of the invention in a tomato plant.

Production of Tomato Plants Exhibiting Tolerance to Continuous Light by Transgenic Methods According to another aspect of the present invention, a nucleic acid (preferably DNA) sequence comprising one or more of the genes as defined herein may be used for the production of a tomato plant exhibiting tolerance to continuous light. In this aspect, the invention provides for the use of genes as defined herein or tolerance to continuous light-conferring parts thereof, for producing a tomato plant tolerant to continuous light as defined herein, which use involves the introduction of a nucleic acid sequence comprising said gene in a suitable recipient plant. As stated, said nucleic acid sequence may be derived from a suitable donor plant. A suitable source according to the present invention for the gene for tolerance to continuous light is tomato line S. pennellii LA716 (PI 246502 available from the Agricultural Research Service (ARS-GRIN) of the US Department of Agriculture, Washington D.C., USA), S. neorickii, S habrochaites, S. lycopersicum, S peruvianum or S. chemielewskii.

Preferably, said gene is selected from the genes present listed in Table 2. The gene sequences thereof are provided in for Table 3.

Preferably said gene is SL1.00sc07408_313.1.1.

In an alternative or additional preferred embodiment, said gene is SL1.00sc07408_312.1.1.

In an alternative or additional preferred embodiment, said gene is SL1.00sc07408_311.1.1.

In an alternative or additional preferred embodiment, said gene is SL1.00sc07408_310.1.1.

In an alternative or additional preferred embodiment, said gene is SL1.00sc07408_309.1.1.

In an alternative or additional preferred embodiment, said gene is SL1.00sc07408_308.1.1.

In an alternative or additional preferred embodiment, said gene is SL1.00sc07408_307.1.1.

In an alternative or additional preferred embodiment, said gene is SL1.00sc07408_306.1.1.

In an alternative or additional preferred embodiment, said gene is SL1.00sc07408_305.1.1.

In an alternative or additional preferred embodiment, said gene is SL1.00sc07408_304.1.1.

In an alternative or additional preferred embodiment, said gene is SL1.00sc07408_303.1.1.

In an alternative or additional preferred embodiment, said gene is SL1.00sc07408_302.1.1.

In an alternative or additional preferred embodiment, said gene is SL1.00sc07408_301.1.1.

In an alternative or additional preferred embodiment, said gene is SL1.00sc07408_300.1.1.

In an alternative or additional preferred embodiment, said gene is SL1.00sc07408_299.1.1.

In an alternative or additional preferred embodiment, said gene is SL1.00sc07408_298.1.1.

In an alternative or additional preferred embodiment, said gene is SL1.00sc07408_297.1.1.

In an alternative or additional preferred embodiment, said gene is SL1.00sc07408_296.1.1.

In an alternative or additional preferred embodiment, said gene is SL1.00sc07408_295.1.1.

In an alternative or additional preferred embodiment, said gene is SL1.00sc07408_294.1.1.

In an alternative or additional preferred embodiment, said gene is SL1.00sc07408_293.1.1.

In an alternative or additional preferred embodiment, said gene is SL1.00sc07408_292.1.1.

In an alternative or additional preferred embodiment, said gene is SL1.00sc07408_291.1.1.

In an alternative or additional preferred embodiment, said gene is SL1.00sc07408_290.1.1.

In an alternative or additional preferred embodiment, said gene is SL1.00sc07408_289.1.1.

In an alternative or additional preferred embodiment, said gene is SL1.00sc07408_288.1.1.

In an alternative or additional preferred embodiment, said gene is SL1.00sc07408_287.1.1

In a preferred embodiment, said gene is a gene located between markers 7-20-1 and 7-20-2 as listed in Table 2. Most preferably, said gene is SL1.00sc07408_301.1.1.

The nucleic acid sequence that comprises a gene for tolerance to continuous light, or a tolerance to continuous light-conferring part thereof, may be transferred to a suitable recipient plant by any method available. For instance, the said nucleic acid sequence may be transferred by crossing a plant of line PI 246502 with a selected breeding line which is not tolerant to continuous light or of which the tolerance is to be improved, i.e. by introgression, by transformation, by protoplast fusion, by a doubled haploid technique or by embryo rescue or by any other nucleic acid transfer system, optionally followed by selection of offspring plants comprising the gene for tolerance to continuous light (as assessed by markers) and/or exhibiting tolerance to continuous light. For transgenic methods of transfer a nucleic acid sequence comprising a gene for tolerance to continuous light may be isolated from said donor plant by using methods known in the art and the thus isolated nucleic acid sequence may be transferred to the recipient plant by transgenic methods for plant transformation, for instance by means of a vector, in a gamete, or in any other suitable transfer element, such as a bombardment with a particle coated with said nucleic acid sequence.

Plant transformation generally involves the construction of a vector with an expression cassette that will function in plant cells. In the present invention, such a vector consists of a nucleic acid sequence that comprises a gene for tolerance to continuous light, which vector may comprise such a gene that is under control of or operatively linked to a regulatory element, such as a promoter. The expression vector may contain one or more such operably linked gene/regulatory element combinations, provided that at least one of the genes contained in the combinations confers tolerance to continuous light. The vector(s) may be in the form of a plasmid, and can be used, alone or in combination with other plasmids, to provide transgenic plants that exhibit tolerance to continuous light, using transformation methods known in the art, such as the *Agrobacterium* transformation system.

Expression vectors can include at least one marker gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the marker gene). Many commonly used selectable marker genes for plant transformation are known in the art, and include, for example, genes that code for enzymes that metabolically detoxify a selective chemical agent which may be an antibiotic or a herbicide, or genes that encode an altered target which is insensitive to the inhibitor. Several positive selection methods are known in the art, such as mannose selection. Alternatively, marker-less transformation can be used to obtain plants without mentioned marker genes, the techniques for which are known in the art.

One method for introducing an expression vector into a plant is based on the natural transformation system of *Agrobacterium* (See e.g. Horsch et al., 1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant. Methods of introducing expression vectors into plant tissue include the direct infection or co-cultivation of plant cells with *Agrobacterium tumefaciens*. Descriptions of *Agrobacterium* vectors systems and methods for *Agrobacterium*-mediated gene transfer are provided in U.S. Pat. No. 5,591,616. General descriptions of plant expression vectors and reporter genes and transformation protocols and descriptions of *Agrobacterium* vector systems and methods for *Agrobacterium*-mediated gene transfer can be found in Gruber and Crosby, 1993. General methods of culturing plant tissues are provided for example by Miki et al., 1993 and by Phillips, et al., 1988. A proper reference handbook for molecular cloning techniques and suitable expression vectors is Sambrook and Russell, 2001.

Another method for introducing an expression vector into a plant is based on microprojectile-mediated transformation (particle bombardment) wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes. Another method for introducing DNA to plants is via the sonication of target cells. Alternatively, liposome or spheroplast fusion has been used to introduce expression vectors into plants. Direct uptake of DNA into protoplasts using $CaCl_2$ precipitation, polyvinyl alcohol or poly-L-ornithine has also been reported. Electroporation of protoplasts and whole cells and tissues has also been described.

Other well known techniques such as the use of BACs, wherein parts of the tomato genome are introduced into bacterial artificial chromosomes (BACs), i.e. vectors used to clone DNA fragments (100- to 300-kb insert size; average, 150 kb) in *Escherichia coli* cells, based on naturally occurring F-factor plasmid found in the bacterium *E. coli* may for instance be employed in combination with the BIBAC system to produce transgenic plants.

Following transformation of tomato target tissues, expression of the above described selectable marker genes allows for preferential selection of transformed cells, tissues and/or plants, using regeneration and selection methods now well known in the art.

Production of Tomato Plants Exhibiting Tolerance to Continuous Light by Non-Transgenic Methods In an alternative embodiment for producing a tomato plant exhibiting tolerance to continuous light, protoplast fusion can be used for the transfer of nucleic acids from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell, that may even be obtained with plant species that cannot be interbreeded in nature, is tissue cultured into a hybrid plant exhibiting the desirable combination of traits. More specifically, a first protoplast can be obtained from a tomato plant of accession PI 246502. A second protoplast can be obtained from a second tomato plant variety, preferably a tomato line that comprises commercially valuable characteristics, such as, but not limited to disease resistance, insect resistance, valuable fruit characteristics, etc. The protoplasts are then fused using traditional protoplast fusion procedures, which are known in the art.

Alternatively, embryo rescue may be employed in the transfer of a nucleic acid comprising the gene as described herein from a donor plant to a recipient plant. Embryo rescue can be used as a procedure to isolate embryo's from crosses wherein plants fail to produce viable seed. In this process, the fertilized ovary or immature seed of a plant is tissue cultured to create new plants.

The present invention also relates to a method for improving the tolerance to continuous light of a plant of a tomato breeding line, comprising the steps of:

a) crossing a plant of a tomato breeding line with a plant of tomato line PI 246502 or an offspring plant thereof harbouring the gene for tolerance to continuous light as described herein;

b) selecting a progeny tomato plant resulting from said crossing having an introgression from tomato accession PI 246502 or an offspring plant thereof associated with tolerance to continuous light;

c) selfing and/or backcrossing said progeny tomato plant selected in step (b) using said tomato breeding line as a recurrent parent;

d) selecting a progeny tomato plant resulting from the selfing or backcrossing in step (c) having an introgression from tomato accession PI 246502 or an offspring plant thereof associated with tolerance to continuous light, e) repeating said steps of selfing and/or backcrossing and selection of steps (c) and (d) to provide a plant of a tomato breeding line essentially homozygous for said introgression, wherein preferably at least one selection as performed in steps (b) or (d) is performed by marker-assisted selection.

In a preferred embodiment of such a method, said tomato breeding line is an elite line.

In an alternative preferred embodiment of the above method, the marker-assisted selection procedure comprises the selection for at least one marker as exemplified in the Examples below.

The introgression of the nucleic acid sequence comprising the gene for tolerance to continuous light as described herein may suitably be accomplished by using traditional breeding techniques. The gene is preferably introgressed into commercial tomato varieties by using marker-assisted selection (MAS) or marker-assisted breeding (MAB). MAS and MAB involves the use of one or more of the molecular markers for the identification and selection of those offspring plants that contain one or more of the genes that encode for the desired trait. In the present instance, such identification and selection is based on selection of the gene of the present invention or markers associated therewith. MAS can also be used to develop near-isogenic lines (NIL) harboring the gene of interest, or the generation of gene isogenic recombinants (QIRs), allowing a more detailed study of each gene effect and is also an effective method for development of backcross inbred line (BIL) populations. Tomato plants developed according to this embodiment can advantageously derive a majority of their traits from the recipient plant, and derive tolerance to continuous light from the donor plant.

Crossing can be achieved by mechanically pollinating the female flower of one parent plant with pollen obtained from male flowers of another parent plant.

As discussed briefly above, traditional breeding techniques can be used to introgress a nucleic acid sequence encoding a gene for tolerance to continuous light into a recipient tomato plant requiring tolerance to continuous light. In one method, which is referred to as pedigree breeding, a donor tomato plant that exhibits tolerance to continuous light and comprising a nucleic acid sequence encoding for the gene associated with tolerance to continuous light as defined herein is crossed with a recipient tomato plant (preferably a plant of an elite line) that exhibits agronomically desirable characteristics, such as, but not limited to, disease (e.g. TMV) resistance, insect resistance, valuable fruit characteristics, etc., but which is not tolerance to continuous light, or which requires improvement of such tolerance. The resulting plant population (representing the $F_1$ hybrids) is then self-pollinated and set seeds ($F_2$ seeds). The $F_2$ plants grown from the $F_2$ seeds are then screened for tolerance to continuous light. The population can be screened in a number of different ways.

First, the population can be screened using a bioassay wherein the plant is grown under continuous light for a prolonged period of time and its health or productivity (phenotype) is inspected. Second, marker-assisted selection can be performed using one or more of the hereinbefore-described molecular markers to identify those progeny that comprise a nucleic acid sequence encoding a gene for tolerance to continuous light as defined herein. Other methods, described above by methods for detecting the presence of a gene may be used. Also, marker-assisted selection can be used to confirm the results obtained from the phenotype scores, and therefore, several methods may also be used in combination.

Inbred tomato plant lines exhibiting tolerance to continuous light can be developed using the techniques of recurrent selection and backcrossing, selfing and/or dihaploids or any other technique used to make parental lines. In a method of recurrent selection and backcrossing, the tolerance to continuous light-conferring genetic element as disclosed herein can be introgressed into a target recipient plant (the recurrent parent) by crossing the recurrent parent with a first donor plant, which differs from the recurrent parent and is referred to herein as the "non-recurrent parent". The recurrent parent is a plant of which the tolerance is to be improved and possesses agronomically desirable characteristics, such as, but not limited to disease resistance, insect resistance, valuable fruit characteristics, etc. The non-recurrent, or donor, parent may suitably be a plant of suitable donor line as described herein which comprises a nucleic acid sequence that encodes for a gene that confers tolerance to continuous light. Alternatively, the donor parent can be any plant variety or inbred line that is cross-fertile with the recurrent parent and has acquired the gene for tolerance to continuous light in an earlier cross with a plant of the said donor line. The progeny resulting from a cross between the recurrent parent and non-recurrent parent is backcrossed to the recurrent parent. The resulting plant population is then screened for the desired characteristics, which screening may occur in a number of different ways. For instance, the population can be screened using phenotypic screens as described herein. As an alternative to phenotypic assays, marker-assisted selection (MAS) can be performed using one or more of the hereinbefore described molecular markers, hybridization probes or polynucleotides to identify progeny that comprise a nucleic acid sequence encoding the gene responsible for tolerance to continuous light.

Following screening, the $F_1$ hybrid plants that exhibit a tolerant phenotype or, more preferably, genotype and thus comprise the requisite nucleic acid sequence encoding for a gene conferring tolerance to continuous light are then selected and backcrossed to the recurrent parent for a number of generations in order to allow for the tomato plant to become increasingly elite. This process can be performed for two to five or more, such as 6, 7 or 8 generations. In principle the progeny resulting from the process of crossing the recurrent parent with the non-recurrent parent are heterozygous for one or more genes that encode for tolerance to continuous light.

In a preferred embodiment, a method of introducing a desired trait into a hybrid tomato variety comprises the steps of:

(a) crossing an inbred tomato parent with another tomato plant that comprises one or more desired traits, to produce F1 progeny plants, wherein the desired trait is tolerance to continuous light as conferred by the gene from any suitable donor plant of the said trait as defined herein, or an offspring plant thereof;

(b) selecting said F1 progeny plants that have the desired trait to produce selected F1 progeny plants, preferably using molecular markers as defined herein;

(c) backcrossing the selected progeny plants with said inbred tomato parent plant to produce backcross progeny plants;

(d) selecting for backcross progeny plants that have the desired trait (tolerance to continuous light) and morphological and physiological characteristics of said inbred tomato parent plant, wherein said selection preferably comprises the isolation of genomic DNA and testing said DNA for the presence of at least one molecular marker for the gene as defined above;

(e) repeating steps (c) and (d) two or more times in succession to produce selected third or higher backcross progeny plants;

(f) optionally selfing selected backcross progeny in order to identify homozygous plants;

(g) crossing at least one of said backcross progeny and/or selfed plants with another inbred tomato parent plant to generate a hybrid tomato variety with the desired trait and all of the morphological and physiological characteristics of hybrid tomato variety when grown in the same environmental conditions.

As indicated, the last backcross generation may be selfed in order to provide for homozygous pure breeding (inbred) progeny exhibiting tolerance to continuous light. Thus, the result of recurrent selection, backcrossing and selfing is the generation of lines that are genetically homozygous for the genes associated with tolerance to continuous light as well as other genes associated with traits of commercial interest.

It should be noted that heterozygous plants having the gene for tolerance to continuous light may also be of interest as intermediate products, and such plants are therefore also an aspect of the present invention.

Tomato Plants and Seeds

The goal of plant breeding is to combine various desirable traits in a single variety or hybrid. For commercial crops, these traits may include resistance to diseases and insects, tolerance to heat and drought, reducing the time to crop maturity, greater yield, and better agronomic quality. Uniformity of plant characteristics such as germination, growth rate, maturity, and plant height may also be of importance.

Commercial crops are bred through techniques that take advantage of the plant's method of pollination. A plant is self-pollinated if pollen from one flower is transferred to the same or another flower of the same plant. A plant is sibling mated when individuals within the same family or line are used for pollination. A plant is cross-pollinated if the pollen comes from a flower on a different plant from a different family or line.

Plants that have been self-pollinated and selected for type for many generations become homozygous at almost all gene loci and produce a uniform population of true-bred progeny. A cross between two different homozygous lines produces a uniform population of hybrid plants that may be heterozygous for many gene loci. A cross of two plants each heterozygous at a number of gene loci will produce a population of heterogeneous plants that differ genetically and will not be uniform.

The development of a hybrid tomato variety in a tomato plant breeding program involves three steps: (1) the selection of plants from various germplasm pools for initial breeding crosses; (2) the selfing of the selected plants from the breeding crosses for several generations to produce a series of inbred lines, which, individually breed true and are highly uniform; and (3) crossing a selected inbred line with an unrelated inbred line to produce the hybrid progeny (F1). After a sufficient amount of inbreeding successive filial generations will merely serve to increase seed of the developed inbred. Preferably, an inbred line should comprise homozygous alleles at about 80% or more of its loci.

An important consequence of the homozygosity and homogeneity of the inbred lines is that the hybrid created by crossing a defined pair of inbreds will always be the same. Once the inbreds that create a superior hybrid have been identified, a continual supply of the hybrid seed can be produced using these inbred parents and the hybrid tomato plants can then be generated from this hybrid seed supply.

Using the methods as described above, the skilled person will be able to produce the required inbred lines and from those produce the commercial (F1) hybrid seeds by crossing said inbred lines.

The present invention will now be explained in more detail by way of the following non-limiting Examples.

EXAMPLES

Example 1 Tolerant Donors

Different accessions of wild species (lines) were sown in a growth chamber with 16 hours of light per day. Two weeks after sowing, the seedlings of each line were randomly divided in two groups, one group continued to grow in 16 hours of light per day while the other was grown in another growth chamber under continuous light. After 3-4 weeks symptoms of the sensitive lines were clearly visible, while absent in the tolerant lines (FIG. 1). The typical symptoms of a sensitive line are leaf chlorosis, necrosis and poor biomass production which was absent in the tolerant genotypes shown in FIG. 1.

Example 2 Quantifying the Symptoms and Optimise Protocol

Figure 2:
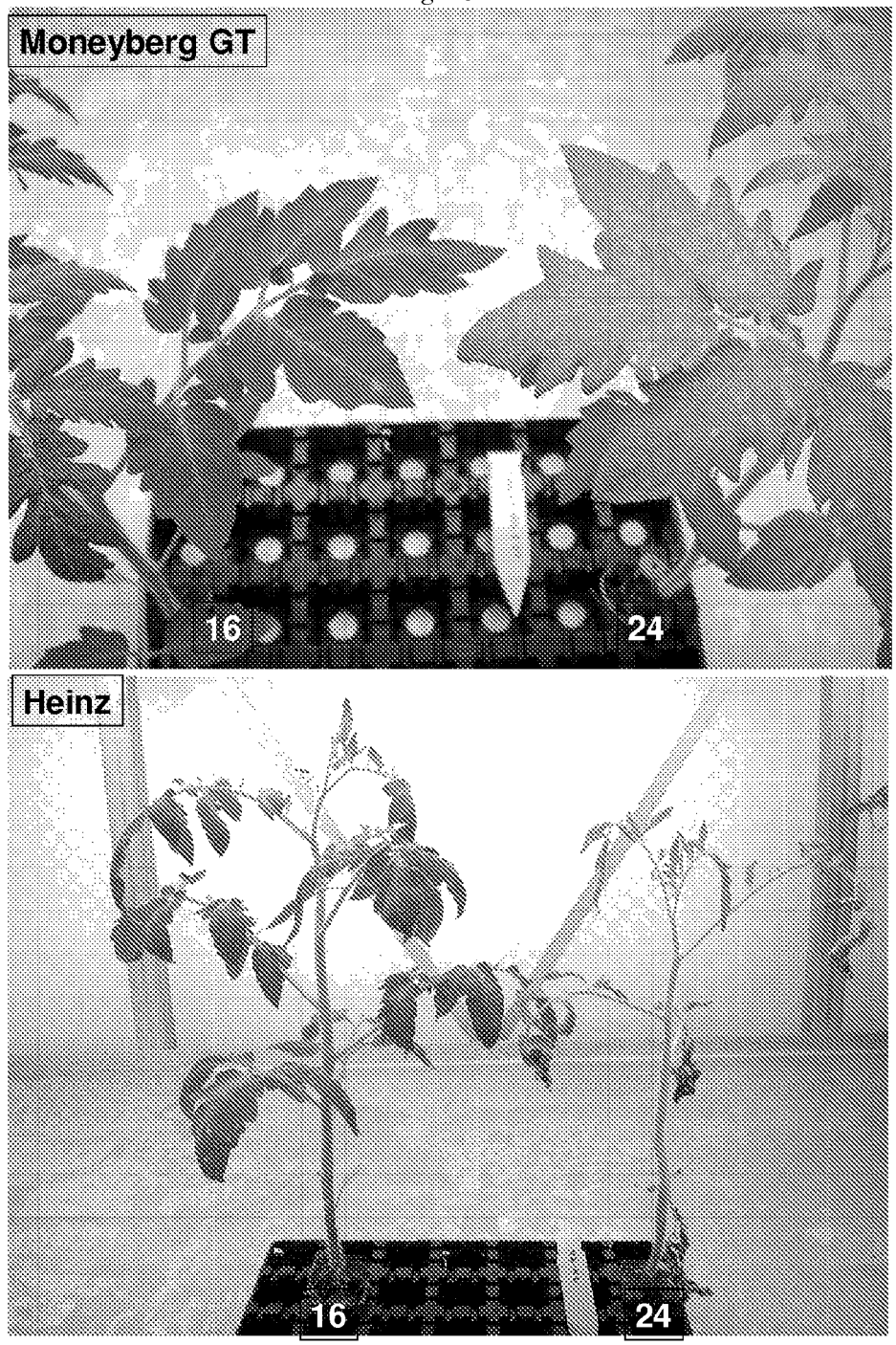
FIG. 2: typical symptoms caused by exposure to continuous light in non-tolerant lines. The first visible symptoms of non tolerant lines are light green leaves with inter-vine chlorosis, followed by severe chlorosis. In severe non tolerant plants chlorosis is followed by necrosis, decreased leaf development decreased stem development and even plant mortally.

In the same experiment as experiment 1 the sensitive lines showed at first light green leaves with inter-vine chlorosis, followed by severe chlorosis (FIG. 2). In severe non tolerant plants chlorosis is followed by necrosis, decreased leaf development decreased stem development and even plant mortally.

Figure 3:
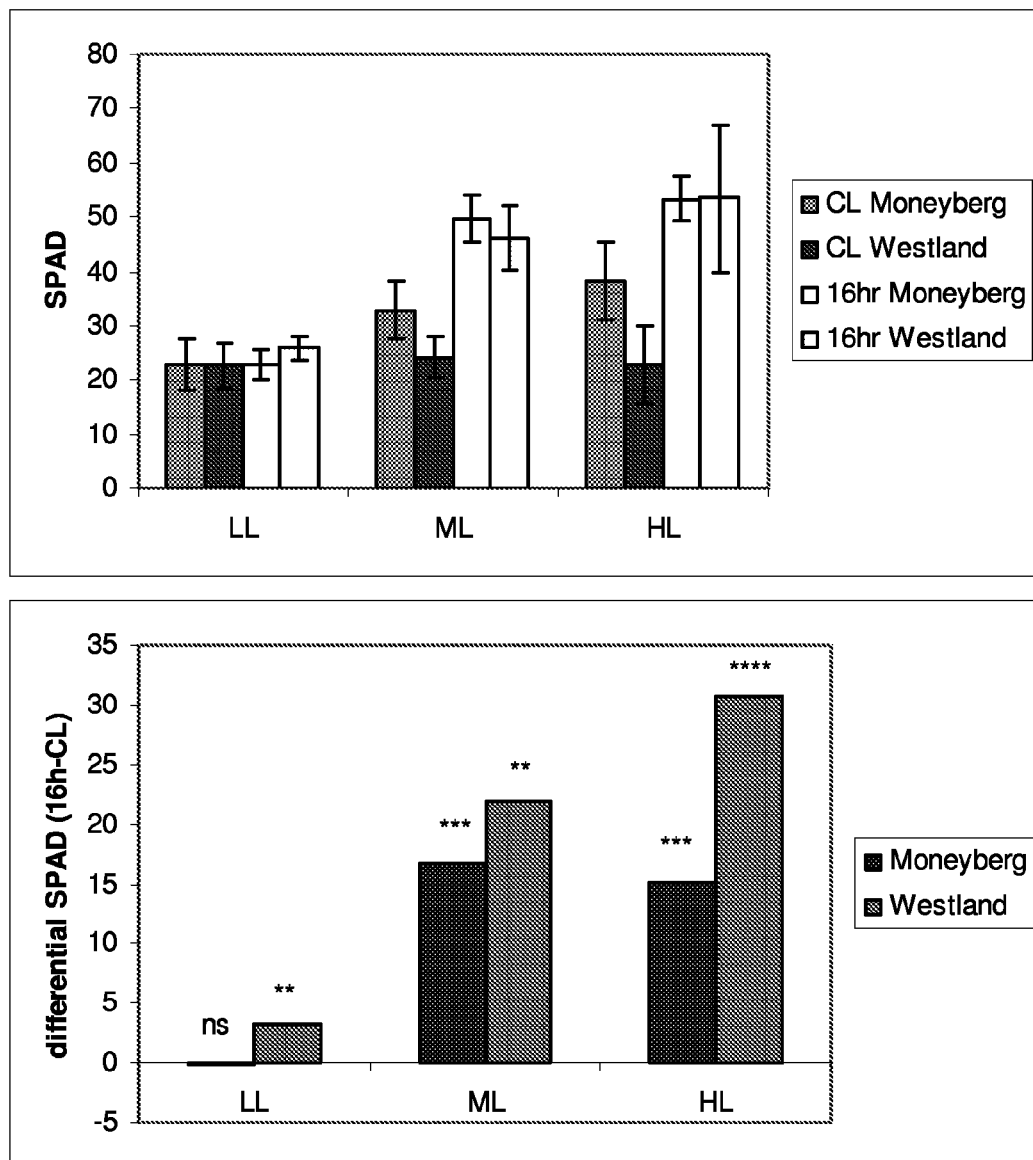
FIG. 3: Degreening and chlorosis. Quantification of a part of the visible symptoms (degreening and chlorosis) by measuring the chlorophyll concentration by a SPAD® meter was performed with plants grown at 131 µmol m$^{-2}$ s$^{-1}$ (ML) or 230 µmol m$^{-2}$ s$^{-1}$ (HL). The resolution to detect differences between continuous and non-continuous light was very difficult or impossible at very low light intensities (16 mol m$^{-2}$ S$^{-1}$=LL). The visible symptoms developed earlier in time at 230 mol m$^{-2}$ s$^{-1}$ compared to 131 µmol m$^2$ s$^{-1}$. Left: averages with standard deviations, number of replicates is 20 to 40. Right: Data extracted from the left graph, plotted is the differences between 16 and 24 hours of light per light intensity. Significance level is shown by ns=not significant, *=p<0.05, =p<0.01, *=p<0.001 and ****=p<0.00001.
Figure 4:
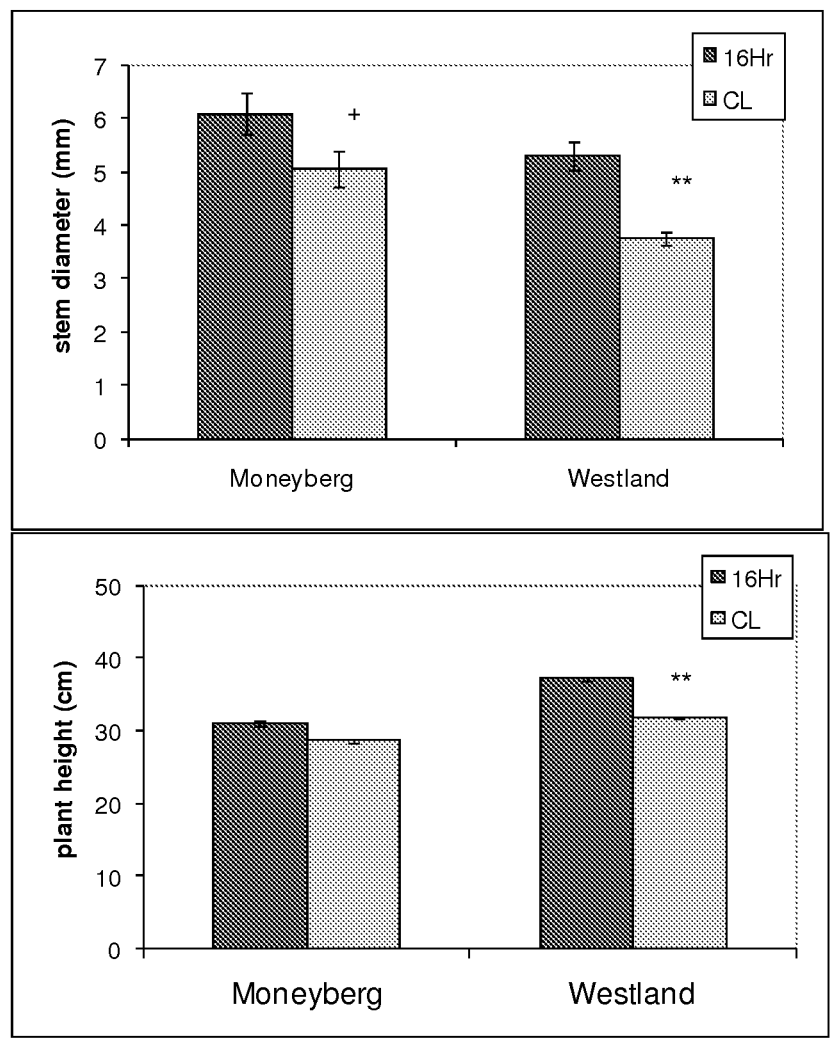
FIG. 4: Stem diameter and plant height is decreased in non tolerant lines. Therefore stem diameter and plant height are also parameters to be able to quantify continuous light symptoms. Averages with standard errors, number of replicates is 4 to 8. Significance level is shown by +=p<0.1, *=p<0.05, =p<0.01, *=p<0.001.
Figure 7:
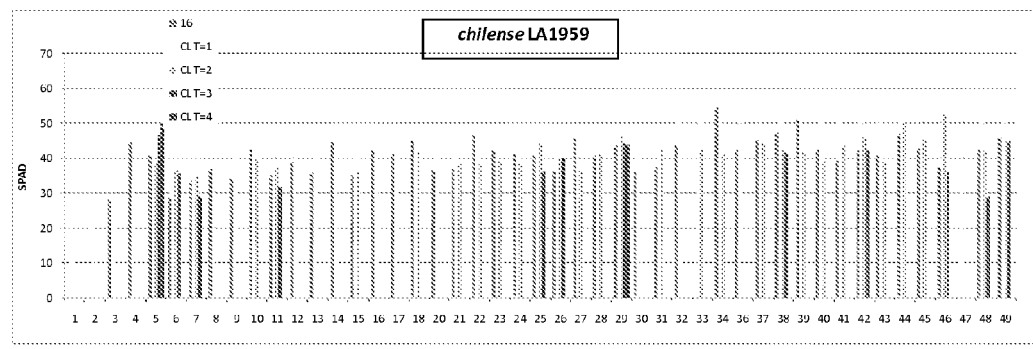
FIG. 7: Chlorophyll concentration of IL lines from a *chilense* LA1959*Moneyberg GT population where 15 days old seedlings exposed for 35 (CLT1), 42 (CLT2), 49 (CLT3) and 60 (CLT4) days to continuous light. Temperature 21° C./20° C. for 16/8 hours and, with an RH of 70% and a light intensity of 110-120 µmol m$^{-2}$ s$^{-1}$ (PAR) from fluorescent tubes during the first 15 days followed by illumination under High pressure sodium lamp (SON-T) for 24 Hr. Averages with standard errors, number of replicates was 3 to 6 plants per line.

Besides the clear visible symptoms of the sensitive line in continuous light the symptoms can also be quantified by measuring the chlorophyll concentration. The chlorophyll concentration can be measured chemically but also spectroscopically with a SPAD meter (SPAD-502, Konica Minolta, Nieuwegein, Netherlands). Two sensitive lines (Moneyberg and Westland) were grown as described in experiment 1, except that also the light intensity was a experimental factor from two weeks after sowing. The plants were placed in low light intensities (16 $\mu$mol m$^{-2}$ s$^{-1}$=LL) moderate light 131 $\mu$mol m$^{-2}$ s$^{-1}$ (ML) or relative high light 230 $\mu$mol m$^{-2}$ s$^{-1}$ (HL). Quantification of a part of the visible symptoms (degreening and chlorosis) by measuring the chlorophyll concentration by a SPAD meter was performed with plants grown at 131 $\mu$mol m$^{-2}$ s$^{-1}$ (ML) or 230 $\mu$mol m$^{-2}$ s$^{-1}$ (HL). The resolution to detect differences between continuous and non-continuous light was very difficult or impossible at very low light intensities (16 $\mu$mol m$^{-2}$ s$^{-1}$=LL) (FIG. 3). The visible symptoms developed earlier in time at 230 $\mu$mol m$^{-2}$ s$^{-1}$ compared to 131 $\mu$mol m$^{-2}$ s$^{-1}$. In the same experiment also the stem diameter and plant height was decreased in these non tolerant lines (FIG. 4). Not only a higher light intensity resulted in a faster induction of symptoms also a prolonged exposure to continuous light did increase the symptoms in sensitive lines (FIG. 7, 9). In several lines the symptoms did appear later than after 3 to 4 weeks in continuous light.

In conclusion the continuous light symptoms can be quantified by measuring the chlorophyll concentration in the leaves but also by measuring the stem diameter or height. The quantitative tolerance trait can be measured qualitative by increasing the light intensity or increasing the duration of the continuous light. This makes it easier to map the tolerance.

Example 3 Tolerant Lines from *Neorickii* (LA2133)

Figure 5:
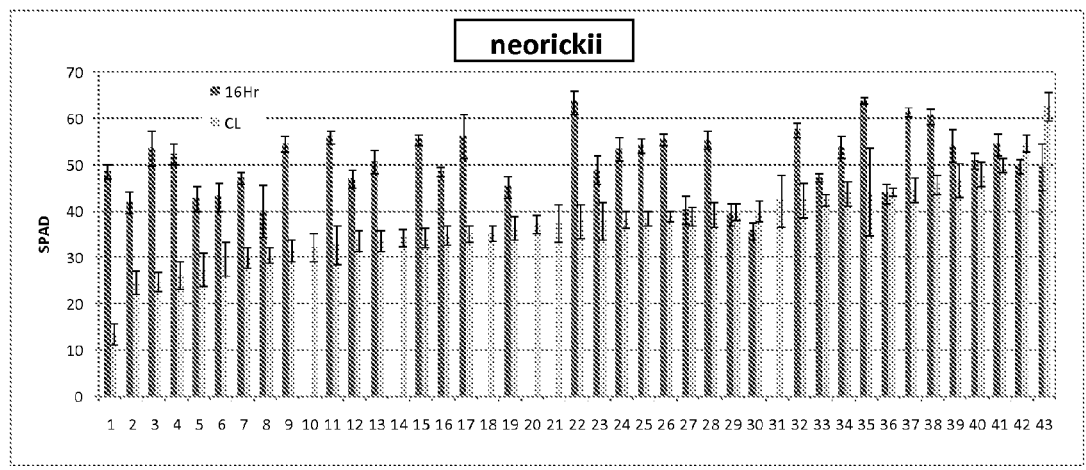
FIG. 5: Chlorophyll concentration of IL lines from a *neorickii**a sensitive *esculentum* (e.g. Moneyberg) population where 9 days old seedlings exposed for 33 days to continuous light. Temperature 21° C. for 24 hours and, with an RH of 70% and a light intensity of 110-120 µmol m$^{-2}$ s$^{-1}$ (PAR) from fluorescent tubes. Averages with standard errors, number of replicates was 3 to 6 plants per line.
Figure 6:
FIG. 6: One highly tolerant line (42) from a *neorickii**a sensitive *esculentum* (left). Tolerant lines are exposed to continuous light for 90 days. The first 33 days under fluorescent tubes, followed by illumination under High pressure sodium lamp (SON-T). The leaves stay green, leaf and stem development is normal compared to non tolerant lines.

A segregating population between *neorickii* and a sensitive *esculentum* (e.g. Moneyberg) showed large natural variation in the chlorophyll concentration as measured with a SPAD meter (FIG. 5). In FIG. 6 two tolerant lines (42 and 43) are shown, which have been in continuous light for 90 days.

Example 4 Tolerant Lines from *Chilense* (LA1959)

Figure 8:
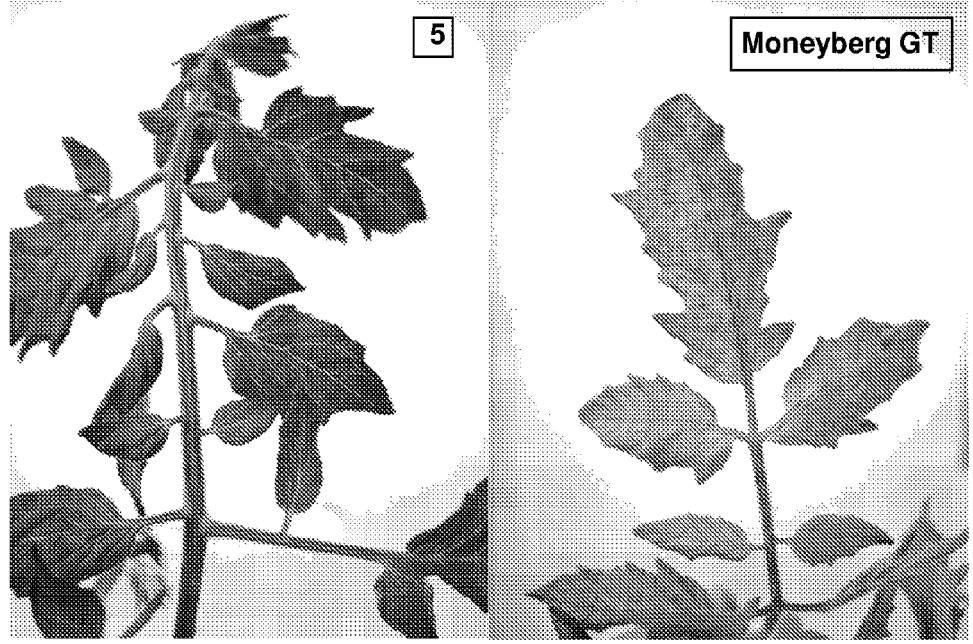
FIG. 8: One highly tolerant line (5) from a *chilense* LA1959*a sensitive Moneyberg GT. Tolerant lines are exposed to continuous light for 90 days. The leaves stay green, leaf and stem development is normal compared to non tolerant lines.

A segregating population between *chilense* and a sensitive *esculentum* (e.g. Moneyberg GT) showed large natural variation in the chlorophyll concentration as measured with a SPAD meter (FIG. 7). In FIG. 8 one tolerant line (5) is shown, which have been in continuous light for 60 days.

Example 5 Tolerant Lines from *Pennellii* (LA716*M82)

Figure 9:
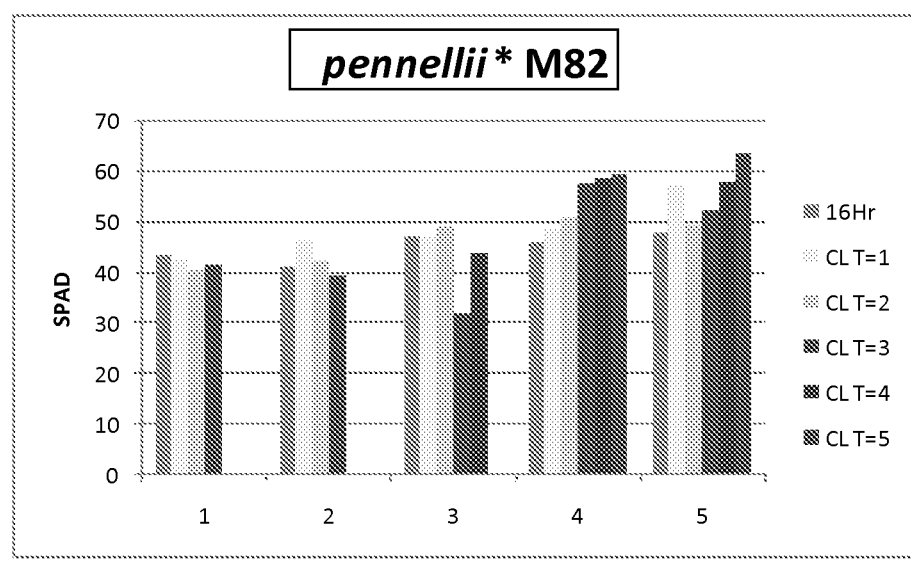
FIG. 9: Chlorophyll concentration of IL lines from a *pennellii**M82 population with an introgression on chromosome 7. Chlorophyll concentration of IL lines from a *pennellii**M82 population where 14 days old seedlings were exposed for 21 (CLT1), 28 (CLT2), 35 (CLT3), 42 (CLT4) and 53 (CLT5) days to continuous light. Temperature 21° C./20° C. for 16/8 hours and, with an RH of 70% and a light intensity of 110-120 µmol m$^{-2}$ s$^{-1}$ (PAR) from fluorescent tubes the first 14 days after that under SON-T for 24 Hr. Averages with standard errors, number of replicates was 4 to 6 plants per line. Two tolerant lines were found (4 and 5), which have been in continuous light for 53 days.

A segregating population between *pennellii* and M82 was used and only lines with a chromosomal introgression from *pennellii* into M82 on chromosome 7 were used. Natural variation in the chlorophyll concentration as measured with a SPAD meter was identified (FIG. 9). Two tolerant lines (4 and 5) are found, which have been in continuous light for 53 days.

Example 6 Continuous Light Tolerance Loci on Chromosome 7

Figure 10:
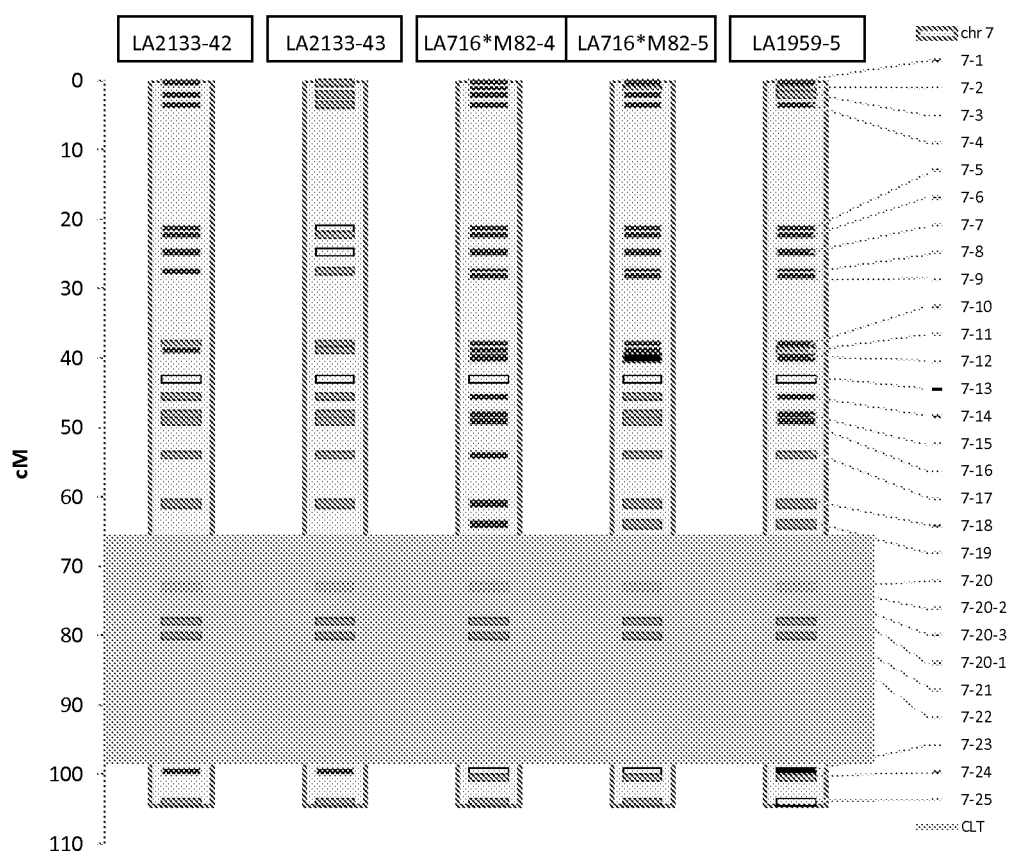
FIG. 10: Genotypic information of the different mapping populations, based on Illumina SNP markers. Combining the phenotypic and genotypic data from the three populations, the continuous light tolerant loci is located on chromosome 7 between marker "7-19" and "7-23" that is between 64 and 99.6 cM based on the EXPEN2000 linkage map. Wild donor alleles are shown in light grey, recurrent parent alleles in dark grey, different alleles in black and no call in white. Some SNPs are non polymorphic in some wild donor x recurrent parent combinations, in such cases a gap is present. SNPs markers were genotyped using GoldenGate assays (Illumina).

The genetic information from the 6 different mapping population it is clear that the loci for continuous light tolerance is located on chromosome 7 (FIG. 10). Moreover, by combining the information of all populations it is shown that the loci is located between marker "7-19" and "7-23" that is between 64 and 99.6 cM. The sequence in formation from these 2 markers and 23 additional ones which are also linked to the trait are shown in FIG. 11.

Example 7 Detection of Marker 7-20-1

To detect the G/T polymorphism of marker 7-20-1, a TaqMan assay (Applied biosystems) was used. The assay employs two universal primers (a forward primer having the sequence 5'-GAATTGGCTTTATGTATTTGGAATCCT-TGT-3' (SEQ ID NO:29) and a reverse primer having the sequence 5'-CCCATCTAGGACCCCTGCAT-3' (SEQ ID NO:30)) to amplify a fragment of 76 bp and two allele specific probes. A probe having the sequence (5'-TTTACT-GTATTTTTCTTTTTCTCCA-3' (SEQ ID NO:31) (*S. lycopersicum* (recurrent)) specifically detects the *S. lycopersicum* allele (The "T" SNP) and carries a VIC reporter fluorescent dye. A second probe having the sequence 5'-TT-TACTGTATTTTTCTTTTGCTCCA-3' (SEQ ID NO:32) (*S. neorickii* LA2133 (donor)) detects the allele from *S.* neorickii LA 2133 (the "G" SNP) and carries a 6-carboxyfluorescein (FAM) dye. Amplification of one of the two or both alleles can be monitored using a real-time PCR (polymerase chain reaction) machine which measures the level of fluorescence of the respective dyes. DNA samples that only contain the S. lycopersicum allele will emit a VIC signal while samples that contain the S. neorickii allele will emit the FAM signal. Samples that contain both alleles will emit both signals.

The assay was validated on DNA samples of elite sensitive lines and CLT donor LA2133. All other CLT donor lines had the same allele. The assay was also validated on the 46 introgression lines that were derived from LA2133 and "Moneyberg". The marker showed presence of the "G" allele in LA2133 and introgression lines LA2133-42 and LA2133-43. All other tested lines showed presence of the "T" allele Example 8 Fine Mapping of Continuous Light Tolerance Trait To identify closer linked markers for the continuous light tolerance trait fine mapping in the LA2133 background was performed. Lines LA2133-42 and LA2133-43 were backcrossed with their sensitive recurrent parent. Both F1s were selfed and the F2 offspring was genotyped for recombination with flanking markers 7-10 and 7-25. In total 770 and 616 plants were genotyped for LA2133-42 and LA2133-43 respectively. In total 40 lines were selected to generate a F3 from which 15 lines were controls. 22 Seeds per F3 family were sown in 2 blocks of 11 seeds. A total of 18 F3 families were screened. From several F3 families the germination was too low to yield sufficient (>=13) plants for phenotyping the continuous light tolerance trait.

Mapping indicated that the position of the continuous light locus is located between markers 7-17 and 7-20 (FIG. 12). Marker 7-19 was monomorphic in the tested LA2133 populations.

Figure 13:
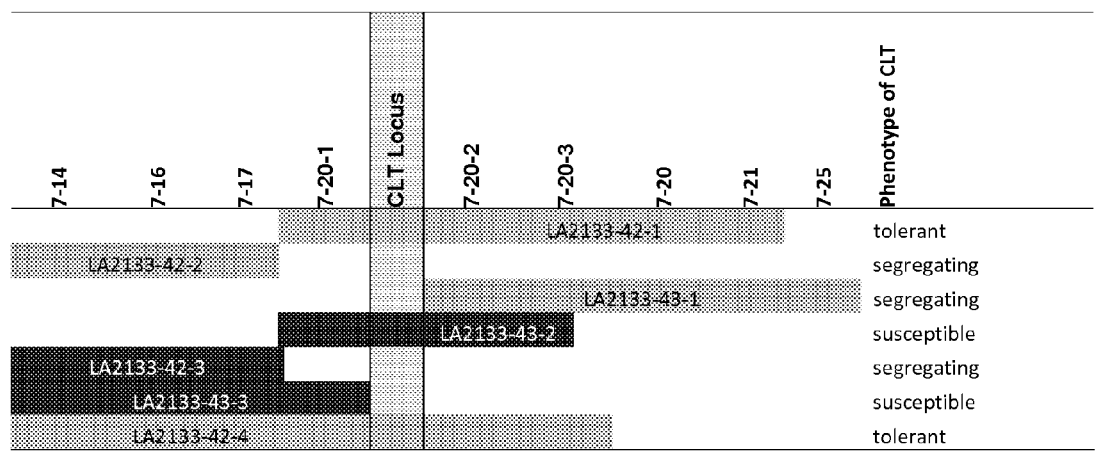
FIG. 13. The CLT locus is positioned between markers 7-20-1 and 7-20-2. Presented genotypic data (the genotypes include "homozygous for donor" or "recurrent parent" and "heterozygous") is generated from F2 plants, while phenotypic scoring (the phenotypes include "tolerant to continuous light", "susceptible for continuous light" and "segregating") is performed on F3 plants. Dark grey blocks indicate genomic segments originating from the sensitive parent. Light grey blocks indicate segments that are originating from the tolerant parent. White blocks indicate heterozygous segments. Markers are ordered according to map LA2133-42.

New markers were developed between marker 7-17 and 7-20 and are named 7-20-1, 7-20-2 and 7-20-3 (FIG. 11). Using the new markers on the same phenotyped populations revealed that the position of the continuous light locus is located between markers 7-20-1 and 7-20-2 (FIG. 13).

The three newly developed markers were tested on DNA samples of complete F2 families to generate a new linkage map of the CLT locus (continuous light trait locus). The linkage map EXPEN2000 and the generated linkage map of LA2133-42 showed some differences on the location of the new SNP markers (See Table 1 and FIG. 10). The LA2133-42 map shows the preferred order.

TABLE 1

| Marker | LA2133-42 | EXPEN2000 |
|--------|-----------|-----------|
| 7-20-1 | 43.68 cM  | 75 cM     |
| 7-20-2 | 44.35 cM  | 72 cM     |
| 7-20-3 | 44.46 cM  | 73 cM     |
| 7-20   | 46.18 cM  | 73 cM     |
| 7-21   | 46.74 cM  | 78 cM     |

Based on the mapping in LA2133-42 highly preferred markers linked to the continuous light trait, span a locus of about 0.67 cM.

Example 9 Genes at the CLT Locus

A BLAST® search to the tomato genome (version 1.0; released December 2009) revealed that the markers of the CLT locus arc preferably located on scaffold 07408 (SL1.00sc07408 position:1975288 through 2058583). The region between the markers 7-20-1 and 7-20-2 spans 83296 bp and contains 15 genes (ITAG1 annotation). Table 2 lists all genes at this locus and the available TaqMan markers. Table 3 lists all sequences of these genes. One of the genes (SL1.00sc07408_301.1.1 is the LHCB3 Light-Harvesting Chlorophyll B-Binding Protein 3 structural molecule". This gene encodes a protein that—in one preferred embodiment of the invention—plays a crucial role in the continuous light trait. Plants of the present invention therefore in a preferred embodiment of the invention comprise this gene. The other genes in this locus can also be used in aspects of this invention.

TABLE 2

Genes in the CLT locus

| Name | Type | Description | Size | Start | Stop | Strand |
|------|------|-------------|------|-------|------|--------|
| 7-18 | | | 100 | 2878606 | 2878726 | forward |
| SL1.00sc07408_313.1.1 | transcript_ITAG | late embryogenesis abundant protein-related/ LEA protein-related (AHRD V1 ***NG AT5G54370.1); contains Interpro domain(s) IPR009646 Root cap | 573 | 2093160 | 2093732 | forward |
| SL1.00sc07408_312.1.1 | transcript_ITAG | LDL2 LSD1-LIKE2 amine oxidase/electron carrier/ oxidoreductase (AHRD V1 **-NG AT3G13682.1); contains Interpro domain(s) IPR002937 Amine oxidase | 6585 | 2093055 | 2086471 | reverse |
| SL1.00sc07408_311.1.1 | transcript_ITAG | Unknown Protein (AHRD V1); contains Interpro domain(s) IPR009651 Aluminium resistance | 7561 | 2082437 | 2074877 | reverse |
| SL1.00sc07408_310.1.1 | transcript_ITAG | Transmembrane protein 184C (AHRD V1 ***NG Q5RET6); contains Interpro domain(s) IPR005178 Protein of unknown function DUF300 | 3624 | 2073719 | 2070096 | reverse |

TABLE 2-continued

Genes in the CLT locus

| Name | Type | Description | Size | Start | Stop | Strand |
|---|---|---|---|---|---|---|
| SL1.00sc07408_309.1.1 | transcript_ITAG | Unknown Protein (AHRD V1) | 4836 | 2069193 | 2064358 | reverse |
| SL1.00sc07408_308.1.1 | transcript_ITAG | Unknown Protein (AHRD V1) | 2919 | 2061327 | 2064245 | forward |
| SL1.00sc07408_307.1.1 | transcript_ITAG | AGD5 ARF-GAP domain 5 ARF GTPase activator/ DNA binding/zinc ion binding (AHRD V1 *-*G AT5G54310.1); contains Interpro domain(s) IPR001164 Arf GTPase activating protein | 6889 | 2060607 | 2053719 | reverse |
| 7-20-1 | | Flanking marker CLT | 100 | 2057927 | 2058583 | reverse |
| SL1.00sc07408_306.1.1 | transcript_ITAG | Unknown Protein (AHRD V1); contains Interpro domain(s) IPR008480 Protein of unknown function DUF761, plant | 1950 | 2050327 | 2048378 | reverse |
| SL1.00sc07408_305.1.1 | transcript_ITAG | cytochrome c biogenesis protein family (AHRD V1 *-*NG AT5G54290.1); contains Interpro domain(s) IPR003834 Cytochrome c assembly protein, transmembrane region | 6176 | 2040973 | 2047148 | forward |
| SL1.00sc07408_304.1.1 | transcript_ITAG | Unknown Protein (AHRD V1) | 2874 | 2034960 | 2037833 | forward |
| SL1.00sc07408_303.1.1 | transcript_ITAG | Myosin-Va (AHRD V1 ***NG Q02440); contains Interpro domain(s) IPR001609 Myosin head, motor region | 8186 | 2030449 | 2022264 | reverse |
| SL1.00sc07408_302.1.1 | transcript_ITAG | ATM2 *ARABIDOPSIS THALIANA* MYOSIN 2 motor (AHRD V1 ***NG AT5G54280.2); contains Interpro domain(s) IPR000048 IQ calmodulin-binding region | 1832 | 2022005 | 2020174 | reverse |
| SL1.00sc07408_301.1.1 | transcript_ITAG | LHCB3 LIGHT-HARVESTING CHLOROPHYLL B-BINDING PROTEIN 3 structural molecule (AHRD V1 ***G AT5G54270.1); contains Interpro domain(s) IPR001344 Chlorophyll A-B binding protein | 1633 | 2018017 | 2019649 | forward |
| SL1.00sc07408_300.1.1 | transcript_ITAG | Dynein light chain 1 cytoplasmic-like protein (AHRD V1 *-*NG B0X7V2_CULQU); contains Interpro domain(s) IPR001372 Dynein light chain, type 1 and 2 | 1195 | 2015289 | 2016483 | forward |
| SL1.00sc07408_299.1.1 | transcript_ITAG | Unknown Protein (AHRD V1); contains Interpro domain(s) IPR010634 Protein of unknown function DUF1223 | 2477 | 2013512 | 2011036 | reverse |
| SL1.00sc07408_298.1.1 | transcript_ITAG | ATMAMI *ARABIDOPSIS THALIANA* MEMBRANE-ASSOCIATED MANNITOL-INDUCED structural molecule (AHRD V1 *-*G AT5G54110.1); contains Interpro domain(s) IPR008962 PapD-like | 3392 | 2006924 | 2010315 | forward |
| SL1.00sc07408_297.1.1 | transcript_ITAG | Wound induced protein (AHRD V1 ***NG B6SKC8_MAIZE) | 461 | 2001724 | 2002184 | forward |
| SL1.00sc07408_296.1.1 | transcript_ITAG | Ubiquitin carboxyl-terminal hydrolase (AHRD V1 ***G A7P1D3_VITVI); contains Interpro domain(s) | 9792 | 1988575 | 1998366 | forward |

TABLE 2-continued

Genes in the CLT locus

| Name | Type | Description | Size | Start | Stop | Strand |
|---|---|---|---|---|---|---|
| SL1.00sc07408_295.1.1 | transcript_ITAG | IPR016652 Ubiquitinyl hydrolase Unknown Protein (AHRD V1) | 1254 | 1987084 | 1985831 | reverse |
| SL1.00sc07408_294.1.1 | transcript_ITAG | Unknown Protein (AHRD V1) | 1308 | 1979129 | 1977822 | reverse |
| SL1.00sc07408_293.1.1 | transcript_ITAG | universal stress protein USP family protein (AHRD V1 *-*NG AT4G27320.1); contains Interpro domain(s) IPR006016 UspA | 3278 | 1975876 | 1972599 | reverse |
| 7-20-2 | | Flanking marker CLT | 100 | 1975288 | 1975845 | forward |
| SL1.00sc07408_292.1.1 | transcript_ITAG | PBP1 PINOID-BINDING PROTEIN 1 calcium ion binding/protein binding (AHRD V1 **-G AT5G54490.1); contains Interpro domain(s) IPR011992 EF-Hand type | 668 | 1969824 | 1970491 | forward |
| SL1.00sc07408_291.1.1 | transcript_ITAG | Serine/threonine kinase-like protein (AHRD V1 ***G Q0WPA4_ARATH); contains Interpro domain(s) IPR002290 Serine/threonine protein kinase | 3701 | 1962690 | 1966390 | forward |
| SL1.00sc07408_290.1.1 | transcript_ITAG | ARK3 A. THALIANA RECEPTOR KINASE inase/ transmembrane receptor protein serine/threonine kinase (AHRD V1 *-*G AT4G21380.1); contains Interpro domain(s) IPR002290 Serine/threonine protein kinase | 3742 | 1957638 | 1961379 | forward |
| SL1.00sc07408_289.1.1 | transcript_ITAG | protein kinase family protein (AHRD V1 *-*NG AT4G11470.1); contains Interpro domain(s) IPR002290 Serine/threonine protein kinase | 7051 | 1953626 | 1946576 | reverse |
| SL1.00sc07408_288.1.1 | transcript_ITAG | ferredoxin-related (AHRD V1 ***NG AT1G02180.1) | 2040 | 1945028 | 1942989 | reverse |
| 7-20-3 | | | 100 | 1943149 | 1943396 | reverse |
| SL1.00sc07408_287.1.1 | transcript_ITAG | protein kinase family protein (AHRD V1 ***G AT4G23150.1); contains Interpro domain(s) IPR002290 Serine/threonine protein kinase | 1459 | 1940509 | 1941967 | forward |
| 7-20 | | | 100 | 1686186 | 1686306 | reverse |
| 7-21 | | | 100 | 1480300 | 1480420 | reverse |
| 7-25 | | | 100 | 464589 | 464709 | reverse |

TABLE 3

SL1.00sc07408_313.1.1 (SEQ ID NO: 33)

```
TGCATGCTT TCTCAGTGGA GGCTACCAAG GCAGAGTCTT GGGACGACGA AGTTGATCAT CTGAAATTCT

ATTATAATGG AAAAGAGTTA GGCTTACCAG AAGGATATCC ATCCATATGG GAATCTTCTG AAAGCGGCAT

CAAGGTAGAA AGAACTGCAA ACAAGAACGG TGCTTTTATC ACACTACCAG AAGTAGCAGA AATTTCAGTA

AATGTAGTAC CTATTACCAA GGAAGATGAC AGGATCCACA ACTATCAGTT ACCTTCTGAT GACTGCTTCG

CTCACCTGGA CGTGCAGTTC AGATTCTATG GCCTCTCAAC GAAGGTTGAA GGCGTTCTTG GCCGGACGTA

CCAGCCAGAC TTCAAAAATC CAGCAAAACC AGGTGTTGCA GTGCCTGTAG TGGGAGGTGA AAAGATGTAC

AGAACTTCAA CCCTTTTGTC TTCCAAATGT AACTCCTGTA TCTTCTCTCC AGCTGGAGTT TCTGAAGAAT

CAGACCCCCT AGTCATGGAT TATGGGACTT TAGATTGTAC TGGAGGATCA AGCGGTGGCC ACGGAATAAT
```

TABLE 3-continued

TTGCAGAAAA TGA

SL1.00sc07408_312.1.1 (SEQ ID NO: 34)

ATGGAAATCC CAAATTCAGG GGGTTCAGTC TCAAGGAGAC CTGTGAGAAG GAGGTTCGCT TCTAGGAATT

ATGATGAGAC TGTGATGGAT AAAATCATAG ATGAGCAGTT GGGTAGTCCG GTGGGGAAGA AGATTAGAAC

GAAGAAAGAT TTGGAGAAAG AAACTGAAAA AGAGGCCTTG ATTGCTCTTT CTTTGGGCTT CCCAATTGAT

GACCTTCTTG AAGAAGAAAA AAAGGCTGGA GTTGTAAGTG AATTGGATGG GAAAGAGCAA AACGATTACA

TCGTTGTGAG AAATCATATT CTCGCAAAAT GGAGGGAGAA TGTGCATATT TGGCTGAACA AAGGAAGGAT

AAGGGAAATT ATAAGTGTCG AGTATGAACA TTTGGTAGCC ATAGCATATG ATTTTCTTTT AAGTAACGGG

TATATAAATT TCGGGGTTTC ATCATCATTT GAATCTAATC TTCCTGAGGA ACCTAGAGAA GGGTCTGTAA

TTATCATTGG TGCTGGACTC GCTGGTTTGG CTGCAGCAAG GCAACTGATG GCTTTTGGAT TTAAGGTAAC

TGTCCTTGAA GGTAGGAACC GACCTGGAGG GAGAGTTTAT TCTGAGAAAA TGGGATGGAA GGGAAAGTTT

GCTGCTGTGG ATCTTGGTGG CAGCGTTATA ACTGGTATCC ATGCGAATCC TTTGGGAGTT TTGGCTAGAC

AACTTTCCAT TCCGCTTCAC AGTGTTAGAG ATAAGTGTCC TTTATACAAG CCTGATGGTG CTCCTGTTGA

TTCAGTAGTT GATTCCACAG TTGAACTCAT TTTCAATAAG CTACTAGACA AAGTTGCTGA ACTACGAAAA

ATCGTAAGTG GATTGGCTAC TGATGTCTCG TTAGGCTCCG TTTTGGAGAC ACTTAGACGA TTATATTGTG

TGGCTAAAAC TAAAGAGGAG AAGCAACTTC TGCATTGGCA TTTTGCAAAC TTGGAATATG CAAATGCTGG

ATGCCTCTCG GAACTCTCTG CTGCCTACTG GGATCAGGAC GATCCTTATG AAATGGATGG TGATCATTGT

TTTCTTGTTG GTGGAAATCG AGCTATGATC AGGGCATTGT GTAAAGGAGT TCCTATATTC TATGGAAAGA

CTGTTCAGAC AATTAAGTAT GGAAATGAAG ACTAAAAAGA AGATCAATTA GATTTGAACC AGAGTTACCT

GAGAAGAAGC TTGAAGCTAT TGATAGGCTA GGATTTGGGT TGCTGAATAA AGTTGCCATG GTATTTCCTC

ATATTTTTTG GGGCGAAGAC TTGGATACCT TCGGTTGCCT CAACCATCAT AGCCACAGAC GAGGAGAGTA

CTTCTTATTT TACAGTTACC ATACTGTTTC TGGGGGTCCA GTACTTATTG CACTTGTTGC TGGTGACGCT

GCTCAACTTT TCGAAAGCAC AGATCCGTCC ACTTTAATTA ATCGAGTGAT TAACATTCTC AAAGGCATTT

ATGAGCAAAA GGGAATAAGC GTGCCTGATC CTATACAATC CATATGCACA AAATGGGGAA GTGATCCCTT

TTCGTTTGGC TCATATTCAC ATGTTCGTGT TCAGTCATCT GGCAGTGATT ATGACATACT TGCAGAAAAT

CTCGGAGGTC GGTTGTTTTT TGCTGGAGAG GCTACGATTC GACAACATCC AGCCACCATG CATGGAGCCT

ATTTGAGTGG CTTAAGAGAA GCTTCTCACA TTTCCCAATC CATGAAAGCG AGGCAAAACA ATCCAAGGAG

AACTGTATCA AGAATGTTC GACCAAGCAA TGATACATTG AAGAGTTGT TTGAAAAGCC AGATCTAGCA

TTCGGGAAGT TGTTATTTGT ATTTGATCCC CTCACTTGTG ATTCTAATTC TTTAGGACTG ATGAGAGTTA

CTTTTGGAAA ATCCAACGAC GAGCTTAATT CAGAAGAGGT AGACAATATG CCTCAACATT TATTAAATCC

ATCACTGCAG CTTTATACAG TTGTGTCTCG TGAGCAAGCA CATGAGCTGC AGTTGGTGAA GGAGGGAAAC

AATTGCAAAT TGTTAGATTT GCTTGAAGGT CTTGGGTTAA AGTTAGTGGG AGCGAATGGA CTAGGAGTTC

AAGGCCATAC TTTGGCTGCT AAAATTGTTA AAGGTAGAAG GAGTCGAAGC TATACTGCCA AGCAGAAGGC

AGGCGAAAGT AGCAGTCAGT ATATATTGTG CATCTGGCAG CAGAGTGTGA AAAAGGATC GATGAACGCG

CGTTTTGCAT CTGGTTTGGG AGTTTCAAGC CTTCCTACTC TGTGCTGTTG TTTATGTTGT GGATATTTTT

CTATATGCTT GTGCTTTGTA CTCCTAGATA GTGCAAACTT TCTTGTAGGC TAA

SL1.00sc07408_311.1.1 (SEQ ID NO: 35)

ATGGCGGTCT TATGCTGCGC CACCTCTGCT TATCCTACGC ATACTCTGAG AGTAACTTCT GCTAAAGCTG

CAGTGCGTTC GAGCTCTCGA GTTTCAGTTC CTCAGCTGCA TCATTCCGAT TCCCCGTTTG TTCCCGAGGT

TAATAAGGCT GTTGATTCTT TGTCAAAAGA GTTCAGAGAA GTTGACAATT TAGTGGCACG CAATACTGCG

TABLE 3-continued

CGAGTTTTGA GAGCTTTCCA AAGGGTCAAG GTTGGGTCTC ATCACTTTGG TGGTAGCACT GGCTATGGTC

ATGAAGAAGC TGGTGGGCGT GAAGCCTTGG ACCAGGCTTT TGCAGAAATT GTTGGTGCGG AGTCTGCAAT

TGTTCGATCA CAGTTCTTCT CAGGTACTCA TGCAATCACT TGTGCCTTAT TCGCTTTCTT AAGGCCAGGG

GATGAGTTGT TAGCGATAGC TGGTGCACCT TATGATACTC TGGAGGAAGT AATTGGAAAA AGGGACTCTG

GTGGATTCGG TTCCTTGAAA GATTTTGGAG TAGAATACCG GGAAGTCCCA CTTGCAGAGG ATGGCGGGCT

TGATTGGGAT GCACTTAAAA CCTCTATAAG ACCTCACACT AAGTGTGCAC TCATACAGAG ATCATGTGGT

TATTCTTGGC GTCGCAGTTT GAGTGTCACT GAGATAGGTC GAGCAATTGA TATAATCAAG ATGCAGAACC

CAGGCTGCAT GGTCATGGTA GATAACTGCT ATGGTGAATT TGTTGACGAC ATCGAACCTC CTATGGTGGG

TGCTGACCTA ATTGCCGGAA GTTTGATTAA AAATCCGGGT GGAACGATTG CACCATGTGG TGGATATGTT

GCGGGAAGGA AAAAATGGGT AGAAGCAGCA GCTGCCCGTC TCTCGGCCCC AGGACTTGGA GTTGATTGCG

GTTCTACCCC TGGTGATATA ATGAGAACTT TATTTCAGGG TTTATTCCTC TCACCTCAAA TGGTTGGTGA

AGCAATAAAG GGAAGCTTCC TGATAGCTGA AGTCATGGCG GCTAAAGGTT ATAAAGTGCA GCCACTTTGC

CGGATCAAGC GTCATGACAC AGTGCAGGCT GTACAACTTG GAAATCGTGA GAATCTACTT TCCTTTTGCG

AGGCTGTTCA GAGAAGTTCT CCTGTCAGCT CTTTTATCAG GCCTGTTGCA GGTGCAACTG CTGGCTATGC

ATCTGAGGTA ATTTTTGCTG ATGGAACCTT CATTGATGGA AGTACTAGCG AGCTCTCATG TGATGGACCA

CTAAGAGAGC CTTTCTCTGT TTTCTGTCAG GGTGGCACTC ATTGGACGCA GTGGGGACTA GTTCTGGGGG

AGAAACTGGG GCCGGCAACT GTGGGCCCTC CGAGTAAGTC GGATCGGCAC GTGCATGAGC ATGTGGTTCG

GTGCCACGTG TTAAATGTTC TTCTAGATAT TGGGCCCACT ATCTCCAGGC TCAGCCAATA G

SL1.00sc07408_310.1.1 (SEQ ID NO: 36)

ATGGAATTGG ATCTGGATCG TGGGCAAGTC ACACTGATAG CATCCAGTAT ATGTCTTATG CTGACTTTAC

ATTTCAGCAT ACAGCTAGTG ACAGAACATT TTACGTCATG GAAGAAGCCT AAAGAGCAAA AGGCCATAAT

TATTATCGTC CTCATGGCAC CTTTGTATGC TATTGTCTCC TTCATTGGGT TGGTCGATTT CATGGGAAGC

AAACCCTTTT TCACTTTCTT GGAATCTGTC AAAGAATGTT ATGAAGCAAT TGTGATGGCT AAGTTCCTGG

GGTTGATGTA CACTTACTTG AATATATCCA TAAGCAAAAA CATAGTCCCT GATGAAATTA AGGGAAGACA

GATTCACCAC TCATTCCCAA TGACACTCTT CCAGCCTCAC ACTGCTCATT TGAACCATCA TACATTGAAG

CTTCTCAAGA ACTGGACATG GCAGTTTGTT GTGATTCGCC CTGTATGCTC TATTTTAATG ATTGTTTTAC

AAATGTTTGG AGTGTACCCT AGTTGGGTTA GCTGGACCTT TACCATCATT TTAAACATAT CCGTTTCACT

GGCATTGTAC TCTCTTGTGG TTTTCTACCA CGTGTTTGCG AAGGAGTTGG CGCCTCACAA GCCACTAGCC

AAGTTCCTGT GTGTCAAAGG AATTGTCTTT TTCGTCTTCT GGCAGGGCAT TCTGCTTAGT GTTCTGGTAT

CACTAGGCAT AATAAAATCT CACTATTTCT GGCTTGAGGT GGAGCGCCTT CAGGAAGGTA TGCAGAATGA

ACTAGTGATC CTGGAGATGG TTTTCTTCGC TATCCTTATG CGTCATGCAT ACAGTGCAGC GCCATATCGC

GCAGAAGCTG TTACAACTAC TTCAGAAGAT GCTACTTCTG GAGATAAAAA GAATGAGTGA

SL1.00sc07408_309.1.1 (SEQ ID NO: 37)

ATGACAGCAC TCGCTCAAAT TCTCATTAAT TTATCACCCT AAAAACACC ACATGATGCT TTGTATAGAA

AACCGAACTT TCTTGGGCTG AAATTACAGC GACCCAGTTG TTGTTTCACT AATTTAAGGG CAAGAAAAGT

GTCAATTTGT AGTAGTTGGT ATAAATTAGG TGCTTTTAAG GAGAAAAACT CAATCTTGAC AGATAAAAAT

GGGATTTTTA TGAAGGAGGA GAGATGGGGT TGTGAGAAAA GAATGGTTTT TGTGAAATTT AAACAAGGTT

TTGGATTGGA TGGGATTGGT GATGGTGGGG GTGGTGGGAG GGATAATAGT GAGACTGTGA GAGTGTTGAG

TAATCTTGTT TTAGCAATTG GCTTACTTA TCTTACTATG ACTGGTCAGC TAGGTTGGAT CTTGGATGCT

ATTGTTTCTG TTTGGCTCCT TGCAGTTCTA CTTCCAATTT TAGGTTTGGG AGCTTTTATT TGGTGGGCTG

TABLE 3-continued

GACGAGATAT TGTTCAAAGC GCTTGCCCAA ACTGCGGGAA TGAATTTCAA ATTTTCAAGT CTACTTTAAA

TGATGAGGTT CAGCTTTGCC CTTTCTGTAC TCAGCCATTC TCAGTTGTTG GCAATAAGTT CGTGAGAGAC

CCAGTAACGT TCTCCAACCA GTCAACTACA TTTGGTCAAG CATTTGGTGA TTTCAGTACT CGTTCTAAGA

AAGGTAAGAA TTCCTCTGTC GGAATTGTTG ATATAGAAGC AGAAGTTAAG GACGCGGACT AG

SL1.00sc07408_308.1.1 (SEQ ID NO: 38)

ATGGCGGCGT GGACGGCGGC GGCGAGGCAA GCAGCGAACC TATATCGATT CTCAGCTTCT AAATCAGTTA

GCTCAACGAA GCAAGGCGCT TTACTTATCC AGCGGCGCGG CCTTGCCGGC GGTGGTGATC ATCATGGACC

TCCAAAGGTG AATTTTTGGC AGGATCCGAT GAGTCCGTCT AAATGGAAAG AAGAGCATTT TGTGATCGTC

TCTCTTACTG GTTGGGGGTT GGCCTTCTAT GGAGGTTATA AGCTCTTCAC AAAGGGAAAG AAGAGGAGA

AGGAAGAGAA AGTTGGTGAA GGATCCCACT AA

SL1.00sc07408_307.1.1 (SEQ ID NO: 39)

ATGAATGAGA AGGCTAATGT TACTAAAGAG CTTAATGCGA AGCATAGAAA GATACTAGAA GGACTTCTTA

AGTTGCCCGA GAACAGGGAA TGTGCAGATT GCAAAGCCAA GGGTCCTAGA TGGGCAAGCG TGAACCTGGG

AATATTTATA TGCATGCAAT GCTCTGGGAT CCACAGAAGC CTGGGGGTGC ACATATCAAA GGTCAGATCA

GCTACACTAG ACACATGGCT TCCTGAACAA GTTGCATTTA TCCATTCAAT GGGAAATGAG AGGTCAAATA

GTTTTTGGGA AGCAGAGCTG CCTCCAAATT ATGATAGAGT TGGTATTGAG AATTTCATCC GAGCAAAATA

TGAAGAGAAG AGGTGGGTCC CTAAGGATGG GATTCAAAAA TCACCTTCCA GGGTTCAAGA AGAGAGGGCT

TCGGTGCAAT GGCAACAAAA CAATGATAGA AGTGGGCGTA TACATGCAGC TAGCTCAGGA TGTGCATCTG

ACGAGAGGAA AAATATTCAA GCCTCGAAAG TGAAGCAAGA TGTACCTGCT GCTAGAGTCA GTATACCAGT

GCCTCCTAGA GGACCAGAGC ATGTAACTTC AGGTCAGGTT GCTAACCAGA CAAGTCAGAA AGCAGAGCCA

GTTGCAGTCA CTGAACCAGC TAAGCAGGTT CCGGAAGCTG CCAGTCCTCC TAAAGTTGAT TATGCTACTG

ATCTATTTGA CATGCTTTCT ATGGATTGTC CAACTGACAA TGGCTCAGAA GCAGCTTCTA CCGATGATAA

CTCCTGGGCA GGCTTCCAGT CTGCTCAAGA AGCAACAAAA GCAGAAAATA CTGGGGTTAC AAACTCCGTT

GATCAGAAGA AGTCTCAATC TGCTGCTGCT TCTGGAATTG AAGATTTATT CAAGGATTTA CCATCAATTG

TGCCTTCTGC CTCATCGCAG AAGCCACAGA AAGATGCTAA AAACGATATA ATGAGCCTTT TCGAGAAGTC

CAATATTGTG TCACCTTTTG CTATGCATCA ACAACAACTT GCTATGCTGG CGCAACAACA GTCTTTACTG

ATGGCTGCGG CTGCTGCAGG TGGTGCTGTA AGACTTCCTG TAAATGCACA ACAAAGCACT AATGGCACCA

ATATGGTAAA TCAGAACTGG CCAAATTTAG GCTATCAGTT CCCTGGAGTG ATAATGCCAG CAGCTGGTAA

GACTGAGCTG GAGAAATATA TGCAGGTAGG CAATATGGGA CCAGCACATG TAGTTGGAAA CTCTGTGCCA

ATTCCAGCAT CCAGCTTCTA CTCAATGGGA CAGAACACTT CCAGCAACGG TATTGTGCCG CCAGGACCAA

GCAAGCAAGC AGCTACCCCG ATATCATCAA GCTCCACACA GTCAACAAAA GAATTCGACT TTTCATCCTT

GACACAGGGT ATGTTCACAA AACGCTGA

SL1.00sc07408_306.1.1 (SEQ ID NO: 40)

ATGGCGATTT TGTTTCAAAG TTCAAGTAGC TCCATGTTAT CTATCAAAGT TTTTCTGATT TCGACTACTG

TTTTATCTGC TGCTATTATG TTAAAGGTGT CTGCTCCTGT TGTTACTGAA TTCGCGGTCA GTGAAGTTCC

GTCGATCTGG AACGGTGTCG TTTCGTGGCT TAAACCTCCG TATCTATACC TTGTTATCAA CTGCATTATC

ATTACGATTG TAGCCTCTTC TAAGTTGCAG AACAAGCTTG ATGAGAACTC ATCTCCGGTG CCGGCGGTTG

TTTCGCCGGA GAACTCGTCC CAGTTTCACC CGATTAAGGA TGTAAGGCCG GTTACAGACT ATTATACACC

GGTCCTTCAT GACTTAAACG GCTCCGTGCT GAAGAATCAA GCAGTGGAGG CGGAGGCTAG ACCGATAGTT

TACGAGTATC CTACTGCTGG TGTTTATGAT GCAAAGGTCG AGAAACTTCC AGTAGTTAAT CCGTACATAT

TABLE 3-continued

CGGAGAAAGG TACATCGTTC AACACCTATC CGGAGCCTAA CGATGTTGTT GCTGAAAAGG ATGATTTCGT

AATCTCGAAA TCTTCTTGGG CGCCGGTGAT GAGACAGGAC TCTATTGATT ATTCCATTTC AGGCAACTCG

GCTGAGAAAC CTCCTGCTTC TGCCAGATTC GCTCACCGGA GAAATGTCAA ATCCACTCCT GAAGGTGGAA

AGGGAGCATT GAGAGTATCA AAACCTAAAC GGCAAGACAC GCTGGAGAGT ACATGGAAGA CGATAACGGA

GGGCCGTGCA ATGCCACTAA CGAGGCACCT GAGGAAATCG ACACGTGGG AGACATACGG TGGTCGGAAC

CCGGTTACAC CACCACCGCA GAAGATGAAG AAATCTGAGA CGTTCAATGA CAGAACTACC CCTGACTCCT

CGCCATTGCT GACTCCGTCC CCGGGTGGTT CAGGGAAACT TAAGAAAGAG CCATCGCTAA GTCAAGACGA

GCTGAACAGG CGAGTTGAAG CGTTTATTAA GAAGTTTAAT GAAGATATGA GGTTGCAGAG GCAGCAGTCG

ATGCAACAGT ACACTCAGAT GATCAATCGA GGCTCACATT AG

SL1.00sc07408_305.1.1 (SEQ ID NO: 41)

ATGGCGCTCC AGCACTCGCC TATTGGCACA ATTACTTCTT CAGCTCAAAT GAAGCTGGCT GTTAGCAGTT

TGAGGTGCTA CGAGCACCTT CGTCCTATCA CTATCTCAAG CTTCAAGCGT TTTCCACGAA GAATTCAGGG

TGCGCATAGT AGTGTGGAGC AAAGGAAGTT GCTTAGCAGA GGTATTTCGA CAAGCAAAGA AAAATCGAAG

GATCTCCATG AAGATGTTTT TTCTTTGCCA ATGGCTTGCA CTAGTGCCCC AATTAGATTC ACAATGCTCT

CAACTGCTGT CATAGCCACA AATTTGGTTG CAACACATAC CGCAAATGCT TTGACTATGG ATAACATGAT

GGATTTCTCT AGCGCTGTCT ATACATTAGC TGATGGAAGC ATTGGAGATC TTTTTGGTGG CCTTCTGTAT

TCTGCTGGTC AACAAGCTAA TGAAGCTGTT CAGGGCCAGT TGACTGCTCT TAGTTTTACT AGTTTGGCCA

CTATTTTTGG TGCCGGGCTT GTAACTAGTC TGTCGCCTTG TACACTCAGC GTACTGCCTC TGACCCTTGG

TTATATTGGG TGCCGGGCTT CTGGGAAAAG CCGAGTAGCG GTTGTTGGAG ATTCAATTGC ATTTGCACTG

GGATTGGCAA CCACACTAGC ATTATTGGGT ATTGCGGCTG CATTTGCTGG AAAGGCATAT GGACAAATAG

GACAAGGATT GCCCGTGGCT GCTTCCTTTT TAGCTATTGT TATGGGGCTA AACCTGTTAG AGGTAATAGA

GTTGCAACTT CCCTCATTTT TTGACAACTT TGATCCTCGC TCAGCCGCTG CTAGCTTTCC GTCCAGTGTT

CAAGCTTATT TGGCCGGTCT TACATTTGCA TTAGCTGCAT CACCATGCAG TACACCAGTC CTCGCAACCT

TGCTCGGCTA TGTTGCTACT CTCGGGATC CAGTTATTGG GGGCAGCTTG CTATTGACAT ACACAACTGG

CTATGTTACT CCCTTACTTC TTGCTGCTTC TTTTGCTGGA GCATTGCAGA GTATACTTTC ATTCCGCAAG

TTCTCAGCAT GGATCAATCC AATCAGTGGT GCGCTACTAC TAGGAGGGGG TGTCTATACC TTTCTCGACA

AGCTTTTTCC GGTGACGATG GCTATGTAG

SL1.00sc07408_304.1.1 (SEQ ID NO: 42)

ATGGCGAAGA ACAGAAACAA GAAGAAAAAC GGCCTAGCTG CCATGGATGT CTCCACTGAC CAGACGGTCA

TGGATGCCCA AGCGATGGAT ACTTCAGAAT CAGCTGCTCC AAAACCACAT ATAGGTGGAT CACTTAGAAA

GACGAAGGGA GTACAAATGA AAAGGACGAA GAATGTTAGG AAAAAGAAGG CCATGGCAAA GGCTATTTCA

AAAAGTGAGA AATTGGAGGA AAGAATCACT AGGAGTGAAA GCAAGATAGA GAGAACTAAA AATGCCAAAC

AGTTATACGA ATGA

SL1.00sc07408_303.1.1 (SEQ ID NO: 43)

ATGGATTTTG ATGTCCAGGG GGGAAAAATG TCTACTATAG TTCGTAGTTC GTTAGAGGAA ATGCTGGATT

CTCTCCGGCA AAGGGATGAA AATGAGAAGC AAAAGACTT GCCGCCGGCG TTGCCTGCTC GGCCTAAGCT

TACATCGAGG ACTAGGCCTC CTTCACAGAG GCAACCGTTG AGCAAAAGGT TAAGCAAAGG TGATGTTGAA

TTGGAGAATG GTAAGAAGAA GGAGGAGTTG AAAGTGTTGA AAAGGAATGT TTTTGGTGCT ATGAAGGTGA

AAGGAATCGA AGATAGCGAA TCGCCATATG CAATGCCTTC AGTGAAGAAA ACAGCACAG GGAGATTGCG

GGAAGTAAAT GGTGGGAAGG TTGAGAAATG GCGTAGTGAA GCTGAATGGG ATGATCGGCT GGATTATTTT

TABLE 3-continued

```
GTTAAGAAGA AGCTTCGCAT CTGGTGTCGT CTGGGGAATG GGGCATGGGT ATCAGGACAT ATTCAATCAA

CTTCAGGAGG GAAAGCTATG GTGTTGCTTT CTGACGGCAG TGTTGTGCAA GGCAGGGCCT GTATTAATAG

ACCTTCTAAT CCGGATGTTC TTGAGGGTGT GGATGATCTC ATGCAGCTTA GTTATTTGAA CGAGCCATCT

GTTCTTCACA ACCTTCAACA CAGATATGCG CGAGATATGA TATATAGCAA GGCAGGGCCT GTATTAATAG

CAATCAATCC GTTCAAAGAT ATCCAATTGT ATGGAAACGA ATTTGTTACA GCTTACAGAC AGAAGCTCTT

GAGTGATCCT CATGTTTACT CTATTGCTGA TTCTGCCTAC GATCGAATGA TGGAAGATGA GATAAGTCAA

TCTATTATCA TAAGTGGGGA AAGTGGATCT GGGAAGACGG AAACAGCAAA ATTTGCAATG GAATACTTGG

CTATGCTTGG TGGAGGTAGT AATGGGATAG AGAAGGAGGT TTTGGAAACA AGCTACATAT TGGAGGCCTT

TGGGAATGCC AAAACTTCCA GGAACAATAA CTCCAGTCGA TTTGGAAAGT TGGTTGAAAT TCATTTTAGT

CCAGCAGGAA GAATATGTGG TGCTAAAATA CAAACCTGTA AGTGTAATTG TCCTTTGTCG AGAGTGGTTC

AGCTGCTTGA TGGAGAGAGG TCCTATCATA TTTTTTACCA ACTATGTGCC GGGGCTCCAC CTACTTTAGT

AGATAAACTT AAGTTAAAAG GTGCATCAGA ATACAAATAT CTCAACCAGA GTGGCTGCTT GGTGATCCAT

GATGTTGATG ATGCTGAGGA ATTTTGTAAG CTTATGGAAG CCTTAAATAC TGTTAGGATT TCTGAAAGGG

ATCAAGAGCA TGCTTTTCAG ATGATTGCTT CAGTTCTATG GCTGGGAAAC ATAACATTCC AAGTAATTGA

CGATGAAAGT CGTGCTGAAG TTGTGCAAAG TGAAGCTGTT ACAAATGCTG CTAGCTTGAT TGGCTGTACT

GTAAATGACC TCATACTAGC TTTGTCAACA TGCCAAATAC GAGCTGGCAA GGATAAGTAC GCCAAGAGTT

TAACTGTAGA GCAGGCAACT GATAGAAGAG ATGCATTGGC AAAGTTCATT TATGCAAACT TGTTTGACTG

GATAGTAGAT CAAATGAACA GAAACCTTGC AATGGACAAA GAACAGATGG GTAGATCCAT AAATATTCTA

GACATTTACG GTTTTGAATC ATTTCAGGGA AACTCATTTG AACAATTTCT GATAAACTAT GCAAATGAGA

GGCTCCAGCA GCATGCCAAC AGACATCTAT TGAAGCTCGA GCAAGAGGAA TATGAATTGG ATGGAATTGA

TTGGTCAAAA GTAGATTTCG AAGACAACCA AGAGTGCCTG AACCTTTTG AAAAGGTATT CTTCCTTTTG

GTTCTTTTTC CTATTTATAT GGCGTTAGGA GCTTATATAA GCCGACAACT TTCTTCTGCC CCGGATAGCA

TGTTTACATT CAAGCCAATT GGCCTTATAT CTTTGTTGAA TGAAGAATCA AATTCCCTTA CAGCCACAGA

TTTGACCTTT GTATGTAAAC TTAAGCAGCA CATCAAATCT AGCCCTTGCT TTAAAAGTGA AAGAGAAGAA

TTTTGTATCC GTCATTATGC TGGAGAGGTC AGTTTCTCTT ATAAATGCAT CCTTTCTAGT TCTGTGCAAT

TTCTACGGAT ATTATTAGTA TTTTCACTAT TTTGGTTAAG AGACTTGATA GCTTTCACAT CCCCATGGTC

AGACTTACGC TCAATTGTTG GGAGAGTTTT TCTTTCTTAT CATGGTTTTA TTACAGTAAC TTATGATGCA

ACTGGCTTCT TAGCAAAGAA CAGAGATGTG TTGCATCCTG ACATTACTCA GCTACTCTCA TCAAGTGACA

GTCACCTGCC TGAAGATAAA AAATTATCAA TTCCATCAAC TGATGCAGGA GTGCTAGATT TTCAGAAGCA

AAGTGTTGCA ACTAAGTTTA AGGATAATTT GTTCAAATTG ATGCAGCAAT TGGAAAATAC CATACCACAT

TTCATATGTT GCATAAAACC AAATAATAAG CAGCTTCCTG GCATGTCTGA CAAAGATCTT GTCATAGAAC

AACTCAGATG CTGCGGTGTT CTTGAGGTGG TTAGAATATC AAGATCTGGC TATCCTACTA GGTTAACACA

TCAAGAATTC ACAAGCAGGT ACGGCTTCCT TCTGCCAAAG GATAGTGCAT GCCAAGATCC TTTAAGTATG

TCAGTTGCCA TTCTTCATCA ATTTGGTATT CTTCCGGAAC TGTACCAAGT TGGGTATACC AAGTTATATT

TCCGATCAGG ACAGATTGCT TCATTGGAGG ATGCAAGGAA CCAAGTTCTG CAAGGTACTC TTGAGTTGCA

GAAGTGCTTC CGTGGTCATC GTGCTCGTCG GCACTTCCAT GAACTGAAAG GAGGAGTAAT CATACTTCAA

TCATGTAAAG CAGATCCCTT TGCAACTCGT CTCTTTTCTT CCCTTTTTTC GTTGAATATA ATAGAAGATG

ATATTCATGA AGATTGTTGT GTCTATCAGG TTGGATGA
```

TABLE 3-continued

SL1.00sc07408_302.1.1 (SEQ ID NO: 44)

ATGTCTAAAG CGAAGGTTGC TCGTGAAGGA AGTGATGAGC AACTGGTGGC TGTCGTGCAG ATACAATCAG
CTATTCGTGG TTGGTTGGCT AGAAGGGGTC TTCGCAAACT GCGAAATTCA AAAATGTTAA ATGTAGACAA
ACGAAGATCA GGCAGAAAGA CGGAGGTCAA GGAGTTGCCT CGAGAAATCC TACCATCTGT TGTAGAAGAC
CTCGAAAGAC GGGTTGCAAA GGCCGAGGCA CAACTGAAC AAAAGGAAAA GGAAAATGCT GCCCTGAAGG
AACAAGTAAA CCAATTCGAG ACCAGATGCT TAGAATATGA GGTCAAGATG AGGTCAATGG AGGAGATGTG
GCAAAAGCAA ATGACATCAT TGCAGGTTAG TCTAGCTGCA GCCAGGAACA GTCTTACCGC TGCTGACACT
ACTGGTCGAC CTGGAAAGCT TGAAGGTTCC CCATCTCCTC AGTATTATGA TTCTGATGAT GCAACATCTA
TGGACACTCC TGCGGGACGC ACTCCAGTTA GCTTTTCTAA CAACAGCTTG GGTGTTGTAG CTAATAGAGA
GGTTAATGGT GGTTTATCCT TAATCAGCCA CCTTGCAATG GAATTTGAGC AACGGAAGCA AAATTTTGAC
AACGAAGCCA TGGCAATTGT TCACTTGAAG CCAGGGCAGT TACAGTCTAC TAATAATCCT GCAGATGAGT
ATCGAAGACT GAAACACAGG TTTGAGGAAT GGAAAAAAGA GTACAAGGTT CGGTTAAAGG AGACAAAGTC
AAAAGTACAC AAGCTTGTTC ATTCTAAAGC AGGGAAGAGT CGTAGAAAAT GGTGGGGTAA AAGAGCAAA
TGA

SL1.00sc07408_301.1.1 (SEQ ID NO: 45)

ATGGCAGCAA CAGGTAGCTC AGCCACAGTT GTTAGAGCAA CTCCATTTTT GGGCCAGACC AAATATGCTA
ACCCCCTAAG GGATATAGTT CCTATGGGCT CTGCCAGATT CACCATGAGT AATGATTTGT GGTATGGACC
TGACCGTGTC AAGTACTTGG GACCATTTTC TGCTCAAACT CCTTCATACT TGACTGGAGA ATTCCCTGGT
GATTACGGAT GGGATACTGC TGGTTTATCT GCTGATCCCG AGGCCTTTGC TAAGAACAGA GCTCTTGAGG
TTATCCATGG GAGATGGGCC ATGCTTGGAG CTTTTGGTTG CATTACACCA GAAGTTCTTG AAAAATGGGT
AAAAGTGGAC TTCAAAGAAC CAGTATGGTT CAAAGCTGGA GCCCAGATCT TCAGTGAAGG TGGGCTGGAC
TATTTGGGCA ACCCAAACCT TGTCCATGCT CAGAGCATTC TAGCAGTATT GGGCTTCCAA GTTGTACTAA
TGGGCCTTGT AGAAGGTTTC AGAATTAATG GGCTTCCTGG AGTTGGTGAA GGCAACAATC TCTACCCAGG
TGGACAGTAC TTTGACCCAT TGGGCCTAGC AGATGACCCA CAACTTTCG CGGAACTCAA GGTCAAGGAA
ATCAAGAACG GAAGATTAGC TATGTTCTCC ATGTTTGGAT TCTTCGTTCA AGCTATTGTC ACCGGCAAAG
GCCCACTTGA AAATCTATTG GATCACCTTG ACAACCCTGT TGCTAACAAT GCATGGGTTT ACGCAACTAA
GTTTGTTCCT GGATCTTAA

SL1.00sc07408_300.1.1 (SEQ ID NO: 46)

ATGTTGGAAG GGAAAGCAGT AATTGGAGAT ACAGATATGT TGGGAACCAT GCAACAAGAT GCATTAGATT
TAGCTGCAAA GGCACTTGAC TTCTTTGATG TCACTGAGGC CACTGAAATT GCACGTTTTC TTAAAAAGGA
ATTTGATACA ATGTATGGAC CAGGGTGGCA ATGCATAGTA GGGACAGATT TTGGTTCATT TGTAACACAT
TGTTATGGTT GTTTCATCCA TTTCTACATT GGCAGCCTTG CTATTTTGCT CTTCAAGGGC TCTGCTGCCC
TAGAGGACCC GAAAGCCGAG GCCGAAGCTG ACCGATTTTC CACTCTGCAG GAAATAGCAT GA

SL1.00sc07408_299.1.1 (SEQ ID NO: 47)

ATGGGGCGCC GTCTCTTCAC CTGCTTCGGC AAAGGCGGTT CTTCTCATTC TTCTTCAAAA GATCCCGGCT
CGAATAACAA GGACAGTGCG ACGGCGGATT TGACGGCGGA GGAGCAAAAA CGGTGCGGGC CGGTGGTGGT
GGAGTTATTC TCATCGCAAG GCTGCGCCAC CTCACCTGAA GCGGAGCTGT TGTTTTCAG GATTGGGAGA
GGCGATTTTA ACCTAGAAAT GCCGGTGATT TTGTTGGCTT ATCATGTGGA TTATTGGGAT TATATGGGTT
GGAAGGATCC GTTTGGGTCG AGTTTATGGA CGGTTAAACA AAAAGCGTAT GTGGAGACCT TAAATCTAGA
TACCATGTTT ACGCCTCAAA TTGTGGTTCA GGGAAGAGCT CAATGTGTTG GAATGAACA AGATGCGGTT

TABLE 3-continued

TTCTCTTGTA TCAAATCTGC CCCCAGATTT GCTGCTCCTT CCTTCCAGGC AACATTCGAG AGGCCAACAC

CAGAGTCATT GCAAGTATCT CTATTAGGAT CTCTAAGGAG TAAGGTGGAC AATGATGGTC CCAACGTGAT

GATTGCTCTG TACGAAGGTG GTCTGGTGAC TGATATCGCT GCAGGAGAGA ACAAAGGAAA AATGCTTGCG

AATGACTATG TTGTCAGGAG GCTGGAAAAG CTTTGCTATG TAAAGGATAT TACTGCAAAG AAGACAATCT

CAGGAACTGT CAATTTCTCT CTTTGGGATG GCTTCAATAG CAGCAAATGT GGCGTAGCGC TCTTTGTGGA

ATCTGGCTCT CATCAAATAT GTGGATCACA AAACTTTAAA TTGCCAGAAA ATCTCTGA

SL1.00sc07408_298.1.1 (SEQ ID NO: 48)

ATGGCAATCG CCGACCACCA CAAGTCACAT AACTCAGACG GAAAGCTCTG GAAGCTTTGT CCTCTATGGC

AATCAGGAAC TACGTCTTCT TCTTCGTCGT CTACACAAAA TCTTCACTCT CAGAATCACA TGCACCAAAA

CGGCGTCGGA TCTAACAGCT CTCGTGCTTC TACGTCTGTT AGCTCCGTTG CTAGATCACT GCTTCCGGCT

AGACGTAGGC TTCGGCTCGA TCCAGCTAAC AGTCTCTACT TCCCTTATGA ACCGGGAAAG CAGGTGAAGA

GTGCTGTAAA GATTAAGAAC ACTAGCAAAT CTTATGTTGC ATTTAAGTTT CAAACGACTG CACCAAAGAG

CTGCTACATG CGACCTCCCG GAGGCATTCT CGAACCCGGT GAAAGTGTTA TTGCCACTGT CTTCAAGTTT

GTGGAGCACC CTGAGAACAA CGAAAAGCCT GTGGACCAAA AGAGCAAAGT TAAGTTCAAG ATCATAAGCT

TGAAGGTGAA AGAAGGTGTA GATTACGTAC CTGAGTTGTT TGAAGAACAA AAGGATCACG TGACTATTGA

ACGTATCCTA CGGGTGGTGT TCTTGGACCC AGAACGACCT TCTCCAGTGC TGGATAAACT AAAGCGTCAG

TTGGCTGAAG CTGAGGCAGC ATTAGAATCT CGCAAGAAAC CTCCAGTTGA AACTGGACCT AAAGTTGTAG

GAGAAGGTCT AGTAATAGAT GAATGGAAGG AACGAAGGGA GAAGTATCTC GCTCGGCAGC AGGTTGAGGC

TGTTGATTCA GTGTAA

SL1.00sc07408_297.1.1 (SEQ ID NO: 49)

ATGAATGCAG CAGCAGCAAA GGGATCGGCA TGGATCGTAG CAGCAAGTAT TGGAGCAGTA GAAGCATTAA

AAGATCAAGG ATTTGCCAGA TGGAATTACG CTTTAAGATC GATTCATCAC TATGCCAAAT CTAATTTAAT

TGCTTCTAGT AATACCTCGG CTCGGAGATT CTCGACGGCT TCGGCGCCGG CGGCGTCTTC TCCGGCAGTC

GTCTCCGGTG AGAAGCTGAG GAAAACGGAA GAGACGTTGA GTAAAGTTAT AGATCTGAAC TGTTGGGGTC

CAAGCACTGT CAGATTTTAG

SL1.00sc07408_296.1.1 (SEQ ID NO: 50)

ATGGAGCTTC TCCGATCAAA CCTTGCTCGT GTTCGGATTC CAGAGCCGAC TACTCGTATC TACAAGCACG

AGTGCTGCAT TTCTTTCGAT ACTCCGAAAT CCGATGGCGG GCTGTTTGTT GATATGAGTA CTTTTCTTGC

ATTTGGAAGG GATTGTGTTG ATTGGAACTA TGAGAAGACT GGGAACCCAG TTTATTTGCA TATAAAGCAG

ACAAAGAAGG CAGATGCTGA AGATAGACCG TCCAAAAAAC CCACTCTCTT GGCTATAGGT TTAGACGGAG

GGTTTGATAA CAGTGAACCC CAGTACGAAG AATTCTATGA AATAGTTATA TTGCCTGATA ATGTCACTCT

TCCTTTCCCA TCGGTGGAAT TGCCTGAGAA GGTTAGATTG GCTGTTGATG CTATTTTACT AGCTGAAGGT

GCTGAGAGGA AAGAGCAACT TGCTTCCTGG ACTGCTGACA AGAAGCTTGT CAGTAAATAT GCTACGGATC

TGCAACAGCT TGACAATGGT GTTGCTGTTC CACCTGTGGG TTGGAAATGT GCGAAATGTG ACAAGACTGA

CAATCTTTGG CTGAATCTAA CTGATGGAAC TATCCTATGT GGTAGGAAAA ATTGGGATGG AACTGGTGGT

AATGACCATG CAGTTAACCA TTACAAAGAA ACTGGTTATC CACTTGCTGT AAAGCTTGGG ACCGTAACTG

CTGATTTGGA GGGGGCAGAT GTTTACTCCT ATCCAGAGGA TGAAAGTGTT GTTGACCCAC TTTTAGCAGA

TCATCTGGCA CATTTTGGTA TTGACTTCTC ATCCTTGCAA AAGACTGAAA TGACGACTGC TGAGAGAGAA

CTAGACCAAA ATTTTAACTT TGATTGGAAC CGGATTCAAG AGACTGGTGA GGACGTTGAA CCACTTTTTG

GACCTGGTTA CACTGGATTA GTCAATCTTG GTAACAGTTG CTACTTGGCT GCTACAATGC AGGTTATGTT

TABLE 3-continued

```
CTCAACGCGT TCATTTTGTT CAAGATACTA CTTTGATCAA CGTCTGAAAG AAGCTTTTAC TACGGCTCCT
GCTGATCCGA CTGTAGACCT AACATGCAG CTAACAAAGC TGGCTCATGG TTTGCTTTCT GGTAAATATT
CGGGTCCTGT TCTGGAGAAG GATAATACTG CTAATGCTGT AAGCTCACAG AAACAGGAGG GTATCCGTCC
TCGAATGTTC AAGTCAGTAA TAGCTGCTAG TCACCCTGAA TTTTCAACAA TGAGACAACA GGATGCGTTA
GAGTTCTTCC TGCATTTTAT TGATCAAGTT GAACGGATAA ACTCTGGGAC ACCTAATTTT GATCCATCAA
GGAGCTTCAA GTTTGGTATT GAAGAACGCC TCCAATGTTC CTCGGGCAAA GTCACTTACA ACAGAAGGAA
TGATTATATT CTGTCTCTTA ATATTCCTTT GGAGAGGGCT ATAAATAAAA AAGAGCTAGC AGAATTTCAA
AATTTGAAGG CTGAGAGAGC TGCAGGAGGA AAAGAACTGT CTGCTGATGA AATTGTTCGC CCTAGAGTAT
CATTGAAGGA TTGCCTAGAT TGCTTTTCAG CTCCTGAGGA GGTGCATGAT TTCTACAGCA CAGCTTTAAC
AGCTAGGACT ACAGCAATCA AAACTGCAGG TTTGACTTCT TTTCCAGATT ATCTGGTTTT GCACATGCGG
AAATTTGTTA TGGAGGAAGG TTGGGTGCCA AGAAGCTCG ATGTCTACAT AGATGTCCCT GAAACCATTG
ACATAAGTAG CATGCGAAGT AATGGTATTC AACCAGGAGA AGAGCTGTTG CCTGACAGTG CTGCAGGGGA
TGGTGAGCAG TCAATAAAGC TTCTGGCTGA CGATGATATT GTTGCACAAC TTGTTTCAAT GGGATTTAAT
CTACTTCATT GTCAGAAGGC TGCTATCAAT ACTTCCAACA GTGGAGTAGA GGCAGCAATG GATTGGTTAC
TTAATCATAT GAATGATCCA GATATTGATG CTCCTATATC AGAAAACGTG CAAAATCCTG ATATTGATCA
ATCTAAAGTT GATACGCTGG TTTCATTTGG TTTCGAAGAG AAACTTGCCC ATAAGGCCCT GAAGGCATCG
GGAGGTGATG TTGAAAAAGC TACTGAATGG ATATTCAGCA GCCCTAGTGC CAGTACTGCA GCAGACATGG
ATGTTACTAC CAGTAGTGGA GCTGCAGTTG ATACCTTGAT GCCTGATGGA GGAGGAAAAT ACAGGCTCCT
GGGATTCGTG AGCCACATAG GCACATCTAC CCACTGTGGC CATTATGTCG CTCATATTAA CAAAGATGGC
CGGTGGGTGA TTTTCAACGA TGAAAAAGTT GGGGTCTCAA AAAACCCCCC TATGGATATG GGATACCTCT
ACTTTTTGA AAGACTTGAG AGTTGA
```

SL1.00sc07408_295.1.1 (SEQ ID NO: 51)

```
ATGGCAAAAT TAGCGAAAAA TCGAGGAAGG AATAGATTTT TTAATAGTTG TTATAAGCCT CTACATTTCA
ACGATGATAT ATCTAATACA AATAAACGAG GTCATTTGTA TAATTCAACA GATATATCTA ATTTGAAGAG
AGTAAAATCA CAAGAAAAAT TGGATTCAAT GTTGGGAAAA GATTTGACCA AAAATTTTCG ACCAAATCGA
AAGGAGAATG CCTTTGGAAG GAATTTTTCT CATGCACTCA AAATGTGTT TTTTGATACA TCATTGGGGA
AGAAAGGCCA GAGGAAAGAG CATAAGTATT CATTTGGATC ATGTAAAAAG TTATCAACAA AATTTGAGAA
ATATTTCAT TCTACAAAAG AAAAAAAGTT TTCTTCATCA AAGGATTTAC CAAAAATTAC AAGTAGAATG
TCCACAAGTG CAAGCATGGA TGATTTTTCC TTATTCACTA CTTCTACATC CTCTTTATTT TCTTCTTCTT
CTTCTTCTCG TTCGTCTTGT TCATCACAGA GAACGCAATT TTCATCTTTT CACAGGTCAA AATCAGAAAA
CAATATGCAA GTGTATGATA ACGTAAAAGA AAAAGATATC GCGCTATGTT ACAACAAGAA CGTTGGGACG
TATTCTCTTT TAATTTGTCT ATTGGTTATG GTTTTTTGTG GGAAAGTTTT TGCCATCATT TGCACTTCAA
CATGGTTCTA TTTTGCTCCT CATTGTTTCA AACGTATAGA CTCGGATGAG TACAAGAAAA ATGATGGATT
GTTATATTTA GTACAAGAAA AAAATCTAAC TTTTTAG
```

SL1.00sc07408_294.1.1 (SEQ ID NO: 52)

```
ATGGCTACTT CTCTTCAGTT TTCTTCAGAT CATCACCCTA TTCCTCAGGA AAATCATCAA ACAACGAACC
AGACCTCAAC GGGAGGACGT AGAAGGTCGA GTAAAAATGG ACAGAAGAAG AAGAAGCAAC CACAAAGAGG
AATGGGAGTT GAACAACTCG AACGTCTTCG AGTACAAGAT CAGATGAAAA ACAGTACTAT CCATGGCGTT
CATCATAATC ATCAGTACTA CTCTAATAAC AATTTCCCTA AATTAACTCC TGTTTCATCA TTTACCGGCG
GTGGTAGTGC TAGTGCTGAT CCTGGAAATT ATAGTAATTC TATTTTGAAC TCTTCACCAG TACTTCAGTT
```

TABLE 3-continued

```
CCCCAAATTG TGTGCAGTGA GCCCTAATGA TTTTTTTATG CAACAAAAAG TTGTGAATAC TGGGTTTATT

GGATCTAGTA GTACAAATCA GTTGATGATT TCTTCTCATG ATCATCATCA GTTTCAATCT CAGATGAATC

TCTACGGATT TGCAACTTCT AAGCCCAGTA CTGAGAAATC AAAGGAGCTG TATCCAATGC CAAATCTGTT

TAGCAGCAAC AACTCTTGTT TCTCCGATCG CTGCCGATCA TGCAACAAAA AGAAACGCAT GATCAATGGA

GAAGAAATTA GCGTTCATAT GGAGGACATG ATCAGAGAAA AGGAAGATTC TGGAACAAAG CCTTTGCTTC

ACTCATACAG TTTACCTAGC CATCAACAAA AGGGCGTAGA GATTGTGGCA ATCCATAGAA AGGGAAGTTC

ATCCGCGTTG TCATCCGATG AAGGAGCAGT AATGATGGAG TATGATTTTT TCCAGAAAA ATCAGCAGC

AAAAGCACTA ATACTTACAA AAGTTGTTTC GAGAATGAAG CAACGATGAT GAGTGCTTAT AATTCACCAG

AATCTTCTTC ATTTGCTGCT GCAGCAGCAG CAGCTGGAAA TATTATTAAT GGTGAAGCTT CTTCTGTTAC

TACAATATCT TGGGCTGCAG ATACTACTAC TACTTCACCT ACCAGTTCCA TTGATCTTTC ACTGAAGCTT

TCTTGTTAG
```

SL1.00sc07408.293.1.1 (SEQ ID NO: 53)

```
ATGAGGGAGA GGTTGTGTCT TGAGGTTGAG AGGTTAGGGC TTAGTGCTGT TATTATGGGG AGTCGAGGAT

TTGGAGCTAC GAAGAGGGGG AGTGATGAAA GACTTGGGAG TGTTAGTGAT TATTGTGTTA GGCACTGTGT

GTGTCCTGTT GTGGTTGTTA GGTATCCCGA TGATAAGGAT GCTGGAAATG CTGTTGTAGA GCCCGTGGTT

TCTGTTGCTT CAGCTGCTGA AGAAGACGAG GAGGAAGCTG AGTAGGATGA TGCTTCTGAG GATCGAAAAG

ATTCATAA
```

SL1.00sc07408_292.1.1 (SEQ ID NO: 54)

```
ATGGAAGATC CTTATGGATT TGAAGATCAT TTCCCTTCAA TGATGGAGAG ATTAGGCGCG GAAGGATTCA

TGAGGGAGCT TTGCAATGGA TTTTGTTTAC TTATGGATGT GAGTATAGGG CTAATAACAT ATGAAAGTTT

GAAGAGAAAC ACTATGAATC TTGGTTTAAA TGATTTAAGA GATGATGAGT TGATTTACAT GTTGGCTGAA

GGAGATTTGG ATGGTGATGG AGCACTTAAT CAAATGGAAT TTTGTATTCT CATGTTTAGA TTGAGTCCTG

GTTTAATGGA TGGATCTAAG CAATACATGG ATGATGTGGG GCTTATTCAT TTCCAACCCT AA
```

SL1.00sc07408_291.1.1 (SEQ ID NO: 55)

```
ATGAAAGGCC TATTTTCTTT ATGCATTTGC TACCAATTTC TCTTCATTTT ACTAACTTCT GCAGCATTAG

ACACAATCAC TACAGATAAA TCCATTAGAG ATGGTGACAC AATTGTTTCA GCTGGAGGGG TTTATGAGCT

TGGATTTTTC AGCCCTGGAA ATTCGAAGAA TCATTACGTT GGCATATGGT ACAAGAAAAT ATCAAATGGA

ACTGTTGTCT GGGTTGCAAA CAGAAGCATT CCACTTAATG ACACTTCAGG AGTGTTAACA CTTAATCCCA

ATGGAATTCT TGTACTTGTT GATAAATCCA ATGTCTCAAT TTGGTCATCA AACTCATCAA GATTGTTAAA

GAATCCAAAA GCACGGTTAC TGGATTCAGG GAACCTTGTT GTCAGTGATG GAAATGATAG AGGCCTGGAA

AATAATTTCG CGTGGCAGAG TTTTGACTAT CCAGGAAATA CTTTGTTACC TGGTATGAGG CTAGGAAAAG

ATTTTGTCAC GGGAATGAAT TGGCATTTAA CGTCATGGAA GAGCACAGAT GATCCTACTC CTGGTGATTA

TGTAGATCGT GTTGATTCAC ATGGATATCC ACAATTGTTT GTGTGGAAAA ATTCATCTAT AGTATTTAGC

TCAGGGCCAT GGAATGGTAT TGCATTTAGT GGTAGTCCTA ATAATAAACC AAATACATAT TACAGTTTCG

AGTTTGTTAT TAATCAGCAG GAAATTTACT ACACATATAC AATTAAGAAT GACTCCATAC CCACCAGGGT

GGTGCTCAAT CCGTCTGGTG TGCTAGAACA CCTAACATGG ATAGAGCGCA GTCAGAGCTG GTTTCTCTAC

TTGACAGCAC AATTTGATAA TTGTGATCGT TTTGGTTTAT GTGGACCTTA TCAAGTTGC AACATCAATA

ACTAAAATCC ATGTGACTGT TTGAAAGGTT TGAGCCTAG GTATCCTCAA GATTCTGCAA CAGAGTGGTC

TAGTGGTTGC ATAAGGAGAA CTTCTTTGGA TTGTACCCAT GATGGTTTTC TTAAATTTTC AGGTATCAAA

ATGCCTGATT CTAGAAACTC CTGGTATAAT GACAGCATGA ACCTTGAAGA TTGCGAGAAA ATGTGCTTGG
```

TABLE 3-continued

CTGATTGCAA TTGTACAGCC TACTCAGATC TTGATGTTAG AAATGGCGGA AGTGGATGCT TACTATGGTT

TGGTGAACTC ATAGATATAC GCGGGTTCAG CCAAAATGAA CAAAACCTGT ATGTGAGAGT TACTATGGTT

GAATTAGACA GGAAGGGGAG GAGAAAGAGG GCAGCCCTGA TTGGCGTCAT TTCAGCAGTG GTAGCAACAT

TTATCCTCAG CTTTTTAGCT TGGTTTTACT TCCGAAGAAG GAAAAGAAGA AGAGGATTAG AAGTTGAAAA

TGAGGACATG GAGCTTCCAT TGTTTGATTT AGTTACTGTT ACTACTGCTA CTGATAACTT CTCTTCTGCT

AATGTGATTG GAGAGGGAGG CTTTGGACCG GTTTACAAGG GTATCCTACC AAATGGACAA GATATTGCAG

TAAAAAGACT ATCGAAGCAT TCTGGACAAG CTTTCAAGA GTTAAAAAAT GAAATCGCTC TCATTTCCAA

GCTGCAACAT AGAAACCTTG TCAAGCTATT GGGTTGCTGC CTTGAAGGAG AAGAAAGGAT GCTAATCTAT

GAGTTCATGC CCAATGCTAG CTTGGACTAT TTCATTTTTG ATTCAAGTAG AAAAGCATCA CTTGCATGGA

AGAACCGTTT TGAAATTGCT ATGGGAATAT CTCGAGGTCT TCTTTACCTT CACCAGGATT CAAGATTACG

AATTATTCAC AGAGATCTCA AGACTAGCAA CATTTTATTA GATACTGACA TGAATGCCAA AATTTCGGAC

TTTGGCCTTG CCAAAATTTT TGGTGGAGAT CAAGTGGAAG GAAAAACTAA AAGAGTAATA GGGACATATG

GATATATGTC CCCGGAATAT GCTGTTGATG GGAAATATTC AGTAAAATCA GATGTATTCA GCATTGGCGT

AATTATTCTT GAAATAGTCA GTGGCAGAAA GAACAGAAAA TTTCGTCATT GGAACATCA TCACAATCTC

TTGGGACATG TAAGCACAAA ACTTCATTCC CTTTATTCAC TCTTAGCTTC CTATTGTGAT TACAACTGTA

TGACTGTGTT GTTCTGTTTG TAA

SL1.00sc07408_290.1.1 (SEQ ID NO: 56)

ATGGTATTGA TTTTGTTTTT TGTGTCAGCT ATGTTGAGGC TCTTCATTTG CTGTCAATTT CTCTTCATGT

TACTAACTTC TGCTGCATTA GACACAATCA CTACAAATAA ATCTATTAGA GATGGTAATA CAATTGTTTC

AGCTGGAGGG GTTTATGAGC TTGGATTTTT CAGCCCTGGA AATTCGAAGA ATCGTTACGT TGGCATATGG

TACAAGAAGA TATCACCTAC AACTGTTGTC TGGGTTGCAA ACAGAGACAT TCCACTTAAT GACACTTCAG

GAGTGTTAAC ACTTAATCCC AATGGAATTC TTGTACTTGT TGATAAATCC AATGTCTCAA TTTGGTCATC

AAACTCATCA AGATTGTTAA AGAATCCAAA AGCAAGGCTC CTGGATACCG CAAACCTTGT TGTTAGTGAC

GGAAATGATA GAGATCAGGG AATTAATTTC GCGTGGCAGA GTTTTGATTA TCCAGGAAAT ACTTTATTAC

CTGGAATGAA GGTAGGAATA GATTTGGTTA CGGGGATGGA TAGGTATGTA ACGTCGTGGA AGAGCACAGA

TGATCCTACT CCTGGTGATT ATGTAGATCG TGTTGATTCA CATGGATACC CGCAATTGTT CTTGTCGAGA

AATTCATCTG TAGTGTTTAG CTCAGGGCCA TGGACTGGTG CTGCATTTTC TAGTAGTCCT AGTAATAAAC

CATCTTTGTA TTATACGTTC GAGTTTGTTA TCAATCAGAA GGAAATTTAC TTCAAATATG AGCTTAAGAG

TGACTCTTTG CCCACCAGGG TGGTGCTCAA CCCGGATGGA GTGATACAAC ACCTAATATG GATTGAGCAT

ACTCAGAGCT GGTTTCTCTA CTTGACAGCA CAACTTGATA ATTGTGATCG TTTTGCTTTA TGCGGACCTT

ATTCAAGTTG CAACATCAAT AACTCCCCTC CATGTGACTG TTTGAAAGGT TTTGAGCCTA GGTATCCTCA

AGAATCTGCA GCAGACTGGT CTAGTGGTTG CGTAAGGAGA ACTTCTTTAA ATTGTACCCA TGATGGTTTT

CTTAAATTTA CGCGTATCAA GATGCCTGAT TCTAGAAACT CCTGGTATAA TGAGAGAATG AACCTTGAAG

ATTGCGAGAA AATGTGTTTA GCTGATTGCA ATTGTACAGC CTACTCAGAT CTTGATGTTA GAAATGGCGG

AAGTGGATGC TTACTATGGT TTGGAGAACT CATAGATATA CGAGAATTCA GCCAAAATGA GCAAAATCTA

TATGTGAGAG TAGCTGCTTC AGAATTAGGC GAATGTATAT TGACAGGTTC AAAAGTTGAA AATGAGGACA

TGGAGCTTCC ATTGTTTGAT TTAGTTACTG TTACAAGTTC CACTGAAAC TTCTCTTCTG CTAATGTGAT

TGGGGAAGGC GGATTTGGAC CGGTCTACAG GGGTATCCTA CCAAGTGGAC AAGAGATAGC AGTAAAGAGG

CTATCGAAGT ATTCTGGACA AGGCATTCAA GAGTTAAAAA ATGAAATCGT TCTCATTTCC AAGCTGCAAC

ATAGGAACCT TGTCAAGTTA TTGGGTTGCT GTCTTGAAGG AGAAGAACGG ATGCTAATAT ATGAGTTCAT

TABLE 3-continued

GCCCAACGCT AGCTTGGACT ATTTCATTTT TGATCCAAGC AGAAAAGCTT CACTTGGATG GAAGAATCGT

TTTGAAATTG CTATGGGAAT ATCTCGTGGT CTTCTTTACC TTCACCAGGA TTCAAGATTG AGAATTATTC

ACCGAGATCT CAAGACCAGC AACATTTTAT TAGATACTGA CATGAATGCC AAAATTTCTG ACTTTGGCCT

TGCCAAAATT TTTGGTGGTG ACCAAGAGGA AGGAAAAACT AAGAGAGTAA TAGGGACATA TGGATATATG

TCCCCGGAGT ATGCTGTTGA TGGGAAATAC TCAGTAAAAT CAGATGTATT CAGCATCGGT GTAATCATTC

TTGAAATAGT TAGTGGCAGA AGAACAGAA AATTTCGTCA TTTGAACAT CATCACAATC TCTTGGGACA

TGCATGGTTA CTTTGGATTG AAGGCAACGC GTTGGAACTG ATAGACGAAT GTATCAAAGA ATCCTTTTCA

GAATCTCAAG TGCTGAGATG CATCCAGGTT GGTTTGTTAT GCGTCCAAAA ACTCCCCGAG GATAGGCCTA

CAATGGCATC AGTAGTTTTC TGGTTAGGCA ATGAAGGTCT GGTTCTTCCT CAACCAAAGC AACCTGGTTT

TTTCATAGAG AGGAATTCAA TGGAATCAAC AGAATCATCA ACTGATGAAG TATATGTAAG TAGCAGCGTG

TCGATAACAG TTCTAGAGCC AAGATAG

SL1.0sc07408_289.1.1 (SEQ ID NO: 57)

ATGAAAGGGA ACATTTTTT ATTTTCTTGC TCAATTTTTC TTCCAGTCTT ACTAATTTCC ACTGCATTAG

ACACAATCAC AACAGAGAAA CCAATTAGAG ATGGTGACAC AATTATTTCA GCTGGAGGGG TTTTTGAGCT

TGGATTTTTC AGCCCTGGAA ATTCGAAGAA TCGTTACGTT GGCATATGGT TTAAGAAGAT AGCAACTAGA

ACTGTTGTCT GGGTTGCCAA CAGAAACTTC CCACTGAATG ACAATTCAGG AGTGTTATCA CTCAATCCCA

ATGGAATTCT TGTACTTCTT CGTAATTCCA ATGCCTCAAT TTGGTCTTCA AACTCATCAA GATTGTTGAC

GAATCCAAAA GCATGGCTCC TGGATTCTGG TAACCTTGTT GTGACTGATG GAAATGATAG TGATCCAGAA

GTTAATTTCG CGTGGCAGAG TTTTGATTAT CCAGGAGATA CTTTACTACC TGGGATGAAG CTTGGACGTA

ATCTGGTCAC GGGCATGGAT TGGTACATAG AGTCATGGAA GAGCAGTGAT GATCCTGCGC CTGGTGAATA

TATAGAACGT CTTGATTCTC ATGGATACCC ACAATTTTTC GTGTGGCAAA ATTCATCTAT AGTATATAGC

ACAGGGCCAT GGAATGGTAT CACATTTAGC AGTAGTCCAA AAAATCAACC AGCTATATAT TATGCTTTCG

AGTTTGTTAT TAAACAGAAG GAGATTTACT TTAAATACGA GCTAAACGAG TCCCTGCCCA CCAGGGTAGT

GATCAATCAG GCTGGAATGG TAGAACACCT AACATGGATT GAGCGAAATC AGAGATGGAT AGTCTATGTA

TCAACACAAT CTGATAATTG TGATCGTTTT GCTTTATGTG GTCCTTATGC AAGTTGCAAC ATCAATAACT

CTCCTCCATG TGACTGCTTG CAAGGTTTCG AGCCTAGGTA TCCTGAACAA TGGTATGCAG TGGACTGGTC

TAATGGTTGT ATAAGGAAAA CTTCTTTGTC TTGTAACCAA GATGGTTTTC TTAAATTTAC GAATATCAAG

ATGCCGGATT CTAGACACTC CTGGTATAAT GTAAGCATGA ATCTTGAAGA ATGCAAGAAA ATGTGCTTGG

CTGATTGCAA TTGTACAGCC TACTCAAATC TTGATATAAG AAATGGCGGA AGTGGATGTT TACTATGGTT

CGGTGAGCTC ATTGATATTA GAGAGTACAA CAAAAATGAG CAACGCCTGT TTGTGAGAGT TGCTGCTTCA

GAATTAGATC CAGTCAGGAC TTGGAGGGGA AAGTGGCCAG CTCTGATTGC GGTCATTTCA GCACTAGCAG

CAACTTTTAT CCTCATCTTT GTAGCTTGGT TTACCTTCCA AAGAAGGAAC AAAAAAACAG ACAAACATAC

TGGAGGTTCA GAAGTTGGAA AGAATGACCT TGAGTTGCCA TTGTTTGATT TAGTTACTGT TACTACTTCC

ACTGAAAGTT TCTCTTCTGC GAATGTGATT GGTGAGGGTG GCTTTGGACA GGTTACAAG GGTATTCTAC

CAGATGGACA AGAGATAGCA GTAAAGAAGC TATCGAAGTA TTCTGGACAA GGCGTTCAAG AGTTAAAAAA

TGAAATTGTT TTCATTTCCA AGCTGCAACA TAGAAACCTT GTCAAGCTTT TGGGTTGCTG CCTTGAAGGA

GAAGAAAAGA TGCTAATCTA TGAGTTTATG CCCAACTCTA GCTTGGACTG TTTCATTTTT GATCCAAGCA

GAAAAGCTTC ACTTACATGG AAGAATCGTT TTGAAATTGC TGTGGGAATA TCTCGAGGTC TTCTATACCT

TCATCAGGAC TCAAGATTTA GAATTATTCA TAGAGACCTC AAGACCAGCA ACATTTTACT AGATGGCAAC

ATGAATGCCA AAATTGCTGA CTTTGGCCTT GCCAAAATTT TTGGCGGAGA ACAAGTGGAA GGAAATACTA

TABLE 3-continued

```
AGAGAGTGAT AGGGACATAT GGATATATGT CACCTGAGTA TGCTGTTGAT GGGAAATATT CAATAAAATC
CGATGTATTC AGTATTGGCG TCATCATTCT AGAACTAGTT AGTGGCAGAA GGAACAGGAA ATTTCGTCAT
TTGGAACATC ATCACAATCT TTTGGGACAT GCATGGTTAC TTTGGACTGA AGACAAAGCG TTGGAACTGA
TGGACGAATG TTTGAAAGAA TCATTTGCGG AATCTCAAGT GTTGAGATGC ATCCAGGTTG GTTTGTTGTG
CGCCCAAAAA CACCCTGAGG ATAGGCCTAC AATGGCATCA GTAGTTTTCT GGTTGGGAAA TGAAGGCCTG
GTTCTTCCTC AACCAAAGCA GCCTGGATTT TTTATCGAAA GGAATTCAAT GGAATCAACA GAATCAGCTC
AGTTTATAAA CACGATCACA ACAGATAGAT CCATTAGAGA CGGTGACACA ATTGTTTCAG CTGGTGGGAT
TTATGAGCTT GGATTTTTCA GTTCTGGAAA TGCGAAGAAT CGTTACGTAG GCATATGGTA CAAGAAGATA
TCAACTCAAA CTGTTGTCTG GGTAGCAAAC AGAGATATTC CACTTATTGA CACATCAGGA GTGTTAATAC
TCAAACCCAA TGGAATTCTT GTACTTGTTG ATAATTCCAA TACATCAATT TGGTCATCAA ACTCATCAAG
ACCGTTAAAG GATCCAAAAG CACGGATCCT GGATTCCGGG AACCTTGTTG TCAATGATGG AAATGAAAGA
GACCTGGAAA TTAACTTCGC ATGGCAGAGT TTTGATTATC CAGGAAATAC TTTTATACCT GGAATGAAAC
TTGGACGTAA TTTGGTCACG GGCATGGATT GGTATATGTC GTCTTGGAAG AGCATTGATG ATCCTTCTCC
TGGTGAATAT ATAAACCGTC TTGATTCTCA TGGATACCCG CAATTGTTTG TGTGGAAAAA TTCAACTATA
GTGTCTAGCT CAGGGATATG GAAAGGTAAT GCATTTACTG TTAGTGCTAA CAGTAGACCA AATACACATT
ACACTTCCGA GTTTATAATT AATCAGCAGG AAATTTACTA CCAATTCAAG CTTAAGAACG AGTCACTGCC
CAGCAGGATG GTGCTCAACC CGGAAGGGCT GATAGAACAC CTAACATGGA TTGAGAGCAG TCAAAGCTGG
TTTCTGTACT CAACAGTACA GTTTGATAGC TGTGGTCGTT TTGCTTTATG CGGTCCTTAT TCAAGTTGCA
ACATCAATAA CTCCCCTCCA TGTGACTGTT TGCAAGGTTT CAATCCTAGG GTTCCTCAAC AGTCTGCAGC
AGATTGGTCT TCTGGTTGTG TTAGGAGCAC TTCTTTGGAT TGTAACAAAG ACGGTTTTCT TAAATTTACA
GGCATCAAGA TGCCTGATTC TAGAAACTCC TGGTTTAATA AGAGCATTAA CCTTGAAGAA TGTGAGAAAT
TATGCTTAGC TAATTGCAAC TGTACAGCCT ACTCAAATCT TGATGTCAGA AATGGCGGAA GTGGATGCTT
ACTATGGTTC GGAGATCTCA TTGATATTCG AGAGTTGAGC CAAAATGAGC AAAACCTGTT TGTGAGAGTT
GCTGCTTCAG AAATAGACAG GAAGCAAAGG AGAAAGATGT CAGTCCTGAT TGGTGTCATT TCAGCAGTGG
TAGCAACATT TATCCTCAGC TTTTTAGCTT GGTTTTACTT CCAAAGAAGG AAAAGAAGAA TAGGTCCAGA
AGTTGAAAAT GAGGACATGG AGCTTCCATT GTTTGATTTA GTTACTGTTA CTACTGCCAC TGGGGACTTC
TCTGCTATGA ATGTGATCGG GAAGGGTGGA TTTGGACCGG TTTACAAGGG TATCCTACCA AATGGACAAG
AGATAGCAGT GAAGAGGTTA TCAAAGCATT CTGGACAAGG CTTACGAGAG TTAAAAAATG AATTCGTTCT
CATTTCCAAG CTGCAACACA GGCCCCTTGT CAAGCTTTTG GGTTGCTGCC TTGAAAGAGA AGAACGGATG
CTCATCTATG AGTTTATGCC CAATGCTAGC TTGGACTATT TCATTTTTGA TCCAAGCAGA AAAACTTCAC
TTTCATGGAA GAACCGCTTT GAAATTGCTA TAGGAATATC TAGAGGTCTT CTTTACCTTC ACCAGGACTC
AAGATTAAGA ATTATTCACA GAGATCTCAA GACCAGCAAC ATCTTATTAG ATACTGACAT GAATGCCAAA
ATTTCTGACT TCGGCCTTGC CAAGATATTT GGTGGAGATC AAGTGGAAGG AGAAACTAAG AGTATAGTAG
GGACATATGG ATATATGTCC CCGGAGTATG TTGTTGATGG GAAATATTCA GTAAAATCCG ATGTATTCAG
CATTGGTGTA ATTATTCTTG AAATAGTTAG TGGCAGAAAG AACAGGAATT TTCGTCATTT GGAACATCAT
CACAATCTCT TGGGACATGC ATGGTTACTT TGGACTGAAG GCAACGCGTT GGAATTCATG GATGAACGTT
TGAAAGAATC ATTTTCAGAA TCTCAAGTGT TGAGATGCAT CCAGGTCGGT TTGTTATGCG TCCAGAAACT
CCCAGAGGAC AGGCCTATAA TGGCATCAGT GGTTTTTTGG TTGGGAAATG AAGGTCTGGT TCTTCCTCAA
CCAAGGCATC CAGGTTTCTT CACAGAGAGG AATCCAATGG AATCTACTGA TGAAGAATGT CTAAGTAACA
ACGCGACGTT AACTGTTCTT GAGCCAAGAT AG
```

TABLE 3-continued

SL1.00sc07408_288.1.1 (SEQ ID NO: 58)

ATGGCAATGC TTCAATGGTT CCTCTTCTT TGCATTTTCT TCATCTCAGC TTCTGCTGCT AAAGTTCAAA

CCAAGGTAAC TGATAATCCT GCTGATGAGC TGGTATCTGC CCTTAATAGT AACAGAACTG CGAATAAATT

ATCCTCCTTA TACAGTAACC CTGGCTTGGC ATGCTTGGCT CTGCAATATA TAAAAGCATA CGGAGGTGAT

TGTAAAGTAG TTGGAGGGCC AGATGGAAAG AAACCTGCTG AATCTGAATT CGCCCAAGAA TTTGCCCCCA

ACTGTGGTGT GCAGGCATCA TCGCTTGCTC AAATAACTGG AAGATTTCTC GCATGTCAAT CTAAGTATGC

GGAACCTTCT GAAGCATTCA ATGATATTCT TATAAGAAAT ACCAAGAGTT TGGATATTCT TGTGTACTCT

AATCACACTG AGGTTGGTGC TGCTGTGAGT GGCTCCGGTG GTGGTGGCCC CTATTTCTGG TGTGTACTCT

TCAGTAATGG CAAACCAAAG AGTAGCTTTT CCAGAGGTGG AGTTGAGCCT AAGGTAAGTA GACCTGGATG

CTTCAGTGGT TCTAATGACC AATGCAGTGG TGCTAATACT TTGTCTCAAA CCATATATCT CTGGACAATC

ACTGTAGGAG CTTCCGTTGC ACTGCTTTAT GCCTTAGGAG TATGA

SL1.00sc07408_287.1.1 (SEQ ID NO: 59)

ATGGGAATAT CAAGAGGGAT TCTTTATCTT CACCAGGATT CCAGATTAAG GATCATACAT AGAGATCTAA

AGACGAGCAA CATTTTACTG GACAGTGAAT GGAATCCCAA GATTTCAGAC TTTGGACTGG CTAGGATTAT

TGGCTGTGAC CAAAACGAAG CAAGAACAAA AAGAGTAATA GGGACATATG GAGATATGTC TCCAGAATAC

GCAGTTGATG GGAAATTTTC AGTGAAATCA GATGTTTTCA GTCTTGGTGT CTTCTGCTA GAAATAGTAA

GTGGAAGAAA GAACAGAACA TTTCGTCATC CAGATCACCA CCATAGTCTT ATAGGACATG CTTGGTTATT

ATGGAACGAA GGAAAAGCCT TGGAACTAAT CGATGATTGT TTAAAAGAAT CGTTTGTGGA ATCCCAAGTG

CTAAGATGTG TTCATGTGGC ACTGTTATGT GTTAACGAC TAACAGATGA AGACCAACA ATGTCATCAG

TGGTATTCAT GTTAAGCCAT GAAGAAGTGG CATTACCTCA ACCAAAGGAG CCTGGTTTCT TCATAGAGAG

AAGTATAGCT GAAACAGATG ATTCAAATGA GAAAAGGTGT ATCAGTGACA ATGTTTTGAC ATTAACAATT

CTTCAACCAA GATAG

The invention claimed is:

1. A method for producing a tomato plant that is tolerant to exposure to continuous light, the method comprising the steps of:
   (a) providing a donor tomato plant which is tolerant to exposure to continuous light, selected from the group consisting of S. neorickii, S. chilense, S. pennellii, S. peruvianum, S. habrochaites and S. chmielewskii;
   b) crossing said donor tomato plant with at least one recipient S. lycopersicum plant which is not tolerant to exposure to continuous light, to produce offspring tomato plants,
      wherein said crossing results in the introduction of genomic material from said donor tomato plant into the corresponding region of the genome of said at least one recipient tomato plant; and
   c) detecting in chromosome 7 of at least one offspring plant the presence of a genomic region from the donor tomato plant linked to tolerance to continuous light, wherein the genomic region comprises a Light-Harvesting Chlorophyll B-Binding Protein 3 (LHCB3) gene;
      wherein said genomic region is located on chromosome 7 in a region bordered by markers "7-20-1" and "7-20-2" between 72 and 75 cM based on the EXPEN2000 linkage map; and wherein said genomic region in DNA isolated from the offspring plant is detected by use of a genetic marker, which marker is linked to said genomic region comprising the LHCB3 gene,
   thereby producing at least one offspring tomato plant which is tolerant to exposure to continuous light, said offspring plant comprising said LHCB3 gene.

2. A method for increasing the yield of a tomato plant line, said method comprising:
   (a) obtaining a tomato plant produced by the method according to claim 1;

(b) crossing the selected plant with a plant of said tomato plant line the yield of which is to be increased to produce offspring plants;

(c) optionally backcrossing or selfing said offspring plant to produce further offspring plants, and (d) selecting from said offspring plants of step (b) or (c) a plant having said genomic region linked to continuous light-tolerance and exhibiting tolerance to exposure to continuous light and having increased yield as compared to said plant of said tomato plant line used in step (b);

wherein tolerance to exposure to continuous light is determined by exposing the tomato plant for a period of 3 weeks to 90 days of continuous light having an intensity of about 131 µmol m$^{-2}$ s$^{-1}$ from fluorescent tubes, wherein the tomato plant is grown at 21° C. and a relative humidity between 60-80%.

3. The method according to claim 1, further comprising:

e) backcrossing said at least one offspring tomato plant which is tolerant to exposure to continuous light to said at least one recipient *S. lycopersicum* plant which is not tolerant to exposure to continuous light, to produce a *S. lycopersicum* plant which is tolerant to exposure to continuous light, whereby said *S. lycopersicum* plant which is tolerant to exposure to continuous light is characterized by the presence of a genomic region from the donor tomato plant linked to tolerance to continuous light, wherein the genomic region comprises a Light-Harvesting Chlorophyll B-Binding Protein 3 (LHCB3) gene on chromosome 7 in a genomic region bordered by markers "7-20-1" and "7-20-2" between 72 and 75 cM based on the EXPEN2000 linkage map.

4. A method of producing a continuous light-tolerant inbred tomato plant, the method comprising the steps of:

a) obtaining a continuous light-tolerant *Solanum lycopersicum* tomato plant produced by the method according to claim 3;

b) crossing said continuous light-tolerant tomato plant with itself or another tomato plant to yield progeny tomato seed;

c) growing said progeny tomato seed of step b) to yield an additional continuous light-tolerant tomato plant and;

d) repeating the crossing and growing steps from 0 to 7 times to generate a continuous light-tolerant inbred tomato plant;

wherein said tolerance is determined by the presence of a genomic region linked to tolerance to continuous light, wherein the genomic region comprises a Light-Harvesting Chlorophyll B-Binding Protein 3 (LHCB3) gene of *S. neorickii, S. chilense, S. peruvianum, S. habrochaites, S. chmielewskii,* or *S. pennellii,* wherein the genomic region is bordered by markers "7-20-1" and "7-20-2" between 72 and 75 cM based on the EXPEN2000 linkage map; wherein tolerance to exposure to continuous light is determined by exposing the tomato plant for a period of at least 3 weeks to continuous light having an intensity of 131 µmol m$^{-2}$ s$^{-1}$ from fluorescent tubes, wherein the tomato plant is grown at 21° C. and a relative humidity between 60-80%.

5. The method according to claim 4, wherein step d) further comprises the step of identifying plants that exhibit continuous light tolerance and possess commercially desirable characteristics.

6. The method according to claim 4, wherein said method further comprises the step of selecting inbred tomato plants homozygous for a genomic region comprising the LHCB3 gene linked to continuous light-tolerance.

7. The method of claim 1, wherein the genomic region comprising the Light-Harvesting Chlorophyll B-Binding Protein 3 (LHCB3) gene is detected by using a molecular marker selected from the group consisting of SEQ ID NO:19 and SEQ ID NO:23.

8. A method for producing a *S. lycopersicum* tomato plant that is tolerant to exposure to continuous light, the method comprising the steps of:

a) providing a donor *S. lycopersicum* tomato plant obtained by the method according to claim 3;

b) crossing said donor tomato plant with at least one recipient *S. lycopersicum* plant which is not tolerant to exposure to continuous light, to produce offspring *S. lycopersicum* tomato plants, wherein said crossing results in the introduction of genomic material from said donor tomato plant into the corresponding region of the genome of said at least one recipient tomato plant; and c) detecting in chromosome 7 of at least one offspring plant the presence of a genomic region comprising a Light-Harvesting Chlorophyll B-Binding Protein 3 (LHCB3) gene linked to tolerance to continuous light; wherein said genomic region is bordered by markers "7-20-1" and "7-20-2" between 72 and 75 cM based on the EXPEN2000 linkage map; said genomic region is detected by use of a genetic marker in DNA isolated from said offspring plant, which marker is linked to said genomic region comprising the LHCB3 gene, thereby producing at least one offspring *S. lycopersicum* tomato plant which is tolerant to exposure to continuous light, said offspring plant comprising said genomic region comprising said LHCB3 gene.

9. The method according to claim 1, wherein said donor tomato plant which is tolerant to exposure to continuous light is selected from the group consisting of *S. neorickii, S. chilense,* and *S. pennellii.*

* * * * *